(12) United States Patent
Cook et al.

(10) Patent No.: US 9,056,858 B2
(45) Date of Patent: Jun. 16, 2015

(54) INDAZOLE AND PYRAZOLOPYRIDINE COMPOUNDS AS CCR1 RECEPTOR ANTAGONISTS

(75) Inventors: Brian Nicholas Cook, Danbury, CT (US); Daniel Kuzmich, Danbury, CT (US); Can Mao, New Milford, CT (US); Hossein Razavi, Danbury, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 559 days.

(21) Appl. No.: 13/499,939

(22) PCT Filed: Oct. 19, 2010

(86) PCT No.: PCT/EP2010/053142
§ 371 (c)(1),
(2), (4) Date: Jun. 19, 2012

(87) PCT Pub. No.: WO2011/049917
PCT Pub. Date: Apr. 28, 2011

(65) Prior Publication Data
US 2012/0270870 A1 Oct. 25, 2012

Related U.S. Application Data

(60) Provisional application No. 61/253,590, filed on Oct. 21, 2009.

(51) Int. Cl.
| | |
|---|---|
| *C07D 401/12* | (2006.01) |
| *A61K 31/5377* | (2006.01) |
| *A61K 31/4439* | (2006.01) |
| *A61K 31/437* | (2006.01) |
| *C07D 213/62* | (2006.01) |
| *C07D 471/04* | (2006.01) |

(52) U.S. Cl.
CPC .......... *C07D 401/12* (2013.01); *A61K 31/5377* (2013.01); *A61K 31/4439* (2013.01); *A61K 31/437* (2013.01); *C07D 213/62* (2013.01); *C07D 471/04* (2013.01)

(58) Field of Classification Search
CPC .. C07D 471/04; C07D 413/14; C07D 213/62; A61K 31/5377; A61K 31/4439; A61K 31/437
USPC ............ 546/120, 275.7; 514/234.2, 303, 338; 544/127
See application file for complete search history.

(56) References Cited

U.S. PATENT DOCUMENTS

| | | | |
|---|---|---|---|
| 4,999,363 A | 3/1991 | Oshima et al. | |
| 5,118,701 A | 6/1992 | Oshima et al. | |
| 5,242,931 A | 9/1993 | Oshima et al. | |
| 5,302,596 A | 4/1994 | Oshima et al. | |
| 5,534,481 A | 7/1996 | Suzuki et al. | |
| 5,612,360 A | 3/1997 | Boyd et al. | |
| 5,616,537 A | 4/1997 | Yokota et al. | |
| 5,670,452 A | 9/1997 | Suzuki et al. | |
| 5,760,028 A | 6/1998 | Jadhav et al. | |
| 5,763,616 A | 6/1998 | Suzuki et al. | |
| 5,770,544 A | 6/1998 | Yokota et al. | |
| 5,973,156 A | 10/1999 | Chambers et al. | |
| 6,025,374 A | 2/2000 | Castro Pineiro et al. | |
| 6,107,321 A | 8/2000 | Madin | |
| 6,211,219 B1 | 4/2001 | MacLeod et al. | |
| 6,326,382 B1 | 12/2001 | Villalobos et al. | |
| 6,331,640 B1 | 12/2001 | Fotouhi et al. | |
| 6,498,255 B2 | 12/2002 | Villalobos et al. | |
| 6,716,978 B2 | 4/2004 | Marfat | |
| 6,784,182 B2 | 8/2004 | Liebeschuetz et al. | |
| 6,803,384 B2 | 10/2004 | Fotouhi et al. | |
| 6,855,715 B1 | 2/2005 | Liebeschuetz et al. | |
| 6,878,725 B2 | 4/2005 | Liebeschuetz et al. | |
| 6,900,196 B2 | 5/2005 | Liebeschuetz et al. | |
| 6,936,611 B2 | 8/2005 | Liebeschuetz et al. | |

(Continued)

FOREIGN PATENT DOCUMENTS

| | | | |
|---|---|---|---|
| EP | 345747 A2 | 12/1989 | |
| EP | 1201268 A2 | 5/2002 | |

(Continued)

OTHER PUBLICATIONS

Berge, S. M. et al., "Pharmaceuticals Salts", Journal of Pharmaceutical Sciences, Jan. 1977, vol. 66, No. 1, pp. 1-19.
Caplus: 2009:2329372, Loiseleur, 2009.
Engbersen, J.F.J. et al., "Synthesis of 2-Aminomethyl-1,10-phenanthroline. A new Chelating Agent and Versatile Synthon for other Chelating Compounds", Journal of Heterocyl Cehm., 1986, vol. 23, pp. 989-990.
International Search Report and Written Opinion for PCT/US2010/053477 mailed Apr. 21, 2011.
International Search Report and Written Opinion for PCT/US2010/058594 mailed Jan. 25, 2011.
International Search Report and Written Opinion for PCT/US2011/033923 mailed Oct. 6, 2011.

(Continued)

*Primary Examiner* — Jennifer M Kim
(74) *Attorney, Agent, or Firm* — Michael P. Morris; Mary-Ellen M. Devlin

(57) ABSTRACT

Disclosed are CCR1 receptor antagonists of the formula (I)

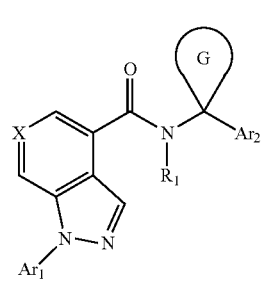

Figure 1:
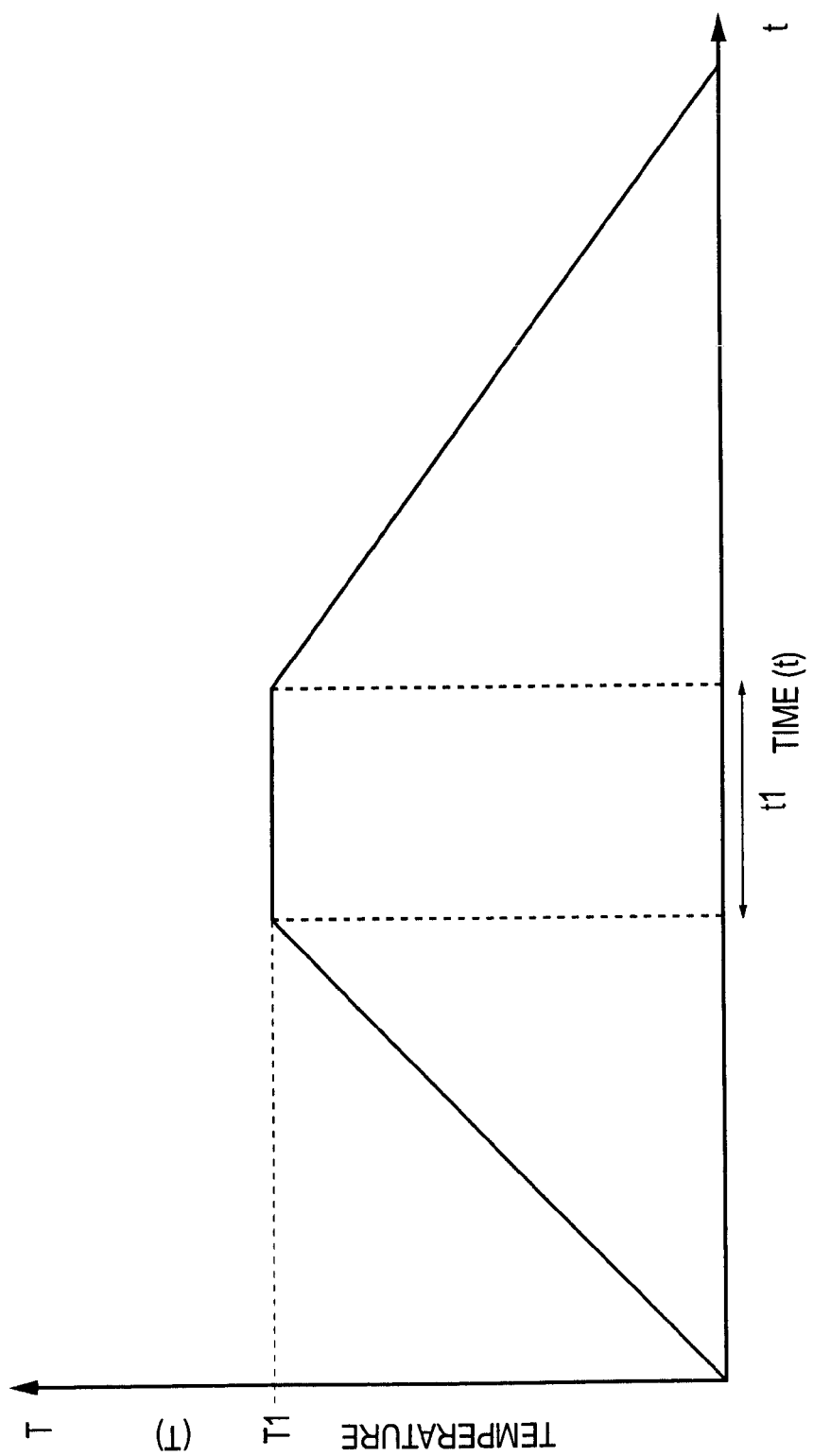
Figure 2:
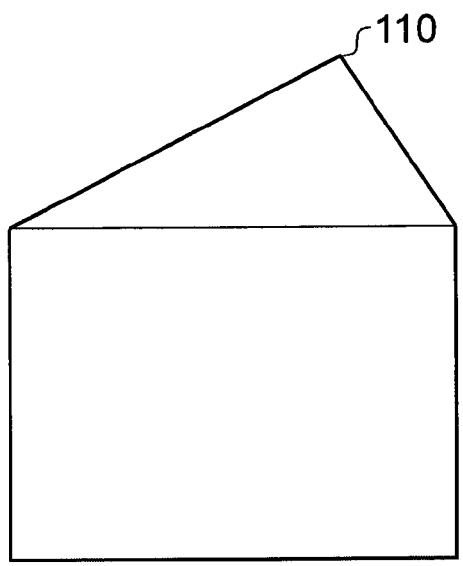
Figure 3:
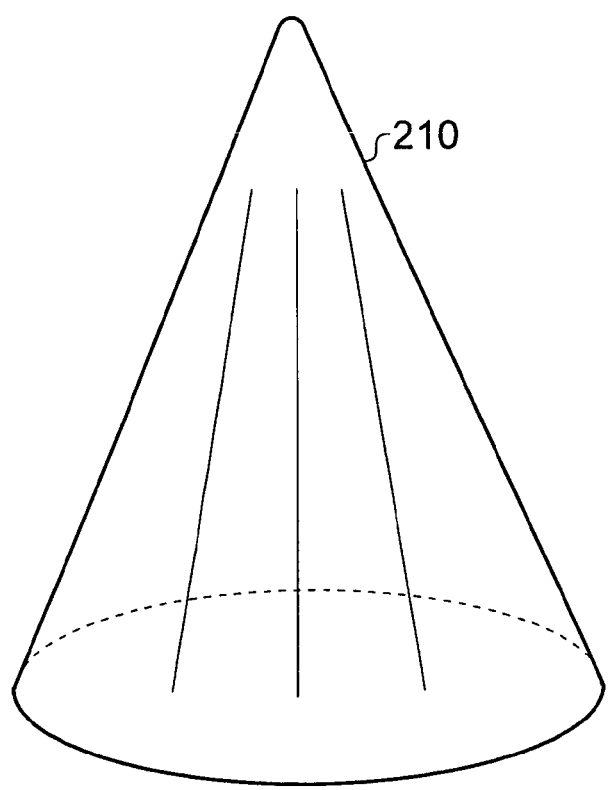
Figure 4:
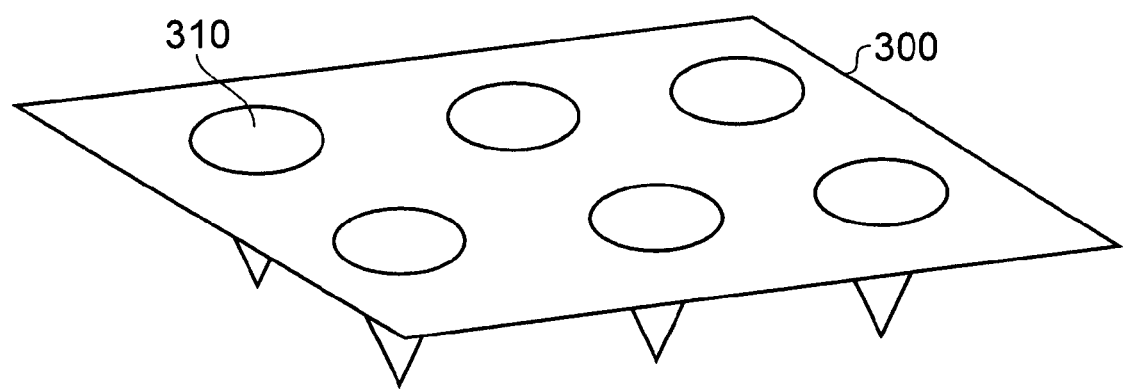
Figure 5:
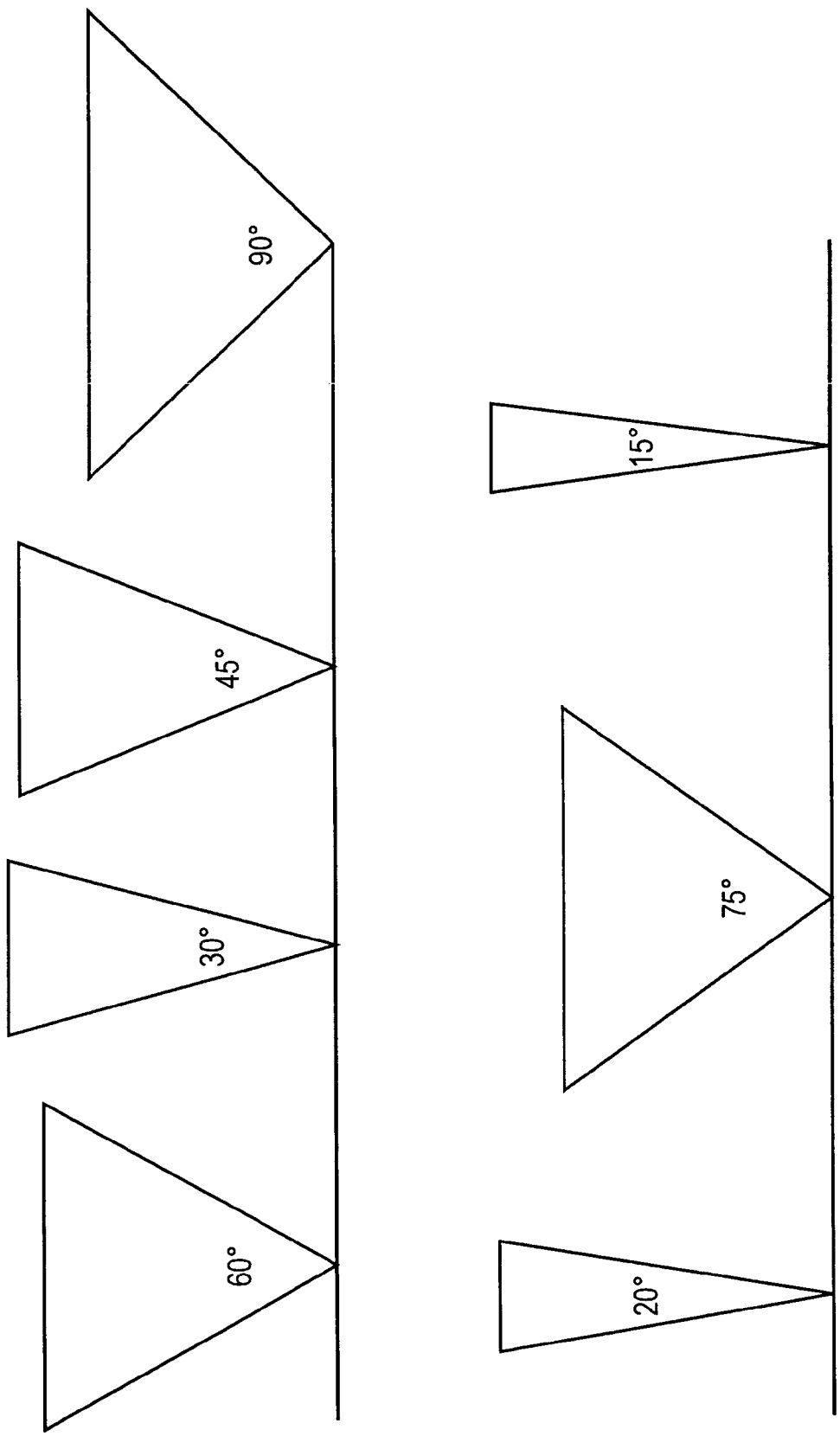
Figure 6:
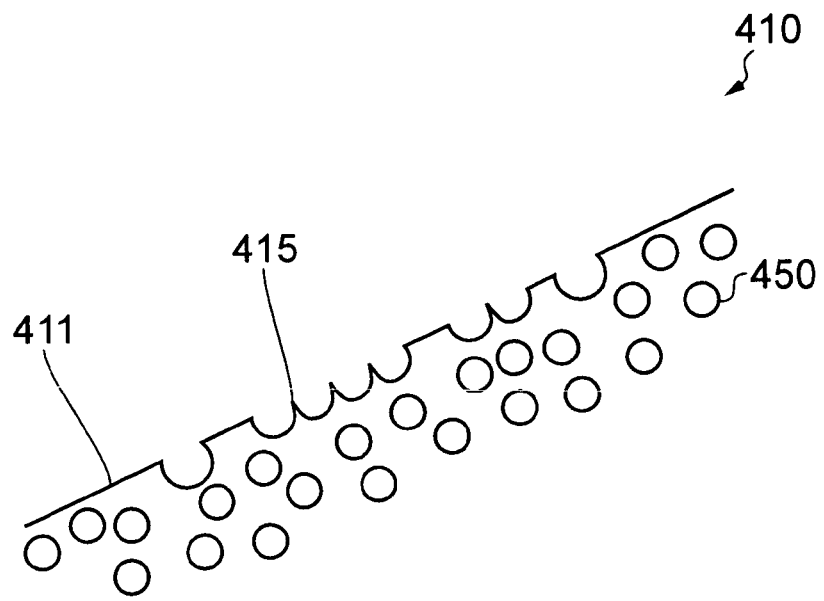
Figure 7:
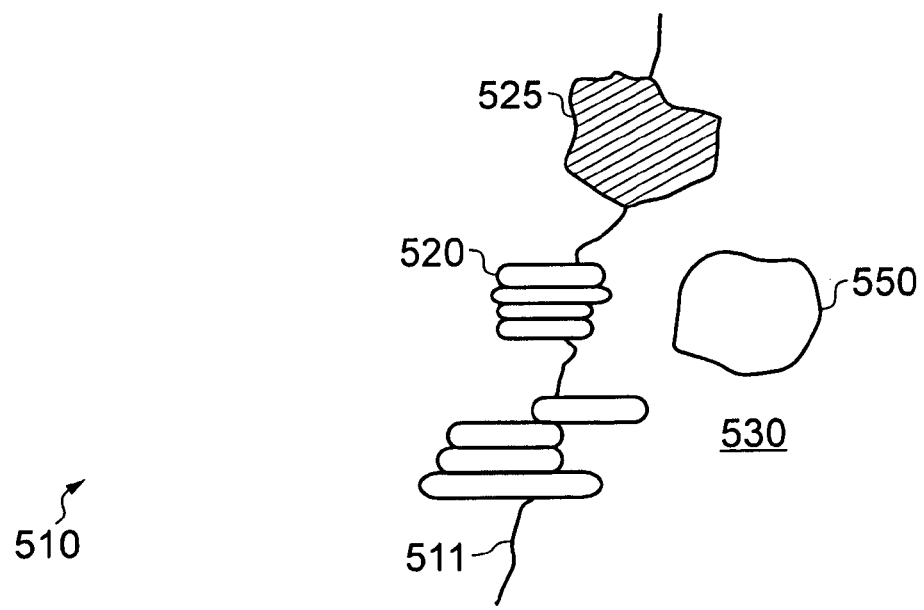
Figure 8:
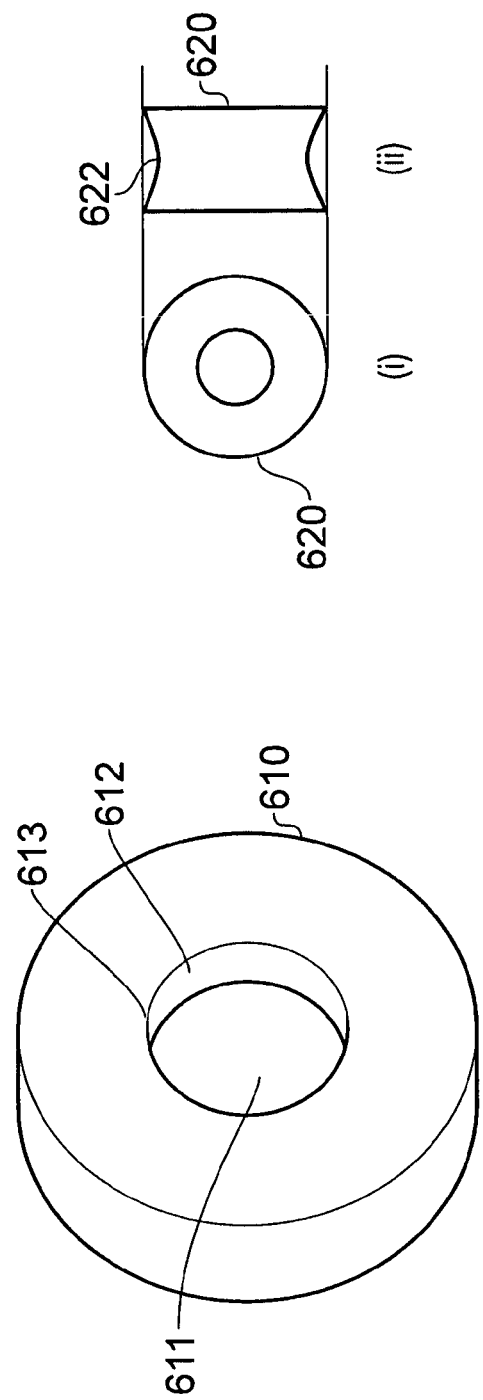
Figure 9:
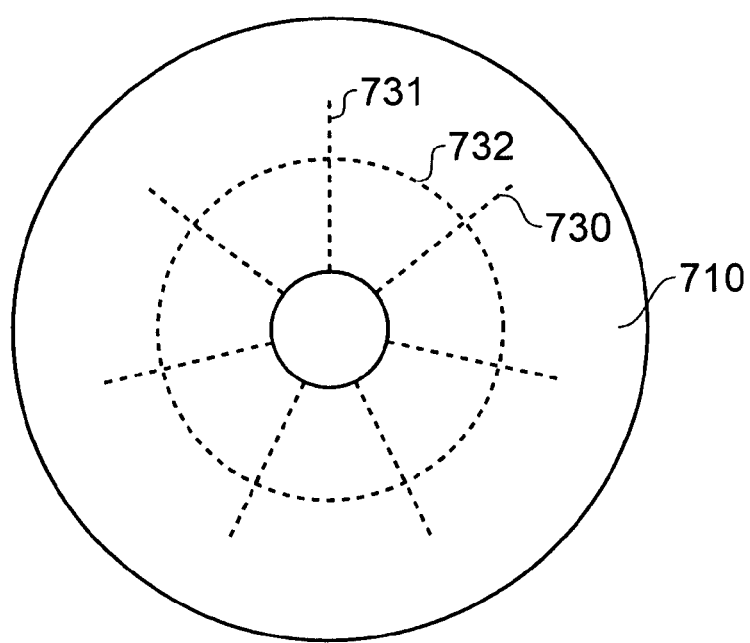
Figure 10:
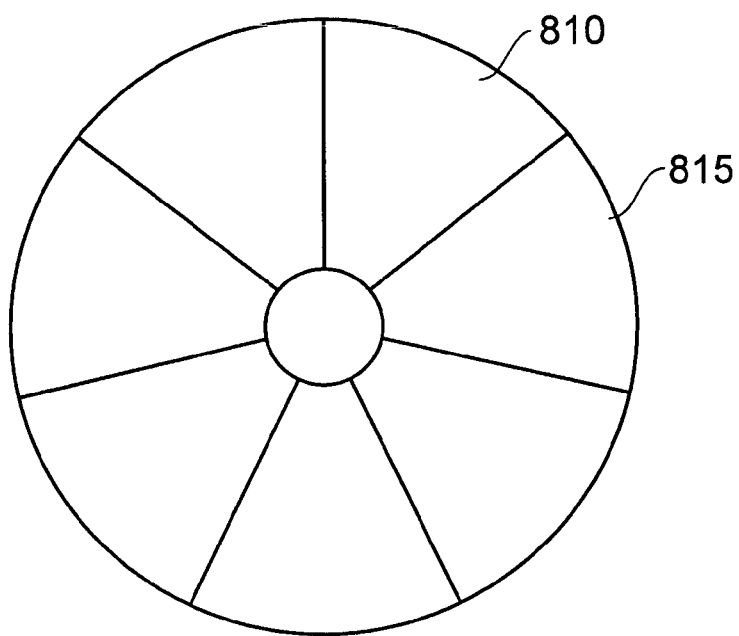

wherein $Ar_1$, $Ar_2$, $R_1$, X and G are disclosed herein. Also disclosed are compositions, methods of making and using compounds of the formula (I).

17 Claims, 9 Drawing Sheets

(56) References Cited

U.S. PATENT DOCUMENTS

| | | |
|---|---|---|
| 7,049,297 B2 | 5/2006 | Zhang et al. |
| 7,053,078 B2 | 5/2006 | Liebeschuetz et al. |
| 7,129,264 B2 | 10/2006 | Smallheer et al. |
| 7,223,782 B2 | 5/2007 | Atkinson et al. |
| 7,429,609 B2 | 9/2008 | Ohi et al. |
| 7,879,873 B2 | 2/2011 | Cook et al. |
| 8,008,327 B2 | 8/2011 | DiSalvo et al. |
| 8,063,065 B2 | 11/2011 | Cook et al. |
| 8,263,597 B2 | 9/2012 | Kuzmich et al. |
| 8,293,917 B2 | 10/2012 | Cook et al. |
| 8,338,610 B2 | 12/2012 | Kuzmich et al. |
| 2002/0037860 A1 | 3/2002 | D'Andrea et al. |
| 2002/0052373 A1 | 5/2002 | Zorn et al. |
| 2004/0127536 A1 | 7/2004 | Bhagwat et al. |
| 2005/0009876 A1 | 1/2005 | Bhagwat et al. |
| 2005/0020564 A1 | 1/2005 | Atkinson et al. |
| 2005/0108582 A1 | 5/2005 | Fung |
| 2005/0208582 A1 | 9/2005 | Ohi et al. |
| 2005/0261339 A1 | 11/2005 | Ohi et al. |
| 2006/0035938 A1 | 2/2006 | Bladh et al. |
| 2006/0252781 A1 | 11/2006 | Basarab et al. |
| 2006/0281739 A1 | 12/2006 | Gadek et al. |
| 2007/0004761 A1 | 1/2007 | Basarab et al. |
| 2007/0155738 A1 | 7/2007 | Steeneck et al. |
| 2008/0262040 A1 | 10/2008 | Callahan et al. |
| 2008/0280956 A1 | 11/2008 | Gilligan et al. |
| 2009/0054397 A1 | 2/2009 | Ohi et al. |
| 2010/0093724 A1 | 4/2010 | Cook et al. |
| 2011/0034512 A1 | 2/2011 | Disalvo et al. |
| 2011/0086846 A1 | 4/2011 | Cook et al. |
| 2011/0137042 A1 | 6/2011 | Razavi et al. |
| 2011/0230521 A1 | 9/2011 | Cook et al. |
| 2011/0294808 A1 | 12/2011 | Kuzmich et al. |
| 2012/0035370 A1 | 2/2012 | Cook et al. |
| 2012/0136158 A1 | 5/2012 | Cook et al. |
| 2012/0270870 A1 | 10/2012 | Cook et al. |
| 2012/0270879 A1 | 10/2012 | Cook et al. |
| 2012/0322790 A1 | 12/2012 | Betageri et al. |

FOREIGN PATENT DOCUMENTS

| | | |
|---|---|---|
| JP | 10001478 A | 1/1998 |
| JP | 2008546794 A | 12/2008 |
| WO | 9217475 A1 | 10/1992 |
| WO | 9401415 A1 | 1/1994 |
| WO | 9500509 | 5/1995 |
| WO | 9617842 A1 | 6/1996 |
| WO | 9711945 A1 | 4/1997 |
| WO | 9719073 A1 | 5/1997 |
| WO | 9723480 A1 | 7/1997 |
| WO | 9803504 A1 | 1/1998 |
| WO | 9923076 A1 | 5/1999 |
| WO | 0021920 A1 | 4/2000 |
| WO | 0076970 A2 | 12/2000 |
| WO | 0076971 A2 | 12/2000 |
| WO | 0100656 A2 | 1/2001 |
| WO | 0165218 A1 | 9/2001 |
| WO | 0210137 A2 | 2/2002 |
| WO | 03087085 A1 | 10/2003 |
| WO | 03101968 A1 | 12/2003 |
| WO | 03105853 A1 | 12/2003 |
| WO | 2004014905 A1 | 2/2004 |
| WO | 2004043924 A1 | 5/2004 |
| WO | 2004056831 A1 | 7/2004 |
| WO | 2004094372 A2 | 11/2004 |
| WO | 2005016929 A1 | 2/2005 |
| WO | 2006091496 A2 | 8/2006 |
| WO | 2006125119 A1 | 11/2006 |
| WO | 2007002293 A1 | 1/2007 |
| WO | 2007028083 A2 | 3/2007 |
| WO | 2007102883 A2 | 9/2007 |
| WO | 2008011131 | 1/2008 |
| WO | 2008089459 A1 | 7/2008 |
| WO | 2009001129 A1 | 12/2008 |
| WO | 2009024585 A2 | 2/2009 |
| WO | 2009037570 A2 | 3/2009 |
| WO | 2009134666 A1 | 11/2009 |
| WO | 2009137338 A1 | 11/2009 |
| WO | 2010036632 A1 | 4/2010 |
| WO | 2011049917 A1 | 4/2011 |
| WO | 2011056440 A1 | 5/2011 |
| WO | 2011071730 A1 | 6/2011 |
| WO | 2011137109 A1 | 11/2011 |
| WO | 2012087782 A1 | 6/2012 |

OTHER PUBLICATIONS

International Search Report and Written Opinion for PCT/US2011/065350 mailed Feb. 22, 2012.

International Search Report for PCT/US2009/041485 mailed Jun. 29, 2009.

International Search Report for PCT/US2009/057778 mailed Jan. 11, 2010.

International Search Report/Written Opinion for PCT/US2009/042455 mailed Jul. 13, 2009.

Gerard, C. et al., "Chemokines and Disease." Nature Immunology, 2001, vol. 2, pp. 108-115.

Horuk, R. "Chemokine Receptor Antagonists: Overcoming Developmental Hurdle." Nature Reviews Drug Discovery, 2009, vol. 8, pp. 23-33.

Pease, J. et al., "Chemokine Receptor Antagonists: Part 2." Expert Opin. Ther. Patents, 2009, vol. 19, pp. 199-221.

Alzheimer's Disease. Retrieved online Dec. 15, 2010. http:/www.cnn.com/Health/mentalhealt/alzheimers.

CAPLUS: 1990:478384, Bruneau, 1990.

CAPLUS: 2008:94643, Kitamura, 2008.

CAPLUS: 2009:583109, Doherty, 2009.

Carter, P.H. et al., "N-aryl pyrazoles,indazoles and azaindazoles as antagonists of CC chemokine receptor 1: patent cooperation treaty applications WO2010036632, WO2009134666 and WO2009137337". Expert Opinion Ther. Patents, 2010, 20(11), p. 1-10.

Cheng, J-F, et al., "CCR1 Antagonists". Molecular Diversity, Kluwer Academic Publishers, vol. 12, No. 1, Jun. 17, 2008, p. 17-23.

Conlon, K. et al., "Comparison of lymphokine secretion and mRNA expression in the CD45RA+ and CD45RO+ subsets of human peripheral blood CD4+ and CD8+ lympocytes". European Journal of Immunology, 1995, vol. 25, p. 644-648.

Finar, I.L. et al. The Beckmann Rearrangement of Some Pyrazolyl Oximes. Journal Chemical Soc. Sec. C, 1969, p. 1495-1499.

Gerard, C. et al., "Chemokines and disease". 2001 Nature Publishing Group, Chemokine Reviews, Nature Immunology, vol. 2, No. 2, Feb. 2001, p. 108-115.

Haringman, J.J. et al., "Chemokine blockade and chronic inflammatory disease: proof of concept in patients with rheumatoid arthritis". Ann Rheum Dis, 2003, 62, p. 715-721.

International Search Report/Written Opinion for PCT/US2010/053142 mailed Dec. 27, 2010.

Karpus, W. J. et al., "An Important Role for the Chemokine Macrophase Inflammatory Protein-1a in the Pathogenesis of the T Cell-Mediated Autoimmune Disease, Experimental Autoimmune Encephalomyelitis". The American Association of Immunologists, 1995, p. 5003-5010.

Koch, A. E., et al., "Macrophase Inflammatory Protein-1a. A Novel Chemotactic Cytokine for Macrophages in Rheumatoid Arthritis". The Journal of Clinical Investigation, Inc., vol. 93, Mar. 1994, p. 921-928.

Koch, A.E. et al., "Epithelial Neutrophil Activating Peptide-78: A Novel Chemotactic Cytokine for Neutrophils in Arthritis". The Journal of Clinical Investigations, Inc. vol. 94, Sep. 1994, p. 1012-1018.

Plater-Zyberk, C. et al., "Effect of a CC chemokine receptor antagonist on collagen induced arthritis in DBA/1 mice". Immunology Letters, 57, 1997, p. 117-120.

Revesz, L. et al., "Novel CCR1 antagonists with oral activity in the mouse collagen induced arthritis". Bioorganice and Medicinal Chemistry Letters, 2005, p. 1-5.

(56) References Cited

OTHER PUBLICATIONS

Trebst, C. et al., "CCR1+/CCR5+ Mononuclear Phagocytes Accumulate in the Central Nervous System on Patients with Multiple Sclerosis." American Journal of Pathology, vol. 159, No. 4, Nov. 2001, p. 1701-1710.

Volin, M.V. et al., "RANTES Expression and Contribution to Monocyte Chemotaxix in Arthritis". Clinical Immunology and Immunopathology, vol. 89, No. 1, Oct. 1998, Article II984590, p. 44-53.

Tak, P. et al., "Chemokine receptor CCR1 antagonist CCX354-C treatment for rheumatoid arthritis: CARAT-2, a randomised, placebo controlled clinical trial." 2012, Ann Rheum Dis., pp. 1-10.

INDAZOLE AND PYRAZOLOPYRIDINE COMPOUNDS AS CCR1 RECEPTOR ANTAGONISTS

APPLICATION DATA

This application claims benefit to U.S. provisional application Ser. No. 61/253,590 filed Oct. 21, 2009.

FIELD OF THE INVENTION

This invention relates to indazoles and pyrazolopyridines containing aryl- or heteroaryl-carbocyclylamine, as well as aryl- or heteroaryl-heterocyclylamine that are useful as antagonists of CCR1 activity and are thus useful for treating a variety of diseases and disorders that are mediated or sustained through the activity of CCR1 including autoimmune diseases, such as rheumatoid arthritis and multiple sclerosis. This invention also relates to pharmaceutical compositions comprising these compounds, methods of using these compounds in the treatment of various diseases and disorders, processes for preparing these compounds and intermediates useful in these processes.

BACKGROUND OF THE INVENTION

Chemotactic Cytokine Receptor 1 (CCR1) belongs to a large family (>20) of chemotactic cytokine (chemokine) receptors that interact with specific chemokines (>50) to mediate leukocyte trafficking, granule exocytosis, gene transcription, mitogenic effects and apoptosis. Chemokines are best known for their ability to mediate basal and inflammatory leukocyte trafficking. The binding of at least three chemokines (MIP-1 alpha/CCL3, MCP3/CCL7 and RANTES/CCL5) to CCR1 is responsible for the trafficking of monocytes, macrophages and TH1 cells to inflamed tissues of rheumatoid arthritis (RA) and multiple sclerosis (MS) patients (Trebst et al. (2001) *American J of Pathology* 159 p. 1701). Macrophage inflammatory protein 1 alpha (MIP-1 alpha), macrophage chemoattractant protein 3 (MCP-3) and regulated on activation, normal T-cell expressed and secreted (RANTES) are all found in the CNS of MS patients, while MIP-1 alpha and RANTES are found in the CNS in the experimental autoimmune encephalomyelitis (EAE) model of MS (Review: Gerard and Rollins (2001) *Nature Immunology*). Macrophages and Th1 cells in the inflamed synovia of RA patients are major producers of MIP-1 alpha and RANTES, which continuously recruit leukocytes to the synovial tissues of RA patients to propagate chronic inflammation (Volin et al. (1998) *Clin. Immunol. Immunopathology*; Koch et al. (1994) *J. Clin. Investigation*; Conlon et al. (1995) *Eur. J. Immunology*). Antagonizing the interactions between CCR1 and its chemokine ligands is hypothesized to block chemotaxis of monocytes, macrophages and Th1 cells to inflamed tissues and thereby ameliorate the chronic inflammation associated with autoimmune diseases such as RA and MS.

Evidence for the role of CCR1 in the development and progression of chronic inflammation associated with experimental autoimmune encephalitis (EAE), a model of multiple sclerosis, is based on both genetic deletion and small molecule antagonists of CCR1. CCR1 deficient mice were shown to exhibit reduced susceptibility (55% vs. 100%) and reduced severity (1.2 vs. 2.5) of active EAE (Rottman et al. (2000) *Eur. J. Immunology*). Furthermore, administration of small molecule antagonist of CCR1, with moderate affinity ($K_i$=120 nM) for rat CCR1, was shown to delay the onset and reduce the severity of EAE when administered intravenously (Liang et al. (2000) *J. Biol. Chemistry*). Treatment of mice with antibodies specific for the CCR1 ligand MIP-1 alpha have also been shown to be effective in preventing development of acute and relapsing EAE by reducing the numbers of T cells and macrophages recruited to the CNS (Karpus et al. (1995) *J. Immunology*; Karpus and Kennedy (1997) *J. Leukocyte Biology*). Thus, at least one CCR1 ligand has been demonstrated to recruit leukocytes to the CNS and propagate chronic inflammation in EAE, providing further in vivo validation for the role of CCR1 in EAE and MS.

In vivo validation of CCR1 in the development and propagation of chronic inflammation associated with RA is also significant. For example, administration of a CCR1 antagonist in the collagen induced arthritis model (CIA) in DBA/1 mice has been shown to be effective in reducing synovial inflammation and joint destruction (Plater-Zyberk et al. (1997) *Immunology Letters*). Another publication described potent antagonists of murine CCR1 that reduced severity (58%) in LPS-accelerated collagen-induced arthritis (CIA), when administered orally (*Biorganic and Medicinal Chemistry Letters* 15, 2005, 5160-5164). Published results from a Phase Ib clinical trial with an oral CCR1 antagonist demonstrated a trend toward clinical improvement in the absence of adverse side effects (Haringman et al. (2003) *Ann. Rheum. Dis.*). One third of the patients achieved a 20% improvement in rheumatoid arthritis signs and symptoms (ACR20) on day 18 and CCR1 positive cells were reduced by 70% in the synovia of the treated patients, with significant reduction in specific cell types including 50% reduction in $CD4^+$ T cells, 50% reduction in $CD8^+$ T cells and 34% reduction in macrophages.

Studies such as those cited above support a role for CCR1 in MS and RA and provide a therapeutic rationale for the development of CCR1 antagonists.

BRIEF SUMMARY OF THE INVENTION

The present invention provides novel compounds which block the interaction of CCR1 and its ligands and are thus useful for treating a variety of diseases and disorders that are mediated or sustained through the activity of CCR1 including autoimmune diseases, such as rheumatoid arthritis and multiple sclerosis. This invention also relates to pharmaceutical compositions comprising these compounds, methods of using these compounds in the treatment of various diseases and disorders, processes for preparing these compounds and intermediates useful in these processes.

DETAILED DESCRIPTION OF THE INVENTION

In its broadest generic aspect the invention provides a compound of the formula (I)

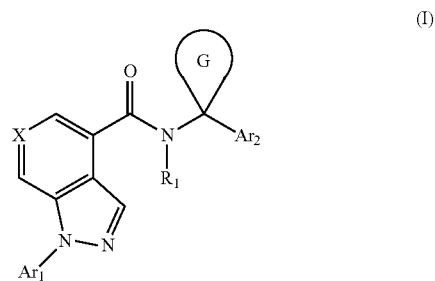

wherein

X is nitrogen or, C—$R_2$;

$Ar_1$ is carbocycle, heteroaryl or heterocyclyl each optionally substituted by one to three $R_a$;

$Ar_2$ is carbocycle, heteroaryl or heterocyclyl, each optionally substituted by one to three $R_b$;

Cyclic G is carbocycle, or heterocyclyl each optionally substituted by one to two $R_g$;

$R_1$ is hydrogen, $C_{1-6}$ alkyl or $C_{1-6}$ alkoxy$C_{1-6}$ alkyl;

$R_2$ is hydrogen or $R_a$;

$R_a$ is $C_{1-6}$ alkyl, $C_{3-10}$ cycloalkyl, $C_{1-6}$ alkoxy, $C_{1-6}$ alkylthio, $C_{1-6}$ alkylsulfonyl, $C_{1-6}$ alkoxycarbonyl, amino, mono- or di-$C_{1-6}$ alkylamino, $C_{3-6}$ cycloalkylamino, $C_{1-6}$ alkylaminocarbonyl, $C_{1-6}$ acyl, $C_{1-6}$ acylamino, $C_{1-6}$ dialkylaminocarbonyl, hydroxyl, halogen, cyano, nitro, oxo, $R_3$—S(O)$_m$—NH—, $R_3$—NH—S(O)$_m$—, aryl or carboxyl;

$R_b$ is hydroxyl, carboxyl, halogen, —(CH$_2$)$_n$—CN, —(CH$_2$)$_n$—CO$_2$C$_{1-6}$alkyl, nitro, —SO$_3$H, $C_{1-6}$ alkyl, $C_{2-6}$ alkenyl, $C_{2-6}$ alkynyl, $C_{3-10}$ cycloalkyl, $C_{1-6}$ alkoxy, $C_{1-6}$alkylC(O)—, —(CH$_2$)$_n$—NR$_c$R$_d$, $R_3$—S(O)$_m$(CH$_2$)$_{0-1}$—, $R_3$—S(O)$_m$—NR$_e$—, $R_3$—NR$_e$—S(O)$_m$(CH$_2$)$_{0-1}$—, —NR$_f$—C(O)—R$_e$, —(CH$_2$)$_y$—C(O)—(CH$_2$)$_n$—NR$_c$R$_d$, heterocyclyl, aryl or heteroaryl, each $R_b$ where possible is optionally halogenated or substituted with 1 to 3 $C_{1-6}$ alkyl, hydroxyl, $C_{1-6}$ acyl, $C_{1-6}$ alkoxycarbonyl, $C_{1-6}$ alkyl-S(O)$_m$—, aryl or carboxyl;

each $R_c$, $R_d$ are independently hydrogen, $C_{1-6}$ alkyl, $C_{1-6}$ acyl, $C_{3-10}$ cycloalkyl, $C_{1-6}$ alkoxy, hydroxy$C_{1-6}$ alkyl, cyano-$C_{1-6}$ alkyl, $C_{1-6}$ alkylC$_{1-6}$ alkoxy, $C_{1-6}$ alkylsulfonyl, $C_{1-6}$ alkoxycarbonylC$_{0-3}$alkyl, $C_{1-6}$ alkoxycarbonylC$_{3-10}$cycloalkyl, —(CH$_2$)$_n$—C(O)—NR$_e$R$_f$ or —(CH$_2$)$_n$—NR$_e$R$_f$;

each $R_e$, $R_f$ are independently hydrogen, $C_{1-6}$ alkyl, $C_{3-10}$ cycloalkyl, $C_{1-6}$ alkoxy, $C_{1-6}$ alkoxyC$_{1-6}$alkyl, mono- or diC$_{1-6}$ alkylaminoC$_{1-6}$alkyl, hydroxyC$_{1-6}$ alkyl or $C_{1-6}$ acyl;

$R_g$ is $C_{1-6}$ alkyl, wherein the $C_{1-6}$ alkyl is optionally partially or fully halogenated, $C_{2-6}$ alkenyl, carbocycle, $C_{1-6}$ alkoxy, carbocyclyl-$C_{1-6}$ alkoxy, carbocyclyl-$C_{1-6}$ alkyl, hydroxyC$_{1-6}$ alkyl, hydroxyl, —(CH$_2$)$_n$—CO$_2$C$_{1-6}$ alkyl or oxo;

$R_3$ is hydrogen, $C_{1-6}$ alkyl, $C_{3-6}$cycloalkyl, heterocyclyl (CH$_2$)$_{0-1}$, mono- or di-$C_{1-6}$ alkylamino, mono- or di-$_{1-6}$alkylamino(CH$_2$)$_{2-3}$N(R$_e$)—, aryl or heteroaryl each optionally substituted with 1 to 3 $C_{1-6}$ alkyl, $C_{3-6}$cycloalkyl, $C_{1-6}$alkoxy, halogen, hydroxyl, oxo, carboxyl, —C(O)NR$_e$R$_f$, amino, mono- or di-$C_{1-6}$ alkylamino, $C_{1-6}$ alkoxycarbonyl or $C_{1-6}$ acylamino;

each n, y are independently 0-3;

each m is independently 0-2;

or a pharmaceutically acceptable salt thereof.

In another embodiment of the invention there is provided a compound of the formula (I) as provided immediately above, and wherein Cyclic G is carbocycle-optionally substituted by one to two $R_g$;

In another embodiment of the invention there is provided a compound of the formula (I) as provided immediately above, and wherein X is nitrogen;

$Ar_1$ is carbocycle optionally substituted by one to three $R_a$;

$Ar_2$ is carbocycle or heteroaryl, each optionally substituted by one to three $R_b$;

$R_1$ is hydrogen;

$R_a$ is $C_{1-3}$alkyl, $C_{1-3}$ alkoxy, di-$C_{1-6}$ alkylamino, methylsulfonyl, halogen, or cyano;

$R_b$ is hydroxyl, carboxyl, halogen, —(CH$_2$)$_n$—CN, —(CH$_2$)$_n$—CO$_2$C$_{1-6}$alkyl, nitro, —SO$_3$H, $C_{1-6}$ alkyl, $C_{2-6}$ alkenyl, $C_{2-6}$ alkynyl, $C_{3-10}$cycloalkyl, $C_{1-6}$alkoxy, $C_{1-6}$alkylC(O)—, —(CH$_2$)$_n$—NR$_c$R$_d$, $R_3$—S(O)$_m$(CH$_2$)$_{0-1}$—, $R_3$—S(O)$_m$—NR$_e$—, $R_3$—NR$_e$—S(O)$_m$(CH$_2$)$_{0-1}$—, —NR$_f$—C(O)—R$_e$, —(CH$_2$)$_y$—C(O)—(CH$_2$)$_n$—NR$_c$R$_d$, heterocyclyl, aryl or heteroaryl, each $R_b$ where possible is optionally halogenated or substituted with 1 to 3 $C_{1-6}$ alkyl, $C_{1-6}$ acyl, $C_{1-6}$ alkoxycarbonyl, $C_{1-6}$ alkyl-S(O)$_m$—, aryl or carboxyl;

$R_3$ is hydrogen, $C_{1-6}$ alkyl, $C_{3-6}$cycloalkyl, heterocyclyl (CH$_2$)$_{0-1}$, mono- or di-$C_{1-6}$ alkylamino, mono- or di-$_{1-6}$alkylamino(CH$_2$)$_{2-3}$N(C$_{1-6}$alkyl)-, aryl or heteroaryl each optionally substituted with 1 to 2 $C_{1-6}$ alkyl, $C_{3-6}$cycloalkyl, $C_{1-6}$alkoxy, halogen, hydroxyl, oxo, carboxyl, —C(O)NR$_e$R$_f$, amino, mono- or di-$C_{1-6}$ alkylamino, $C_{1-6}$ alkoxycarbonyl or $C_{1-6}$ acylamino.

In a further embodiment of the invention there is provided a compound of the formula (I) as provided immediately above, and wherein $Ar_1$ is phenyl is substituted by one to two $R_a$;

$Ar_2$ is phenyl, thiadiazolyl, oxadiazolyl, pyrimidinyl, furanyl, thiazolyl or pyridyl, each optionally substituted by one to two $R_b$;

Cyclic G is cyclopropyl or cyclobutyl;

$R_a$ is halogen;

$R_b$ is hydroxyl, carboxyl, halogen, —CF$_3$, —CN, —SO$_3$H, $C_{1-3}$ alkyl, $C_{3-6}$ cycloalkyl $C_{1-3}$ alkoxy, —(CH$_2$)$_n$—CO$_2$C$_{1-3}$ alkyl, —(CH$_2$)$_n$—NR$_c$R$_d$, $R_3$—S(O)$_m$(CH$_2$)$_{0-1}$—, $R_3$—S(O)$_2$—NR$_3$—, $R_3$—NR$_e$—S(O)$_2$(CH$_2$)$_{0-1}$—, —NR$_f$—C(O)—R$_e$, —(CH$_2$)$_y$—C(O)—NR$_c$R$_d$, or morpholinyl;

each $R_c$, $R_d$ are independently hydrogen, $C_{1-3}$ alkyl, $C_{1-3}$ acyl, cyano-$C_{1-3}$ alkyl, $C_{1-3}$ alkoxycarbonylC$_{0-3}$alkyl, $C_{1-3}$ alkoxycarbonylC$_{3-6}$cycloalkyl, or —(CH$_2$)$_n$—C(O)—NR$_e$R$_f$;

each $R_e$, $R_f$ are independently hydrogen or $C_{1-3}$ alkyl;

$R_3$ is hydrogen or $C_{1-6}$alkyl, each optionally substituted with one to two $C_{1-6}$alkoxy, or In a another embodiment of the invention there is provided a compound of the formula (I) as provided immediately above, and wherein Cyclic G is cyclopropyl;

$R_a$ is —F or —Cl;

$R_b$ is —CH$_3$, carboxyl, —F, —Cl, —Br, —I, —CF$_3$, cyclopropyl, —OCH$_3$, —CO$_2$Me, —NR$_c$R$_d$, —CH$_2$—NR$_c$R$_d$, $R_3$—S(O)$_m$—, $R_3$—S(O)$_2$—NR$_e$—, $R_3$—NR$_e$—S(O)$_2$—, —NR$_f$—C(O)—R$_e$, —C(O)NR$_c$R$_d$ or morpholinyl;

each $R_c$, $R_d$ are independently hydrogen, —CH$_3$, —C(O)CH$_3$, —CH$_2$CN, $C_{1-4}$ alkoxycarbonyl, methoxycarbonyl-$C_{1-2}$ alkyl-, methoxycarbonyl-$C_3$cycloalkyl- or —(CH$_2$)—C(O)—NR$_e$R$_f$;

each $R_e$, $R_f$ are independently hydrogen or —CH$_3$;

$R_3$ is hydrogen or $C_{1-4}$alkyl each optionally substituted with one to two —OCH$_3$ or oxo.

In another embodiment of the invention there is provided a compound of the formula (I) as provided in the broadest generic embodiment, and wherein X is C—$R_2$;

$Ar_1$ is carbocycle optionally substituted by one to three $R_a$;

$Ar_2$ is carbocycle or heteroaryl, each optionally substituted by one to three $R_b$;

Cyclic G is carbocycle optionally substituted by one to two $R_g$;

$R_1$ is hydrogen;

$R_2$ is hydrogen or $R_a$;

$R_a$ is $C_{1-3}$alkyl, $C_{1-3}$ alkoxy, di-$C_{1-6}$ alkylamino, methylsulfonyl, halogen, or cyano;

$R_b$ is hydroxyl, carboxyl, halogen, —(CH$_2$)$_n$—CN, —(CH$_2$)$_n$—CO$_2$C$_{1-6}$alkyl, nitro, —SO$_3$H, $C_{1-6}$ alkyl, $C_{2-6}$ alkenyl, $C_{2-6}$ alkynyl, $C_{3-10}$cycloalkyl, $C_{1-6}$alkoxy, $C_{1-6}$alkylC(O)—, —(CH$_2$)$_n$—NR$_c$R$_d$, R$_3$—S(O)$_m$(CH$_2$)$_{0-1}$—, R$_3$—S(O)$_m$—NR$_e$—, R$_3$—NR$_e$—S(O)$_m$(CH$_2$)$_{0-1}$—, —NR$_f$—C(O)—R$_e$, —(CH$_2$)$_y$—C(O)—(CH$_2$)$_n$—NR$_c$R$_d$, heterocyclyl, aryl or heteroaryl, each R$_b$ where possible is optionally halogenated or substituted with 1 to 3 C$_{1-6}$ alkyl, C$_{1-6}$ acyl, C$_{1-6}$ alkoxycarbonyl, C$_{1-6}$ alkyl-S(O)$_m$—, aryl or carboxyl;

each R$_c$, R$_d$ are independently hydrogen, C$_{1-6}$ alkyl, C$_{1-6}$ acyl, C$_{3-10}$ cycloalkyl, C$_{1-6}$ alkoxy, hydroxyC$_{1-6}$ alkyl, cyanoC$_{1-6}$ alkyl, C$_{1-6}$ alkylC$_{1-6}$ alkoxy, C$_{1-6}$ alkylsulfonyl, C$_{1-6}$ alkoxycarbonylC$_{0-3}$alkyl, C$_{1-6}$ alkoxycarbonylC$_{3-10}$cyclo alkyl, —(CH$_2$)$_n$—C(O)—NR$_e$R$_f$ or —(CH$_2$)$_n$—NR$_e$R$_f$;

each R$_e$, R$_f$ are independently hydrogen, C$_{1-6}$ alkyl, C$_{3-10}$ cycloalkyl, C$_{1-6}$ alkoxy, C$_{1-6}$ alkoxyC$_{1-6}$alkyl, mono- or diC$_{1-6}$ alkylaminoC$_{1-6}$ alkyl, hydroxyC$_{1-6}$ alkyl or C$_{1-6}$ acyl;

R$_3$ is hydrogen, C$_{1-6}$ alkyl, C$_{3-6}$cycloalkyl, heterocyclyl(CH$_2$)$_{0-1}$, mono- or di-C$_{1-6}$ alkylamino, mono- or di-$_{1-6}$alkylamino(CH$_2$)$_{2-3}$N(C$_{1-6}$alkyl)-, aryl or heteroaryl each optionally substituted with 1 to 2 C$_{1-6}$ alkyl, C$_{3-6}$cycloalkyl, C$_{1-6}$alkoxy, halogen, hydroxyl, oxo, carboxyl, —C(O)NR$_e$R$_f$, amino, mono- or di-C$_{1-6}$ alkylamino, C$_{1-6}$ alkoxycarbonyl or C$_{1-6}$ acylamino.

In a further embodiment of the invention there is provided a compound of the formula (I) as provided immediately above, and wherein Ar$_1$ is phenyl is substituted by one to two R$_a$;

Ar$_2$ is phenyl, thiadiazolyl, oxadiazolyl, pyrimidinyl, furanyl, thiazolyl or pyridyl, each optionally substituted by one to two R$_b$;

Cyclic G is cyclopropyl or cyclobutyl;

R$_a$ is C$_{1-3}$alkyl, methylsulfonyl, halogen, or cyano;

R$_b$ is hydroxyl, carboxyl, halogen, —CF$_3$, —CN, —SO$_3$H, C$_{1-3}$ alkyl, C$_{3-6}$ cycloalkyl C$_{1-3}$ alkoxy, —(CH$_2$)$_n$—CO$_2$C$_{1-3}$ alkyl, —(CH$_2$)$_n$—NR$_c$R$_d$, R$_3$—S(O)$_m$(CH$_2$)$_{0-1}$—, R$_3$—S(O)$_2$—NR$_e$—, R$_3$—NR$_e$—S(O)$_2$(CH$_2$)$_{0-1}$—, —NR$_f$—C(O)—R$_e$, —(CH$_2$)$_y$—C(O)—NR$_c$R$_d$, or morpholinyl;

each R$_c$, R$_d$ are independently hydrogen, C$_{1-3}$ alkyl, C$_{1-3}$ acyl, cyano-C$_{1-3}$ alkyl, C$_{1-3}$ alkoxycarbonylC$_{0-3}$alkyl, C$_{1-3}$ alkoxycarbonylC$_{3-6}$cycloalkyl, or —(CH$_2$)$_n$—C(O)—NR$_e$R$_f$;

each R$_e$, R$_f$ are independently hydrogen or C$_{1-3}$ alkyl;

R$_3$ is hydrogen or C$_{1-6}$alkyl, each optionally substituted with one to two C$_{1-6}$alkoxy, or In a another embodiment of the invention there is provided a compound of the formula (I) as provided immediately above, and wherein Cyclic G is cyclopropyl;

R$_a$ is —F or —Cl, methyl, methylsulfonyl or cyano;

R$_b$ is —CH$_3$, carboxyl, —F, —Cl, —Br, —I, —CF$_3$, cyclopropyl, —OCH$_3$, —CO$_2$Me, —NR$_c$R$_d$, —(CH$_2$)—NR$_c$R$_d$, R$_3$—S(O)$_m$—, R$_3$—S(O)$_2$—NR$_e$—, R$_3$—NR$_e$—S(O)$_2$—, —NR$_f$—C(O)—R$_e$, —C(O)NR$_c$R$_d$ or morpholinyl;

each R$_c$, R$_d$ are independently hydrogen, —CH$_3$, —C(O)CH$_3$, —CH$_2$CN, C$_{1-4}$ alkoxycarbonyl, methoxycarbonyl-C$_{1-2}$ alkyl-, methoxycarbonyl-C$_3$cycloalkyl- or —(CH$_2$)—C(O)—NR$_e$R$_f$;

each R$_e$, R$_f$ are independently hydrogen or —CH$_3$;

R$_3$ is hydrogen or C$_{1-4}$alkyl each optionally substituted with one to two —OCH$_3$ or oxo.

In a another embodiment of the invention there is provided a compound of the formula (I) according to any one of the embodiments where applicable hereinabove and wherein Cyclic G is cyclopropyl or cyclobutyl.

In a another embodiment of the invention there is provided a compound of the formula (I) as provided immediately above, and wherein Cyclic G is cyclopropyl.

In a another embodiment of the invention there is provided a compound of the formula (I) according to any one of the embodiments where applicable hereinabove and wherein R$_c$, is hydrogen or C$_{1-6}$ alkyl, and R$_d$ is C$_{1-6}$ acyl, cyano-C$_{1-6}$alkyl-, C$_{1-6}$alkoxycarbonyl-C$_{0-3}$alkyl-, C$_{1-6}$ alkoxycarbonylC$_{3-10}$cyclo alkyl, or —(CH$_2$)$_n$—C(O)—NR$_e$R$_f$;

each R$_e$, R$_f$ are independently hydrogen, C$_{1-6}$ alkyl.

In another embodiment of the invention there is provided a compound of the formula (I) according to any one of the embodiments where applicable hereinabove and wherein Ar$_2$ is phenyl, pyrimidinyl, furanyl, thiazolyl or pyridyl, each optionally substituted by one or two R$_b$;

R$_b$ is —SO$_2$Me, —I, —Br, —Cl, —CF$_3$, —OMe, —NMe$_2$, —CONHMe, —SO$_2$NH$_2$.

In a another embodiment of the invention there is provided a compound of the formula (I) according to any one of the embodiments where applicable hereinabove and wherein Ar$_2$ is

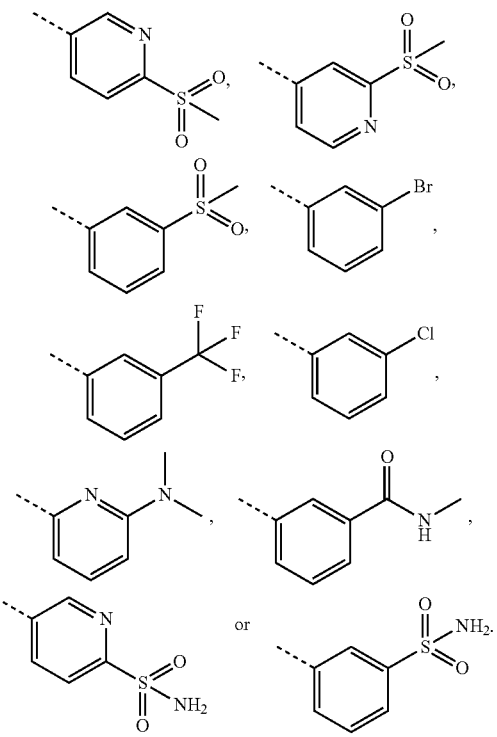

In a another embodiment of the invention there is provided a compound of the formula (I) according to any one of the embodiments where applicable hereinabove and wherein R$_g$ is i) C$_{1-2}$ alkyl, —CF$_3$, C$_2$ alkenyl, phenyl, C$_{1-4}$ alkoxy, carbocyclylCH$_2$O—, carbocyclylCH$_2$— —CH$_2$OH, hydroxyl, —CO$_2$C$_{1-4}$ alkyl or oxo;

or ii) is methyl, vinyl, —CF$_3$, phenyl, —CH$_2$OH, or hydroxyl.

The following are representative compounds of the invention which can be made by the general synthetic schemes, the examples, and known methods in the art.

TABLE I

| Structure | Name | HPLC-MS Data[a] | |
|---|---|---|---|
| | | Observed Mass[b] | rt (min) |
| 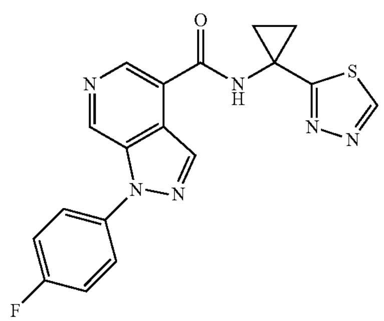 [SMILES: O=C(NC1(c2nncs2)CC1)c1cncc2c1cnn2-c1ccc(F)cc1] | 1-(4-Fluoro-phenyl)-1H-pyrazolo[3,4-c]pyridine-4-carboxylic acid (1-1,3,4-thiadiazol-2-yl-cyclopropyl)-amide | 381.60 | 1.29 |
| 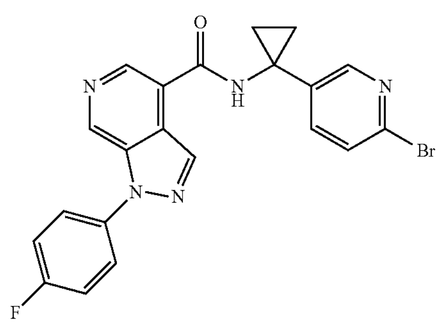 [SMILES: O=C(NC1(c2ccc(Br)nc2)CC1)c1cncc2c1cnn2-c1ccc(F)cc1] | 1-(4-Fluoro-phenyl)-1H-pyrazolo[3,4-c]pyridine-4-carboxylic acid [1-(6-bromo-pyridin-3-yl)-cyclopropyl]-amide | 452.60; 454.60 | 1.75 |
| 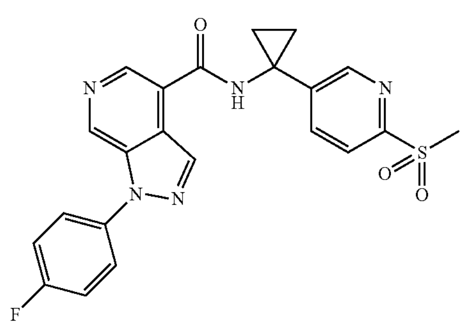 [SMILES: CS(=O)(=O)c1ccc(C2(NC(=O)c3cncc4c3cnn4-c3ccc(F)cc3)CC2)cn1] | 1-(4-Fluoro-phenyl)-1H-pyrazolo[3,4-c]pyridine-4-carboxylic acid [1-(6-methanesulfonyl-pyridin-3-yl)-cyclopropyl]-amide | 452.67 | 1.39 |
| 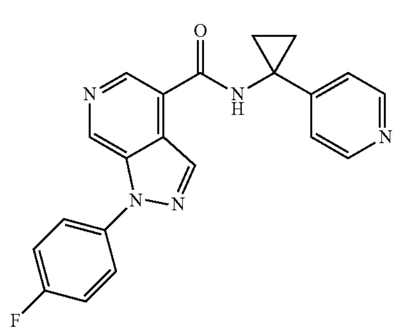 [SMILES: O=C(NC1(c2ccncc2)CC1)c1cncc2c1cnn2-c1ccc(F)cc1] | 1-(4-Fluoro-phenyl)-1H-pyrazolo[3,4-c]pyridine-4-carboxylic acid (1-pyridin-4-yl-cyclopropyl)-amide | 374.71 | 1.15 |

TABLE I-continued

| Structure | Name | HPLC-MS Data[a] | |
|---|---|---|---|
| | | Observed Mass [b] | rt (min) |
| 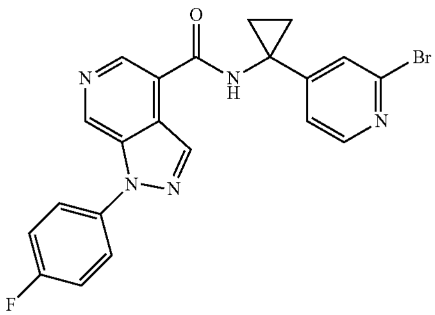 [SMILES: O=C(NC1(c2ccnc(Br)c2)CC1)c1cncc2c1cnn2-c1ccc(F)cc1] | 1-(4-Fluoro-phenyl)-1H-pyrazolo[3,4-c]pyridine-4-carboxylic acid [1-(2-bromo-pyridin-4-yl)-cyclopropyl]-amide | 452.66; 454.64 | 1.53 |
| 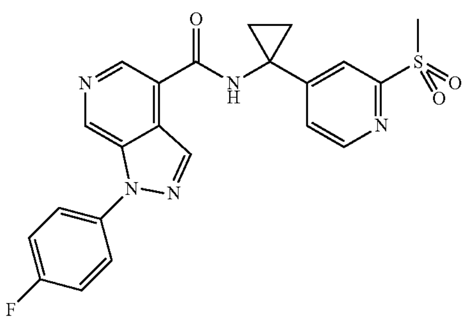 [SMILES: CS(=O)(=O)c1cc(C2(NC(=O)c3cncc4c3cnn4-c3ccc(F)cc3)CC2)ccn1] | 1-(4-Fluoro-phenyl)-1H-pyrazolo[3,4-c]pyridine-4-carboxylic acid [1-(2-methanesulfonyl-pyridin-4-yl)-cyclopropyl]-amide | 452.68 | 1.38 |
| 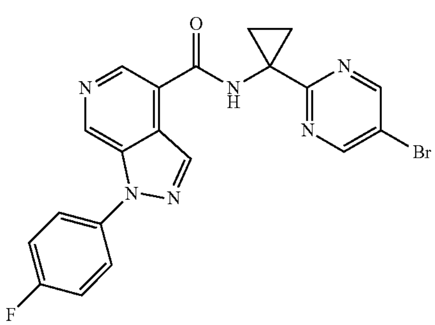 [SMILES: O=C(NC1(c2ncc(Br)cn2)CC1)c1cncc2c1cnn2-c1ccc(F)cc1] | 1-(4-Fluoro-phenyl)-1H-pyrazolo[3,4-c]pyridine-4-carboxylic acid [1-(5-bromo-pyrimidin-2-yl)-cyclopropyl]-amide | 453.21; 455.37 | 1.54 |
| 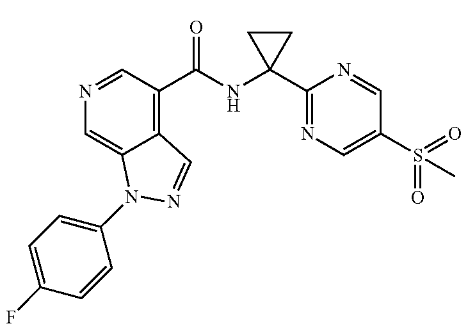 [SMILES: CS(=O)(=O)c1cnc(C2(NC(=O)c3cncc4c3cnn4-c3ccc(F)cc3)CC2)nc1] | 1-(4-Fluoro-phenyl)-1H-pyrazolo[3,4-c]pyridine-4-carboxylic acid [1-(5-methanesulfonyl-pyrimidin-2-yl)-cyclopropyl]-amide | 453.71 | 1.39 |

TABLE I-continued

| Structure | Name | HPLC-MS Data[a] Observed Mass[b] | rt (min) |
|---|---|---|---|
| 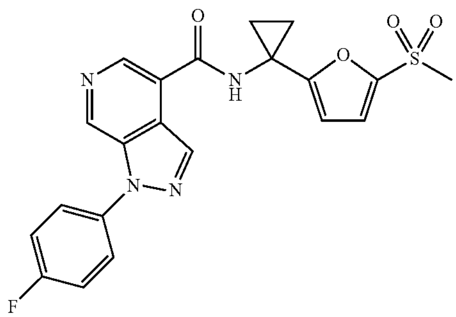 [SMILES: CS(=O)(=O)c1ccc(C2(NC(=O)c3cncc4c3cnn4-c3ccc(F)cc3)CC2)o1] | 1-(4-Fluoro-phenyl)-1H-pyrazolo[3,4-c]pyridine-4-carboxylic acid [1-(5-methanesulfonyl-furan-2-yl)-cyclopropyl]-amide | 441.13 | 1.46 |
| 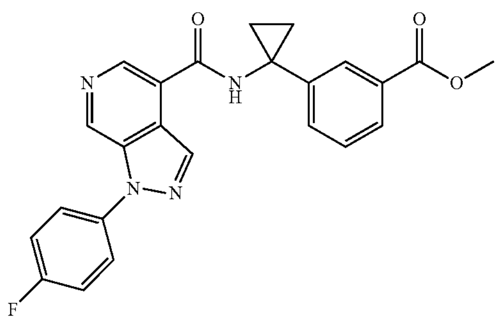 [SMILES: COC(=O)c1cccc(C2(NC(=O)c3cncc4c3cnn4-c3ccc(F)cc3)CC2)c1] | 3-(1-{[1-(4-Fluoro-phenyl)-1H-pyrazolo[3,4-c]pyridine-4-carbonyl]-amino}-cyclopropyl)-benzoic acid methyl ester | 431.22 | 1.61 |
| 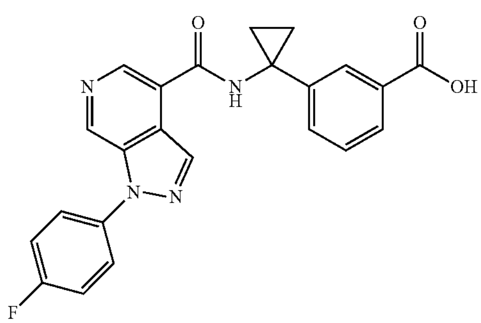 [SMILES: O=C(O)c1cccc(C2(NC(=O)c3cncc4c3cnn4-c3ccc(F)cc3)CC2)c1] | 3-(1-{[1-(4-Fluoro-phenyl)-1H-pyrazolo[3,4-c]pyridine-4-carbonyl]-amino}-cyclopropyl)-benzoic acid | 417.20 | 1.43 |
| 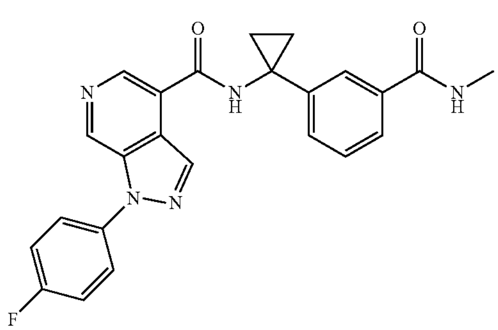 [SMILES: CNC(=O)c1cccc(C2(NC(=O)c3cncc4c3cnn4-c3ccc(F)cc3)CC2)c1] | 1-(4-Fluoro-phenyl)-1H-pyrazolo[3,4-c]pyridine-4-carboxylic acid [1-(3-methylcarbamoyl-phenyl)-cyclopropyl]-amide | 430.19 | 1.37 |

TABLE I-continued

| Structure | Name | HPLC-MS Data[a] | |
|---|---|---|---|
| | | Observed Mass[b] | rt (min) |
| 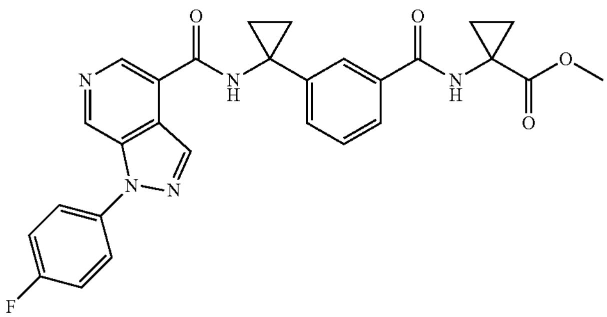 [SMILES: COC(=O)C1(NC(=O)c2cccc(C3(NC(=O)c4cncc5c4cnn5-c4ccc(F)cc4)CC3)c2)CC1] | 1-[3-(1-{[1-(4-Fluoro-phenyl)-1H-pyrazolo[3,4-c]pyridine-4-carbonyl]-amino}-cyclopropyl)-benzoylamino]-cyclopropanecarboxylic acid methyl ester | 514.26 | 1.44 |
| 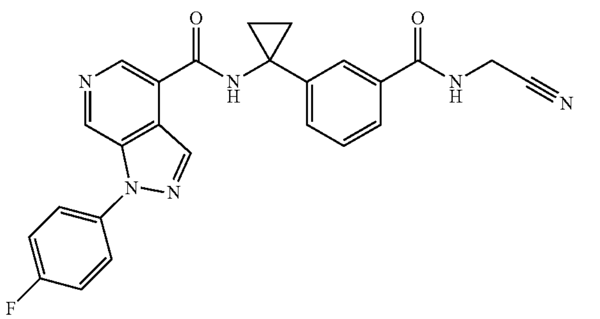 [SMILES: N#CCNC(=O)c1cccc(C2(NC(=O)c3cncc4c3cnn4-c3ccc(F)cc3)CC2)c1] | 1-(4-Fluoro-phenyl)-1H-pyrazolo[3,4-c]pyridine-4-carboxylic acid {1-[3-(cyanomethyl-carbamoyl)-phenyl]-cyclopropyl}-amide | 455.17 | 1.42 |
| 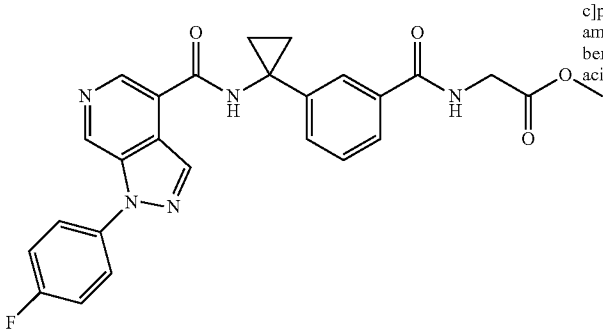 | [3-(1-{[1-(4-Fluoro-phenyl)-1H-pyrazolo[3,4-c]pyridine-4-carbonyl]-amino}-cyclopropyl)-benzoylamino]-acetic acid methyl ester | 488.20 | 1.41 |
| 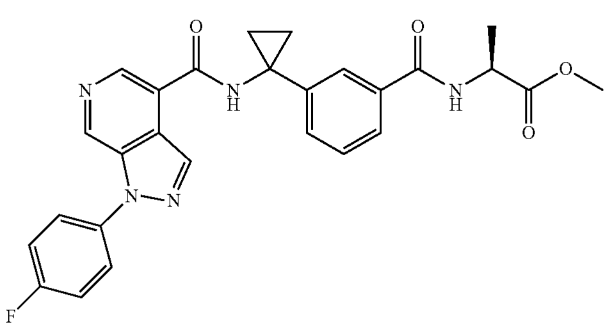 [SMILES: COC(=O)[C@H](C)NC(=O)c1cccc(C2(NC(=O)c3cncc4c3cnn4-c3ccc(F)cc3)CC2)c1] | (S)-2-[3-(1-{[1-(4-Fluoro-phenyl)-1H-pyrazolo[3,4-c]pyridine-4-carbonyl]-amino}-cyclopropyl)-benzoylamino]-propionic acid methyl ester | 502.27 | 1.47 |

TABLE I-continued

| Structure | Name | HPLC-MS Data[a] | |
|---|---|---|---|
| | | Observed Mass [b] | rt (min) |
| 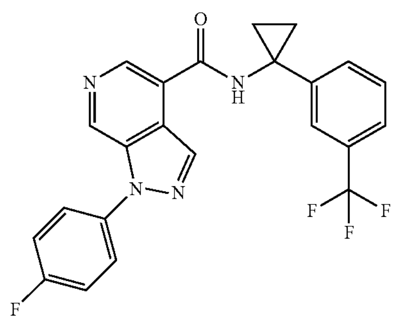 [SMILES: O=C(NC1(c2cccc(C(F)(F)F)c2)CC1)c1cncc2c1cnn2-c1ccc(F)cc1] | 1-(4-Fluoro-phenyl)-1H-pyrazolo[3,4-c]pyridine-4-carboxylic acid [1-(3-trifluoromethyl-phenyl)-cyclopropyl]-amide | 441.07 | 1.07 |
| 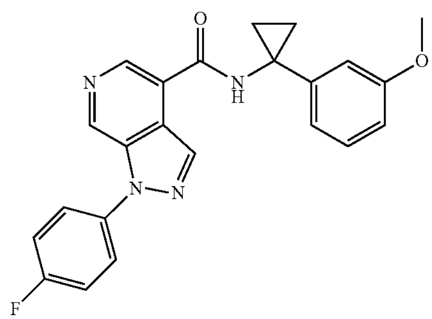 [SMILES: COc1cccc(C2(NC(=O)c3cncc4c3cnn4-c3ccc(F)cc3)CC2)c1] | 1-(4-Fluoro-phenyl)-1H-pyrazolo[3,4-c]pyridine-4-carboxylic acid [1-(3-methoxy-phenyl)cyclopropyl]-amide | 404.03 | 0.95 |
| 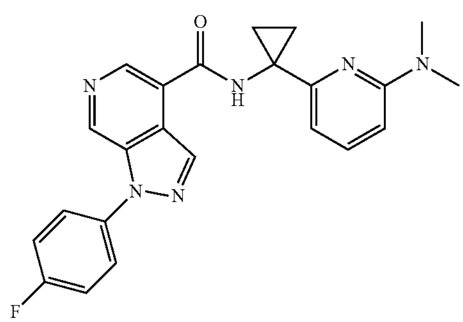 [SMILES: CN(C)c1cccc(C2(NC(=O)c3cncc4c3cnn4-c3ccc(F)cc3)CC2)n1] | 1-(4-Fluoro-phenyl)-1H-pyrazolo[3,4-c]pyridine-4-carboxylic acid [1-(6-dimethylamino-pyridin-2-yl)-cyclopropyl]-amide | 417.27 | 0.7 |
| 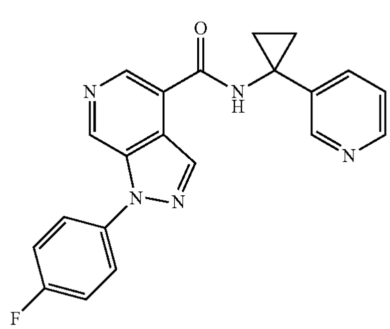 [SMILES: O=C(NC1(c2cccnc2)CC1)c1cncc2c1cnn2-c1ccc(F)cc1] | 1-(4-Fluoro-phenyl)-1H-pyrazolo[3,4-c]pyridine-4-carboxylic acid (1-pyridin-3-yl-cyclopropyl)-amide | 374.14 | 0.56 |

TABLE I-continued

| Structure | Name | HPLC-MS Data[a] | |
|---|---|---|---|
| | | Observed Mass[b] | rt (min) |
| 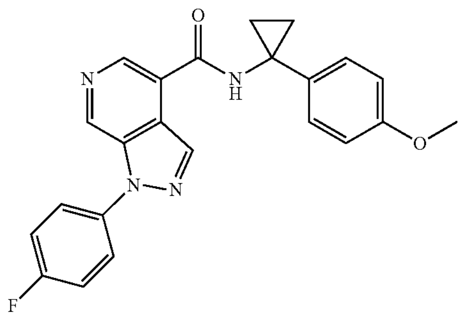 [SMILES: COc1ccc(C2(NC(=O)c3cncc4c3cnn4-c3ccc(F)cc3)CC2)cc1] | 1-(4-Fluoro-phenyl)-1H-pyrazolo[3,4-c]pyridine-4-carboxylic acid [1-(4-methoxy-phenyl)-cyclopropyl]-amide | 403.99 | 0.94 |
| 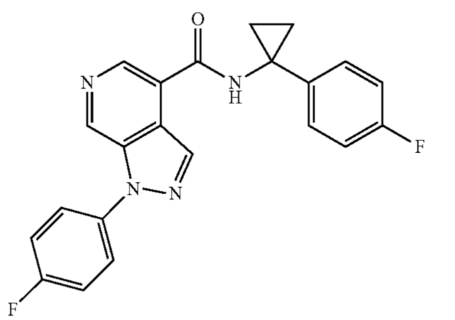 [SMILES: O=C(NC1(c2ccc(F)cc2)CC1)c1cncc2c1cnn2-c1ccc(F)cc1] | 1-(4-Fluoro-phenyl)-1H-pyrazolo[3,4-c]pyridine-4-carboxylic acid [1-(4-fluoro-phenyl)-cyclopropyl]-amide | 391.02 | 0.97 |
| 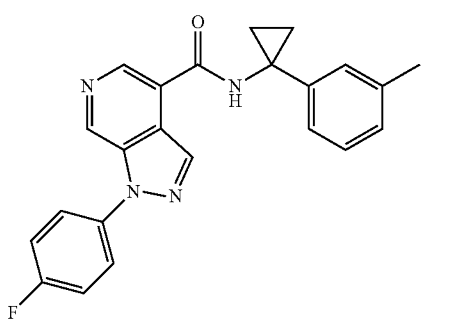 [SMILES: Cc1cccc(C2(NC(=O)c3cncc4c3cnn4-c3ccc(F)cc3)CC2)c1] | 1-(4-Fluoro-phenyl)-1H-pyrazolo[3,4-c]pyridine-4-carboxylic acid (1-m-tolyl-cyclopropyl)-amide | 387.10 | 1.01 |
| 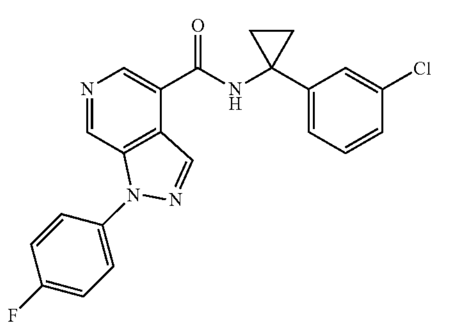 [SMILES: O=C(NC1(c2cccc(Cl)c2)CC1)c1cncc2c1cnn2-c1ccc(F)cc1] | 1-(4-Fluoro-phenyl)-1H-pyrazolo[3,4-c]pyridine-4-carboxylic acid [1-(3-chloro-phenyl)-cyclopropyl]-amide | 407.20 | 1.03 |

TABLE I-continued

| Structure | Name | Observed Mass [b] | rt (min) |
|---|---|---|---|
| 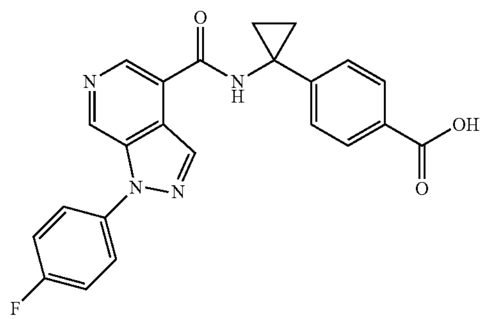 [SMILES: O=C(O)c1ccc(C2(NC(=O)c3cncc4c3cnn4-c3ccc(F)cc3)CC2)cc1] | 4-(1-{[1-(4-Fluoro-phenyl)-1H-pyrazolo[3,4-c]pyridine-4-carbonyl]-amino}-cyclopropyl)-benzoic acid | 417.19 | 0.8 |
| 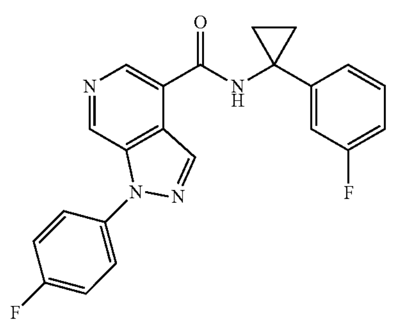 [SMILES: O=C(NC1(c2cccc(F)c2)CC1)c1cncc2c1cnn2-c1ccc(F)cc1] | 1-(4-Fluoro-phenyl)-1H-pyrazolo[3,4-c]pyridine-4-carboxylic acid [1-(3-fluoro-phenyl)-cyclopropyl]-amide | 391.98 | 0.97 |
| 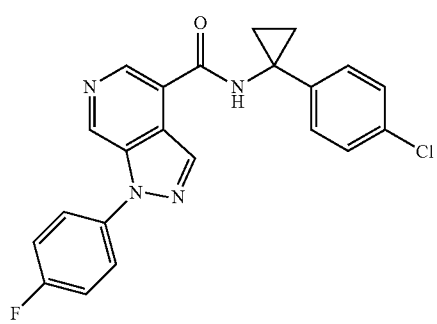 | 1-(4-Fluoro-phenyl)-1H-pyrazolo[3,4-c]pyridine-4-carboxylic acid [1-(4-chloro-phenyl)-cyclopropyl]-amide | 407.13 | 1.04 |
| 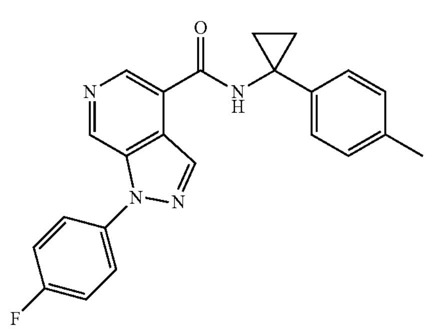 [SMILES: Cc1ccc(C2(NC(=O)c3cncc4c3cnn4-c3ccc(F)cc3)CC2)cc1] | 1-(4-Fluoro-phenyl)-1H-pyrazolo[3,4-c]pyridine-4-carboxylic acid (1-p-tolyl-cyclopropyl)-amide | 387.50 | 1.02 |

TABLE I-continued

| Structure | Name | HPLC-MS Data[a] | |
|---|---|---|---|
| | | Observed Mass[b] | rt (min) |
| 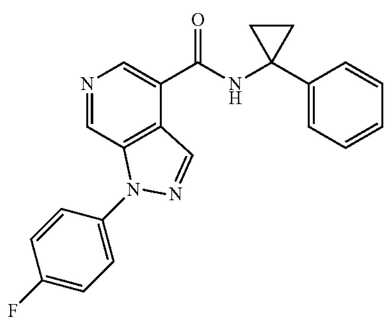 [SMILES: O=C(NC1(c2ccccc2)CC1)c1cncc2c1cnn2-c1ccc(F)cc1] | 1-(4-Fluoro-phenyl)-1H-pyrazolo[3,4-c]pyridine-4-carboxylic acid (1-phenyl-cyclopropyl)-amide | 373.97 | 0.95 |
| 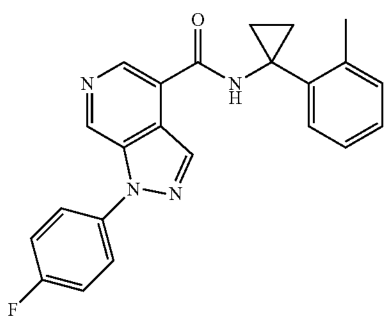 [SMILES: Cc1ccccc1C1(NC(=O)c2cncc3c2cnn3-c2ccc(F)cc2)CC1] | 1-(4-Fluoro-phenyl)-1H-pyrazolo[3,4-c]pyridine-4-carboxylic acid (1-o-tolyl-cyclopropyl)-amide | 388.27 | 1.02 |
| 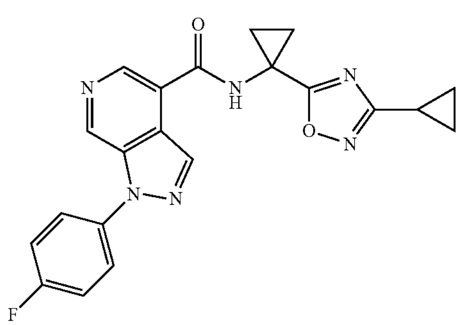 [SMILES: O=C(NC1(c2nc(C3CC3)no2)CC1)c1cncc2c1cnn2-c1ccc(F)cc1] | 1-(4-Fluoro-phenyl)-1H-pyrazolo[3,4-c]pyridine-4-carboxylic acid [1-(3-cyclopropyl-1,2,4-oxadiazol-5-yl)-cyclopropyl]-amide | 404.93 | 0.89 |
| 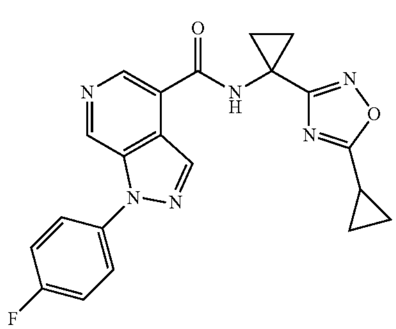 [SMILES: O=C(NC1(c2noc(C3CC3)n2)CC1)c1cncc2c1cnn2-c1ccc(F)cc1] | 1-(4-Fluoro-phenyl)-1H-pyrazolo[3,4-c]pyridine-4-carboxylic acid [1-(5-cyclopropyl-1,2,4-oxadiazol-3-yl)-cyclopropyl]-amide | 405.11 | 0.86 |

TABLE I-continued

| Structure | Name | HPLC-MS Data[a] Observed Mass[b] | rt (min) |
|---|---|---|---|
| 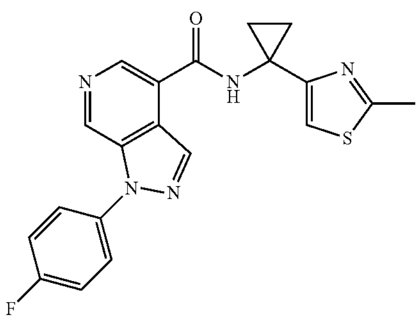 [SMILES: Cc1nc(C2(NC(=O)c3cncc4c3cnn4-c3ccc(F)cc3)CC2)cs1] | 1-(4-Fluoro-phenyl)-1H-pyrazolo[3,4-c]pyridine-4-carboxylic acid [1-(2-methyl-thiazol-4-yl)-cyclopropyl]-amide | 394.15 | 0.84 |
| 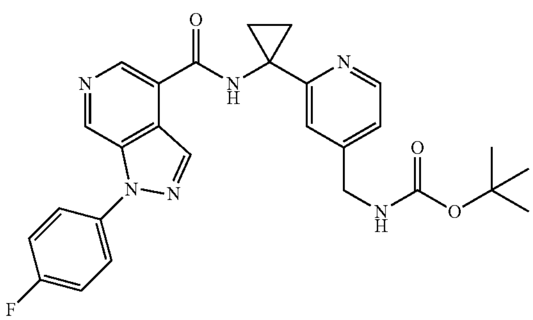 [SMILES: CC(C)(C)OC(=O)NCc1ccnc(C2(NC(=O)c3cncc4c3cnn4-c3ccc(F)cc3)CC2)c1] | [2-(1-{[1-(4-Fluoro-phenyl)-1H-pyrazolo[3,4-c]pyridine-4-carbonyl]-amino}-cyclopropyl)-pyridin-4-ylmethyl]-carbamic acid tert-butyl ester | 503.30 | 0.83 |
| 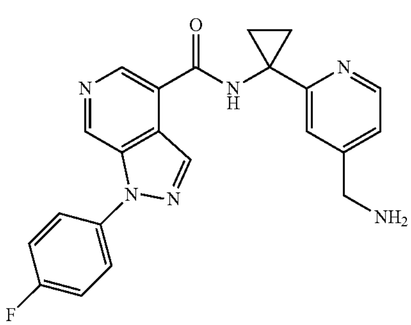 [SMILES: NCc1ccnc(C2(NC(=O)c3cncc4c3cnn4-c3ccc(F)cc3)CC2)c1] | 1-(4-Fluoro-phenyl)-1H-pyrazolo[3,4-c]pyridine-4-carboxylic acid [1-(4-aminomethyl-pyridin-2-yl)-cyclopropyl]-amide | 403.17 | 0.51 |
| 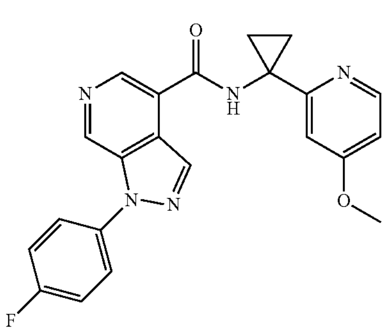 [SMILES: COc1ccnc(C2(NC(=O)c3cncc4c3cnn4-c3ccc(F)cc3)CC2)c1] | 1-(4-Fluoro-phenyl)-1H-pyrazolo[3,4-c]pyridine-4-carboxylic acid [1-(4-methoxy-pyridin-2-yl)-cyclopropyl]-amide | 404.20 | 0.58 |

TABLE I-continued

| Structure | Name | HPLC-MS Data[a] Observed Mass[b] | rt (min) |
|---|---|---|---|
| 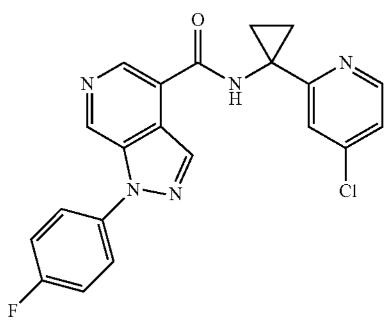 | 1-(4-Fluoro-phenyl)-1H-pyrazolo[3,4-c]pyridine-4-carboxylic acid [1-(4-chloro-pyridin-2-yl)-cyclopropyl]-amide | 408.13 | 0.92 |
| 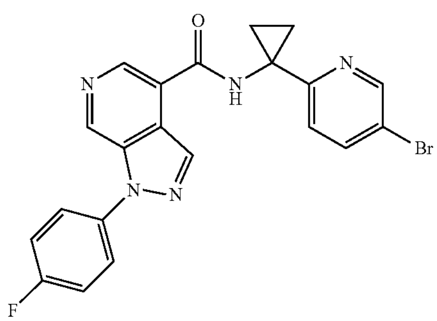 [SMILES: O=C(NC1(c2ccc(Br)cn2)CC1)c1cncc2c1cnn2-c1ccc(F)cc1] | 1-(4-Fluoro-phenyl)-1H-pyrazolo[3,4-c]pyridine-4-carboxylic acid [1-(5-bromo-pyridin-2-yl)-cyclopropyl]-amide | 452.10; 454.07 | 0.97 |
| 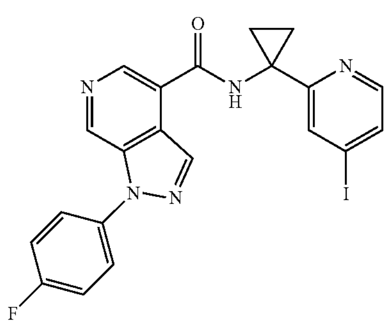 [SMILES: O=C(NC1(c2cc(I)ccn2)CC1)c1cncc2c1cnn2-c1ccc(F)cc1] | 1-(4-Fluoro-phenyl)-1H-pyrazolo[3,4-c]pyridine-4-carboxylic acid [1-(4-iodo-pyridin-2-yl)-cyclopropyl]-amide | 500.12 | 0.96 |
| 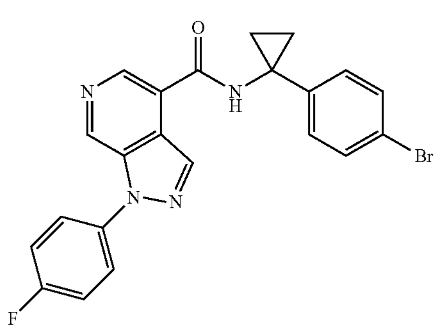 [SMILES: O=C(NC1(c2ccc(Br)cc2)CC1)c1cncc2c1cnn2-c1ccc(F)cc1] | 1-(4-Fluoro-phenyl)-1H-pyrazolo[3,4-c]pyridine-4-carboxylic acid [1-(4-bromo-phenyl)-cyclopropyl]-amide | 451.10; 453.06 | 1.06 |

TABLE I-continued

| Structure | Name | HPLC-MS Data[a] | |
|---|---|---|---|
| | | Observed Mass [b] | rt (min) |
| 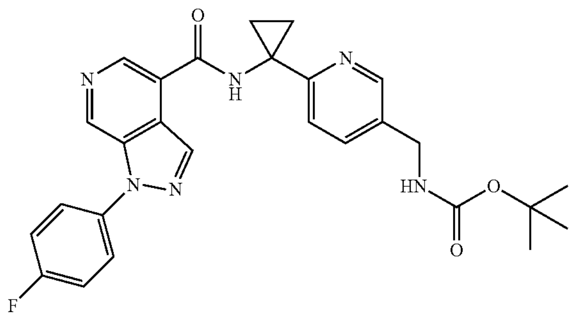 [SMILES: CC(C)(C)OC(=O)NCc1ccc(C2(NC(=O)c3cncc4c3cnn4-c3ccc(F)cc3)CC2)nc1] | [6-(1-{[1-(4-Fluoro-phenyl)-1H-pyrazolo[3,4-c]pyridine-4-carbonyl]-amino}-cyclopropyl)-pyridin-3-ylmethyl]-carbamic acid tert-butyl ester | 503.31 | 0.88 |
| 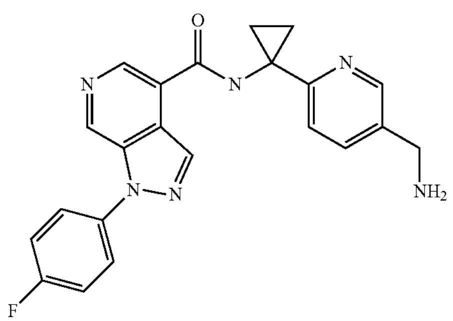 [SMILES: NCc1ccc(C2(NC(=O)c3cncc4c3cnn4-c3ccc(F)cc3)CC2)nc1] | 1-(4-Fluoro-phenyl)-1H-pyrazolo[3,4-c]pyridine-4-carboxylic acid [1-(5-aminomethyl-pyridin-2-yl)-cyclopropyl]-amide | 403.18 | 0.53 |
| 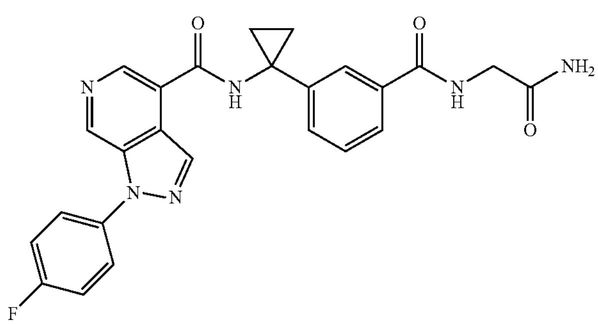 [SMILES: NC(=O)CNC(=O)c1cccc(C2(NC(=O)c3cncc4c3cnn4-c3ccc(F)cc3)CC2)c1] | 1-(4-Fluoro-phenyl)-1H-pyrazolo[3,4-c]pyridine-4-carboxylic acid {1-[3-(carbamoylmethyl-carbamoyl)-phenyl]-cyclopropyl}-amide | 473.23 | 1.25 |
| 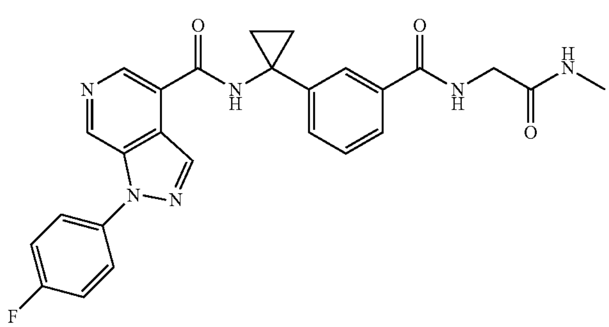 [SMILES: CNC(=O)CNC(=O)c1cccc(C2(NC(=O)c3cncc4c3cnn4-c3ccc(F)cc3)CC2)c1] | 1-(4-Fluoro-phenyl)-1H-pyrazolo[3,4-c]pyridine-4-carboxylic acid {1-[3-(methylcarbamoylmethyl-carbamoyl)-phenyl]-cyclopropyl}-amide | 487.24 | 1.28 |

TABLE I-continued

| Structure | Name | HPLC-MS Data[a] | |
|---|---|---|---|
| | | Observed Mass[b] | rt (min) |
| 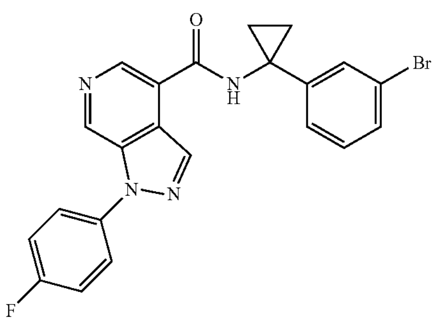 [SMILES: O=C(NC1(c2cccc(Br)c2)CC1)c1cncc2c1cnn2-c1ccc(F)cc1] | 1-(4-Fluoro-phenyl)-1H-pyrazolo[3,4-c]pyridine-4-carboxylic acid [1-(3-bromo-phenyl)-cyclopropyl]-amide | 451.10; 452.99 | 1.68 |
| 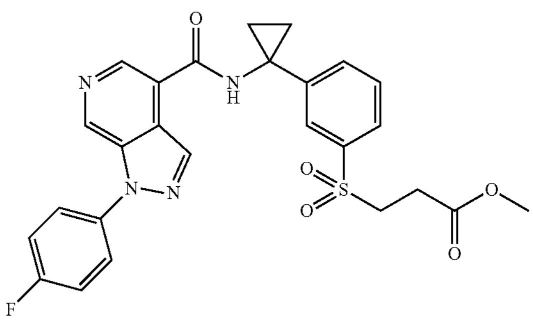 [SMILES: COC(=O)CCS(=O)(=O)c1cccc(C2(NC(=O)c3cncc4c3cnn4-c3ccc(F)cc3)CC2)c1] | 3-[3-(1-{[1-(4-Fluoro-phenyl)-1H-pyrazolo[3,4-c]pyridine-4-carbonyl]-amino}-cyclopropyl)-benzenesulfonyl]-propionic acid methyl ester | 523.21 | 1.50 |
| 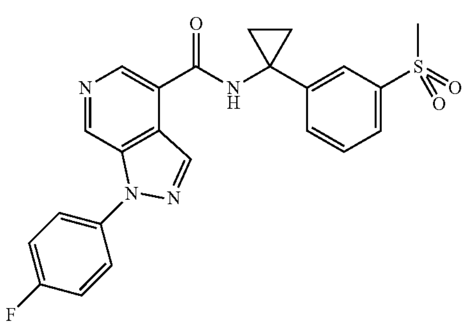 [SMILES: CS(=O)(=O)c1cccc(C2(NC(=O)c3cncc4c3cnn4-c3ccc(F)cc3)CC2)c1] | 1-(4-Fluoro-phenyl)-1H-pyrazolo[3,4-c]pyridine-4-carboxylic acid [1-(3-methanesulfonyl-phenyl)-cyclopropyl]-amide | 451.24 | 1.45 |
| 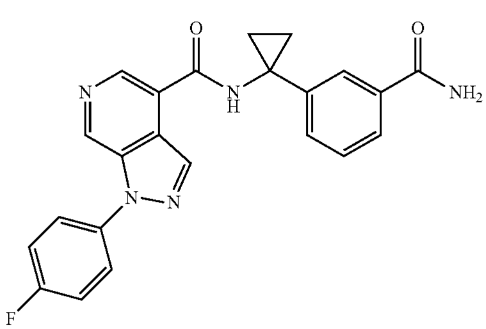 [SMILES: NC(=O)c1cccc(C2(NC(=O)c3cncc4c3cnn4-c3ccc(F)cc3)CC2)c1] | 1-(4-Fluoro-phenyl)-1H-pyrazolo[3,4-c]pyridine-4-carboxylic acid [1-(3-carbamoyl-phenyl)-cyclopropyl]-amide | 416.23 | 1.33 |

TABLE I-continued

| Structure | Name | HPLC-MS Data[a] Observed Mass[b] | rt (min) |
|---|---|---|---|
| 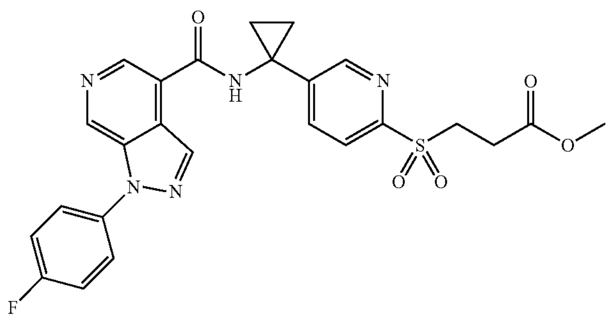 [SMILES: COC(=O)CCS(=O)(=O)c1ccc(C2(NC(=O)c3cncc4c3cnn4-c3ccc(F)cc3)CC2)cn1] | 3-[5-(1-{[1-(4-Fluoro-phenyl)-1H-pyrazolo[3,4-c]pyridine-4-carbonyl]-amino}-cyclopropyl)-pyridine-2-sulfonyl]-propionic acid methyl ester | 524.23 | 1.40 |
| 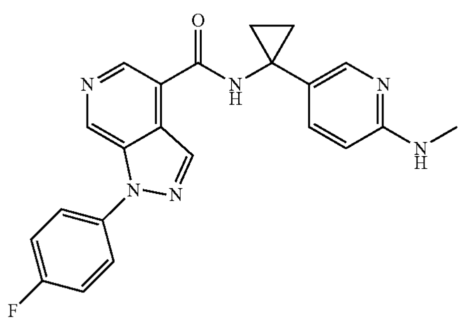 [SMILES: CNc1ccc(C2(NC(=O)c3cncc4c3cnn4-c3ccc(F)cc3)CC2)cn1] | 1-(4-Fluoro-phenyl)-1H-pyrazolo[3,4-c]pyridine-4-carboxylic acid [1-(6-methylamino-pyridin-3-yl)-cyclopropyl]-amide | 403.21 | 1.24 |
| 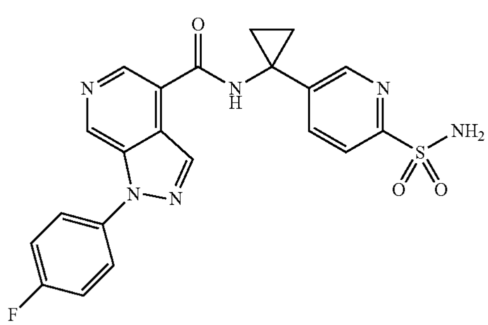 [SMILES: NS(=O)(=O)c1ccc(C2(NC(=O)c3cncc4c3cnn4-c3ccc(F)cc3)CC2)cn1] | 1-(4-Fluoro-phenyl)-1H-pyrazolo[3,4-c]pyridine-4-carboxylic acid [1-(6-sulfamoyl-pyridin-3-yl)-cyclopropyl]-amide | 453.13 | 1.33 |
| 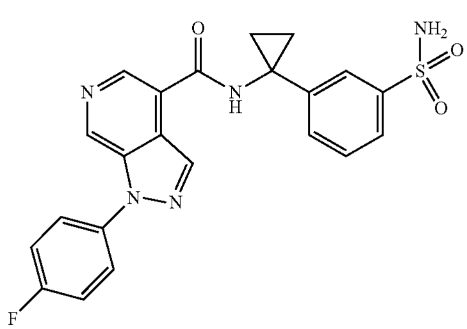 [SMILES: NS(=O)(=O)c1cccc(C2(NC(=O)c3cncc4c3cnn4-c3ccc(F)cc3)CC2)c1] | 1-(4-Fluoro-phenyl)-1H-pyrazolo[3,4-c]pyridine-4-carboxylic acid [1-(3-sulfamoyl-phenyl)-cyclopropyl]-amide | 452.22 | 1.39 |

TABLE I-continued

| Structure | Name | HPLC-MS Data[a] | |
|---|---|---|---|
| | | Observed Mass [b] | rt (min) |
| 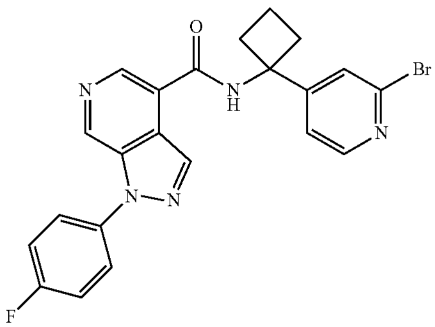 [SMILES: O=C(NC1(c2ccnc(Br)c2)CCC1)c1cncc2c1cnn2-c1ccc(F)cc1] | 1-(4-Fluoro-phenyl)-1H-pyrazolo[3,4-c]pyridine-4-carboxylic acid [1-(2-bromo-pyridin-4-yl)-cyclobutyl]-amide | 466.14; 468.08 | 1.61 |
| 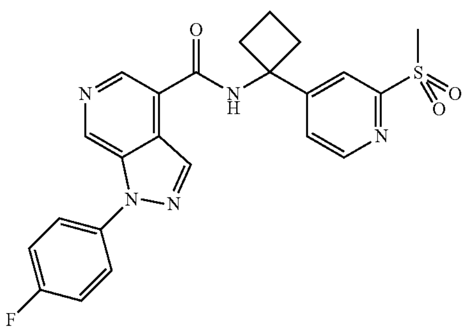 [SMILES: CS(=O)(=O)c1cc(C2(NC(=O)c3cncc4c3cnn4-c3ccc(F)cc3)CCC2)ccn1] | 1-(4-Fluoro-phenyl)-1H-pyrazolo[3,4-c]pyridine-4-carboxylic acid [1-(2-methanesulfonyl-pyridin-4-yl)-cyclobutyl]-amide | 466.14 | 1.43 |
| 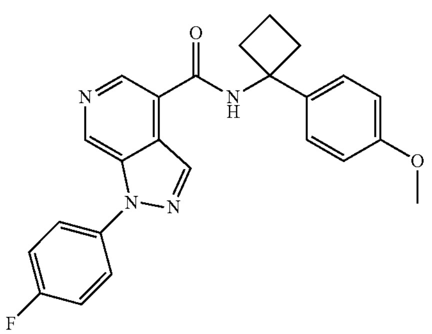 [SMILES: COc1ccc(C2(NC(=O)c3cncc4c3cnn4-c3ccc(F)cc3)CCC2)cc1] | 1-(4-Fluoro-phenyl)-1H-pyrazolo[3,4-c]pyridine-4-carboxylic acid [1-(4-methoxy-phenyl)-cyclobutyl]-amide | 417.58 | 1.02 |
| 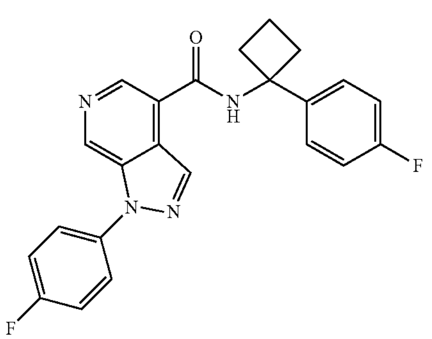 [SMILES: O=C(NC1(c2ccc(F)cc2)CCC1)c1cncc2c1cnn2-c1ccc(F)cc1] | 1-(4-Fluoro-phenyl)-1H-pyrazolo[3,4-c]pyridine-4-carboxylic acid [1-(4-fluoro-phenyl)-cyclobutyl]-amide | 405.09 | 1.05 |

TABLE I-continued

| Structure | Name | Observed Mass | rt (min) |
|---|---|---|---|
| 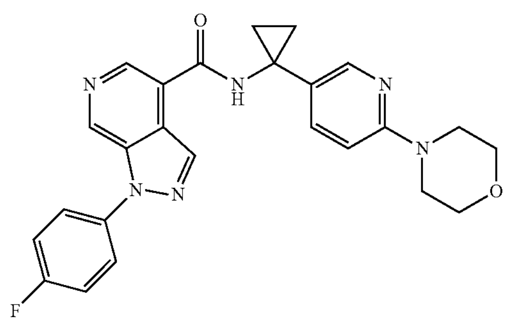 [SMILES: O=C(NC1(c2ccc(N3CCOCC3)nc2)CC1)c1cncc2c1cnn2-c1ccc(F)cc1] | 1-(4-Fluoro-phenyl)-1H-pyrazolo[3,4-c]pyridine-4-carboxylic acid [1-(6-morpholin-4-yl-pyridin-3-yl)-cyclopropyl]-amide | 459.21 | 1.27 |
| 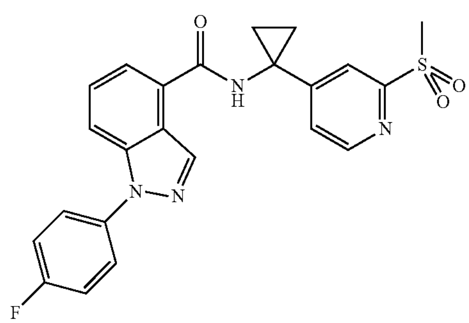 [SMILES: CS(=O)(=O)c1cc(C2(NC(=O)c3cccc4c3cnn4-c3ccc(F)cc3)CC2)ccn1] | 1-(4-Fluoro-phenyl)-1H-indazole-4-carboxylic acid [1-(2-methanesulfonyl-pyridin-4-yl)-cyclopropyl]-amide | 451.16 | 1.50 |
| 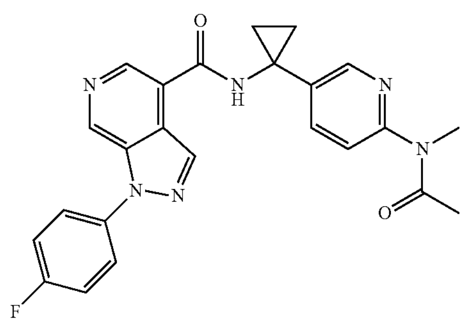 [SMILES: CC(=O)N(C)c1ccc(C2(NC(=O)c3cncc4c3cnn4-c3ccc(F)cc3)CC2)cn1] | 1-(4-Fluoro-phenyl)-1H-pyrazolo[3,4-c]pyridine-4-carboxylic acid {1-[6-(acetyl-methyl-amino)-pyridin-3-yl]-cyclopropyl}-amide | 445.24 | 1.46 |
| 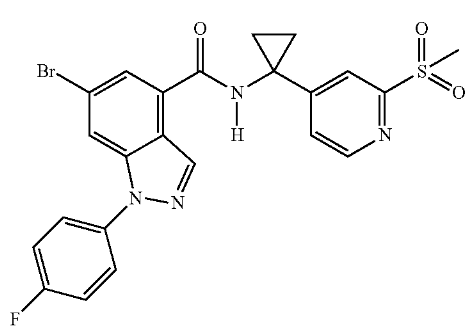 [SMILES: CS(=O)(=O)c1cc(C2(NC(=O)c3cc(Br)cc4c3cnn4-c3ccc(F)cc3)CC2)ccn1] | 6-Bromo-1-(4-fluoro-phenyl)-1H-indazol-4-carboxylic acid [1-(2-methanesulfonyl-pyridin-4-yl)-cyclopropyl]-amide | 529.07; 531.06 | 1.63 |

TABLE I-continued

| Structure | Name | HPLC-MS Data[a] Observed Mass[b] | rt (min) |
|---|---|---|---|
| 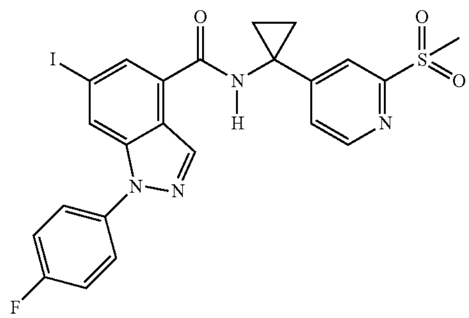 [SMILES: CS(=O)(=O)c1cc(C2(NC(=O)c3cc(I)cc4c3cnn4-c3ccc(F)cc3)CC2)ccn1] | 1-(4-Fluoro-phenyl)-6-iodo-1H-indazole-4-carboxylic acid [1-(2-methanesulfonyl-pyridin-4-yl)-cyclopropyl]-amide | 577.08 | 1.65 |
| 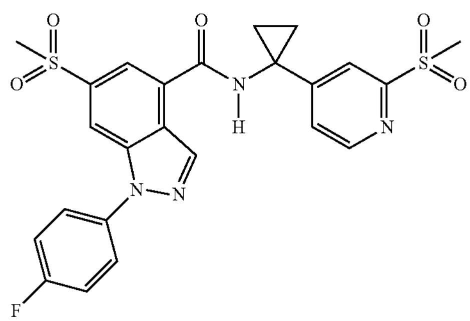 [SMILES: CS(=O)(=O)c1cc(C(=O)NC2(c3ccnc(S(C)(=O)=O)c3)CC2)c2cnn(-c3ccc(F)cc3)c2c1] | 1-(4-Fluoro-phenyl)-6-methanesulfonyl-1H-indazole-4-carboxylic acid [1-(2-methanesulfonyl-pyridin-4-yl)-cyclopropyl]-amide | 529.15 | 1.47 |
| 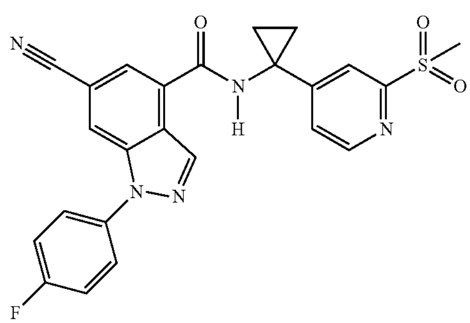 [SMILES: CS(=O)(=O)c1cc(C2(NC(=O)c3cc(C#N)cc4c3cnn4-c3ccc(F)cc3)CC2)ccn1] | 6-Cyano-1-(4-fluoro-phenyl)-1H-indazole-4-carboxylic acid [1-(2-methanesulfonyl-pyridin-4-yl)-cyclopropyl]-amide | 476.15 | 1.53 |

[a] See Synthetic Example Section for HPLC-MS methods.
[b] Observed [M + H]⁺ is reported for all compounds. For bromine containing compounds, the observed [M + H]⁺ for two bromine isotopes (i.e., $^{79}$Br and $^{81}$Br) are reported.

or the pharmaceutically acceptable salts thereof.

For all compounds disclosed hereinabove in this application, in the event the nomenclature is in conflict with the structure, it shall be understood that the compound is defined by the structure.

The invention also relates to pharmaceutical preparations, containing as active substance one or more compounds of the invention, or the pharmaceutically acceptable derivatives thereof, optionally combined with conventional excipients and/or carriers.

Compounds of the invention also include their isotopically-labelled forms. An isotopically-labelled form of an active agent of a combination of the present invention is identical to said active agent but for the fact that one or more atoms of said active agent have been replaced by an atom or atoms having an atomic mass or mass number different from the atomic mass or mass number of said atom which is usually found in nature. Examples of isotopes which are readily available commercially and which can be incorporated into an active agent of a combination of the present invention in accordance with well established procedures, include isotopes of hydrogen, carbon, nitrogen, oxygen, phosphorous, fluorine and chlorine, e.g., $^{2}$H, $^{3}$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. An active agent of a combination of the present invention, a prodrug thereof, or a pharmaceutically acceptable salt of either which contains one or more of the above-mentioned isotopes and/or other isotopes of other atoms is contemplated to be within the scope of the present invention.

The invention includes the use of any compounds of described above containing one or more asymmetric carbon atoms may occur as racemates and racemic mixtures, single enantiomers, diastereomeric mixtures and individual diastereomers. Isomers shall be defined as being enantiomers and diastereomers. All such isomeric forms of these compounds are expressly included in the present invention. Each stereogenic carbon may be in the R or S configuration, or a combination of configurations.

Some of the compounds of the invention can exist in more than one tautomeric form. The invention includes methods using all such tautomers.

All terms as used herein in this specification, unless otherwise stated, shall be understood in their ordinary meaning as known in the art. For example, "$C_{1-4}$ alkoxy" is a $C_{1-4}$ alkyl with a terminal oxygen, such as methoxy, ethoxy, propoxy, butoxy. All alkyl, alkenyl and alkynyl groups shall be understood as being branched or unbranched where structurally possible and unless otherwise specified. Other more specific definitions are as follows:

Carbocycles include hydrocarbon rings containing from three to twelve carbon atoms. These carbocycles may be either aromatic or non-aromatic ring systems. The non-aromatic ring systems may be mono- or polyunsaturated. Preferred carbocycles include but are not limited to cyclopropyl, cyclobutyl, cyclopentyl, cyclopentenyl, cyclohexyl, cyclohexenyl, cycloheptanyl, cycloheptenyl, phenyl, indanyl, indenyl, benzocyclobutanyl, dihydronaphthyl, tetrahydronaphthyl, naphthyl, decahydronaphthyl, benzocycloheptanyl and benzocycloheptenyl. Certain terms for cycloalkyl such as cyclobutanyl and cyclobutyl shall be used interchangeably.

The term "heterocycle" refers to a stable nonaromatic 4-8 membered (but preferably, 4 or 6 membered) monocyclic or nonaromatic 8-11 membered bicyclic or spirocyclic heterocycle radical which may be either saturated or unsaturated. Each heterocycle consists of carbon atoms and one or more, preferably from 1 to 4 heteroatoms chosen from nitrogen, oxygen and sulfur. The heterocycle may be attached by any atom of the cycle, which results in the creation of a stable structure.

The term "heteroaryl" shall be understood to mean an aromatic 5-8 membered monocyclic or 8-11 membered bicyclic ring containing 1-4 heteroatoms such as N, O and S.

Unless otherwise stated, heterocycles and heteroaryl include but are not limited to, for example furanyl, pyranyl, benzoxazolyl, benzothiazolyl, benzimidazolyl, tetrahydropyranyl, dioxanyl, dioxolanyl, tetrahydrofuranyl, oxazolyl, isoxazolyl, thiazolyl, pyrazolyl, pyrrolyl, imidazolyl, thienyl, thiadiazolyl, thiomorpholinyl, 1,1-dioxo-1$\lambda^6$-thiomorpholinyl, morpholinyl, pyridinyl, pyrimidinyl, pyridazinyl, pyrazinyl, triazinyl, pyrrolidinyl, piperidinyl, piperazinyl, purinyl, quinolinyl, dihydro-2H-quinolinyl, isoquinolinyl, quinazolinyl, indazolyl, thieno [2,3-d]pyrimidinyl, indolyl, isoindolyl, benzofuranyl, benzopyranyl and benzodioxolyl.

The term "heteroatom" as used herein shall be understood to mean atoms other than carbon such as O, N, S and P.

In all alkyl groups or carbon chains one or more carbon atoms can be optionally replaced by heteroatoms: O, S or N, it shall be understood that if N is not substituted then it is NH, it shall also be understood that the heteroatoms may replace either terminal carbon atoms or internal carbon atoms within a branched or unbranched carbon chain. Such groups can be substituted as herein above described by groups such as oxo to result in definitions such as but not limited to: alkoxycarbonyl, acyl, amido and thioxo.

The term "aryl" as used herein shall be understood to mean aromatic carbocycle or heteroaryl as defined herein. Each aryl or heteroaryl unless otherwise specified includes it's partially or fully hydrogenated derivative. For example, quinolinyl may include decahydroquinolinyl and tetrahydroquinolinyl, naphthyl may include its hydrogenated derivatives such as tetrahydranaphthyl. Other partially or fully hydrogenated derivatives of the aryl and heteroaryl compounds described herein will be apparent to one of ordinary skill in the art.

As used herein, "nitrogen" and "sulfur" include any oxidized form of nitrogen and sulfur and the quaternized form of any basic nitrogen. For example, for an —S—$C_{1-6}$ alkyl radical, unless otherwise specified, this shall be understood to include —S(O)—$C_{1-6}$ alkyl and —S(O)$_2$—$C_{1-6}$ alkyl.

The term "alkyl" refers to a saturated aliphatic radical containing from one to ten carbon atoms or a mono- or polyunsaturated aliphatic hydrocarbon radical containing from two to twelve carbon atoms. A mono- or polyunsaturated aliphatic hydrocarbon radical must contain at least one double or triple bond, respectively. "Alkyl" refers to both branched and unbranched alkyl groups. It should be understood that any combination term using an "alk" or "alkyl" prefix refers to analogs according to the above definition of "alkyl". For example, terms such as "alkoxy", "alkythio" refer to alkyl groups linked to a second group via an oxygen or sulfur atom. "Alkanoyl" refers to an alkyl group linked to a carbonyl group (C=O).

The term "halogen" as used in the present specification shall be understood to mean bromine, chlorine, fluorine or iodine, preferably fluorine. The definitions "halogenated", "partially or fully halogenated"; partially or fully fluorinated; "substituted by one or more halogen atoms", includes for example, mono, di or tri halo derivatives on one or more carbon atoms. For alkyl, a nonlimiting example would be —$CH_2CHF_2$, —$CF_3$ etc.

Each alkyl, carbocycle, heterocycle or heteroaryl, or the analogs thereof, described herein shall be understood to be optionally partially or fully halogenated.

The compounds of the invention are only those which are contemplated to be 'chemically stable' as will be appreciated by those skilled in the art. For example, a compound which would have a 'dangling valency', or a 'carbanion' are not compounds contemplated by the inventive methods disclosed herein.

The invention includes pharmaceutically acceptable derivatives of compounds of formula (I). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the invention.

Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts. Salts derived from appropriate bases include alkali metal (e.g., sodium), alkaline earth metal (e.g., magnesium), ammonium and N—($C_1$-$C_4$ alkyl)$_4^+$ salts.

In addition, within the scope of the invention is use of prodrugs of compounds of the invention. Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

The compounds of formula I may be made using the general synthetic methods described below, which also constitute part of the invention.

GENERAL SYNTHETIC METHODS

The invention additionally provides for methods for making compounds of formula I. The compounds of the invention may be prepared by the general methods and examples presented below, and methods known to those of ordinary skill in the art and reported in the chemical literature.

Unless otherwise specified, solvents, temperatures, pressures, and other reaction conditions may be readily selected by one of ordinary skill in the art. Specific procedures are provided in the Synthetic Examples section.

Aryl- or heteroaryl-cycloalkylamine intermediates are either commercially available, prepared according to the general procedures or references described below (hereby incorporated by reference in their entirety), or may be prepared by one skilled in the art using methods described in the chemical literature.

Aryl- or heteroaryl-cyclopropylamine may be synthesized via titanium alkoxide-mediated reductive cyclopropanation of the corresponding aryl or heteroaryl nitriles with Grignard reagents (Szymoniak, J. et al. *J. Org. Chem.* 2002, 67, 3965, and Bertus, P. et al. *J. Org. Chem.* 2003, 68, 7133) or with zinc reagents (de Meijere, A. et al. *Org. Lett.* 5, 2003, 753). Alternatively, aryl-cyclopropylamines may be synthesized from aryl nitriles or aryl esters via cycloalkylation (e.g., Jonczyk, A. et al. *Org. Prep. Proc.* 27, 1995, 355), followed by conversion of the nitrile or ester group to a carboxylic acid, Curtius rearrangement of the resulting carboxylic acid to a carbamic ester (e.g., Hanano, T. et al. *Bioorg. Med. Chem. Lett.* 10, 2000, 881), and deprotection of the resulting carbamic ester.

Amide bond formations may be carried out by standard coupling conditions well-known in the art (e.g., Bodanszky, M. *The Practice of Peptide Synthesis*, Springer-Verlag, 1984, which is hereby incorporated by reference in its entirety), such as reacting a carboxylic acid and an amine in the presence of 1-(3)-dimethylaminopropyl)-3-ethylcarbodiimide (EDC) and 1-hydroxybenzotriazole. Reaction progress may be monitored by conventional methods such as thin layer chromatography (TLC). Intermediates and products may be purified by methods known in the art, including column chromatography, HPLC or recrystallization.

The methods described below and in the Synthetic Examples section may be used to prepare compounds of formula Ia (i.e., compounds of formula I wherein X is nitrogen, Schemes I, II and III), and compounds of formula Ib (i.e., compounds of formula I wherein X is C—$R_2$, Schemes IV and V). In the schemes below, $Ar_1$, $Ar_2$, cyclic G, X, $R_1$ and $R_2$, shall have the meanings defined in the detailed description of compounds of formula I.

Compounds of formula Ia may be prepared according to Schemes I-III.

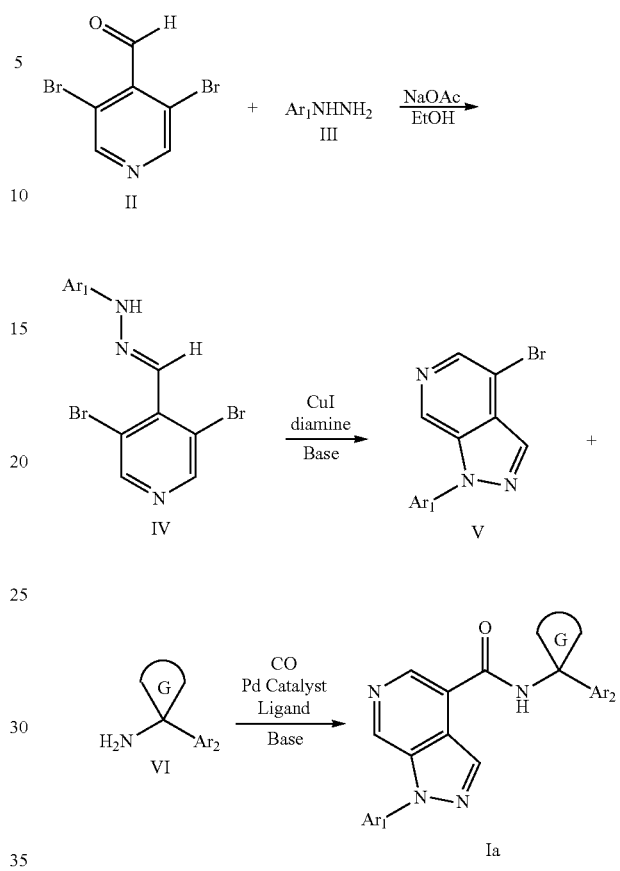

As illustrated in Scheme I, a suitable hydrazine of the formula III (free base or a suitable salt form such as a hydrochloride salt) bearing $Ar_1$ may be reacted with 3,5-dibromo-4-pyridinecarboxaldehyde II in the presence of sodium acetate and in a suitable solvent such as EtOH to provide the hydrazone of formula IV. Compound of formula IV may be cyclized in the presence of suitable reagents such as a diamine ligand (e.g., trans-N,N'-dimethylcyclohexane-1,2-diamine), a copper salt (e.g., CuI), a base (e.g., $K_2CO_3$), and a solvent (e.g., N-methyl-2-pyrrolidinone) to provide the compound of formula V. The bromo-azaindazole V may be heated in a sealed pressure vessel with a suitable amine of formula VI in the presence of suitable cross coupling reagents such as a Pd catalyst (e.g., Pd(PhCN)$_2$Cl$_2$), a ligand [e.g., 1,1-bis(diphenylphosphino)ferrocene (dppf)], a base (e.g., Et$_3$N), and a solvent (e.g., toluene), under an atmosphere of CO that is pressurized (preferably at about 15 bars) to afford the desired compound of formula Ia.

Scheme II

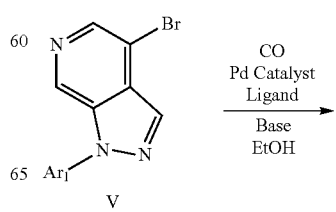

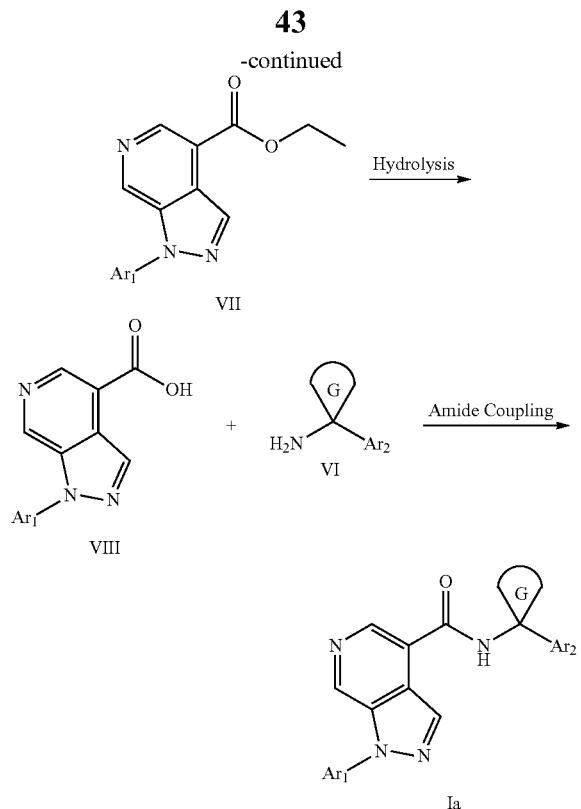

Alternatively, compounds of formula Ia may be synthesized according to the general procedure illustrated in Scheme II. Bromo-azaindazole of formula V may be heated under pressurized CO atmosphere, in the presence of a suitable Pd catalyst, ligand and base as described above in absolute ethanol to provide the ethyl ester of formula VII, which may be hydrolyzed with a suitable hydroxide base (e.g., KOH) in a suitable solvent system such as aqueous methanol to afford the carboxylic acid of formula of VIII. Carboxylic acid VIII may be reacted with a suitable amine of formula VI under amide coupling conditions well known in the art. For example, acid VIII may be treated with a suitable activating reagent such as thionyl chloride, oxalyl chloride, (benzotriazol-1-yloxy)tripyrrolidinophosphonium-hexafluorophosphate (PyBOP), O-(7-azabenzotriazol-1yl)-N,N,N',N'-tetramethyluronium hexafluorophosphate (HATU), O-(benzotriazol-1-yl)-N,N,N',N'-tetramethyluronium hexafluorophosphate (HBTU), or O-(benzotriazol-1-yl)-N,N,N',N'-tetramethyluronium tetrafluoroborate (TBTU) in the presence of a suitable amine of formula VI, a suitable base (e.g., triethylamine or N,N-diisopropylethylamine) in a suitable solvent (e.g., dimethylformamide or N-methylpyrrolidinone) to provide the desired compound of formula Ia.

Scheme III

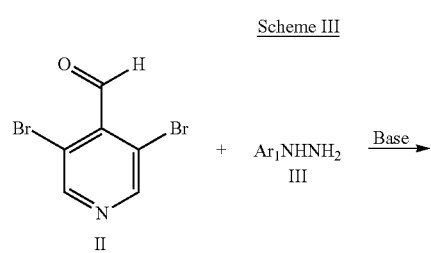

Alternatively, the carboxylic acid of formula VIII may be prepared according to the synthesis sequence shown in Scheme III. A compound of the formula II may be reacted with a suitable hydrazine of the formula III (free base or a suitable salt form such as a hydrochloride salt) using a polar aprotic solvent (e.g., NMP, DMF, DMAC, or DMPU) in the presence of a base (e.g., aqueous KOH, aqueous NaOH, aqueous LiOH, aqueous CsOH, NaOMe, NaOEt, KOt-Bu or KOt-amyl), at a suitable temperature (preferably at about 80° C.) to provide the compound of formula V. Bromo-azaindazole V may be reacted with a suitable Grignard reagent (e.g., R—MgCl where R may be chosen from isopropyl, n-butyl, sec-butyl and cyclohexyl), and $CO_2$ in a suitable polar aprotic solvent such as THF, MTBE, $Et_2O$, DME or dioxane, at a suitable reaction temperature (preferably at about −20° C.) to afford the carboxylic acid of formula VIII, which may be converted to compounds of formula Ia as described above.

Compounds of formula Ib may be prepared as shown in Schemes IV and V. In these schemes, $Ar_1$, $Ar_2$, G, X, $R_1$ and $R_2$, shall have the meanings defined in the detailed description of compounds of formula I.

Scheme IV

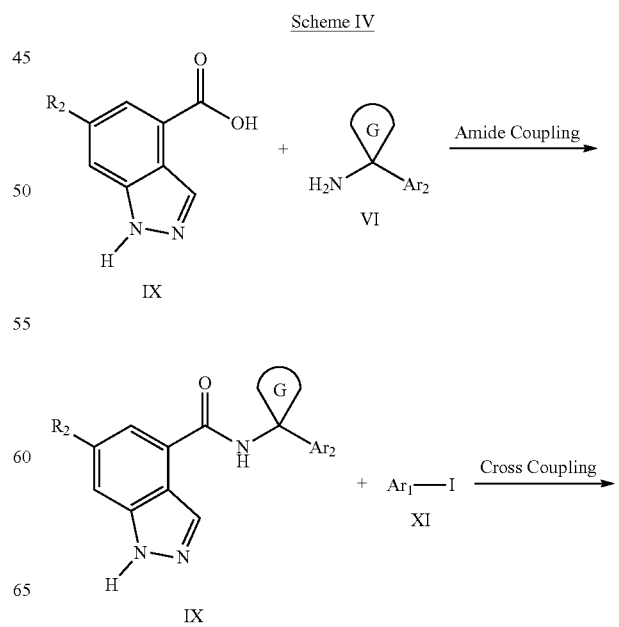

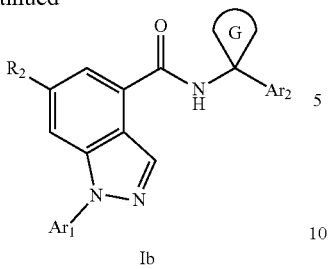

Ib

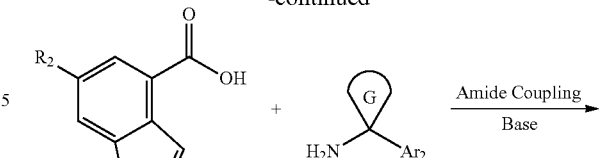

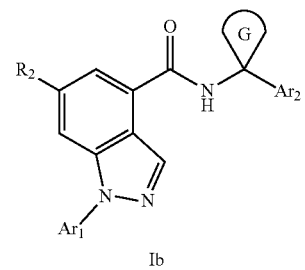

Ib

As depicted in Scheme IV, an indazole-4-carboxylic acid of formula IX may be coupled to a suitable amine of formula VI using amide bond coupling conditions well known in the art such as those described above. The resultant indazole-4-carboxamide may be reacted with a suitable aryl halide of formula XI under cross coupling conditions that are known in the chemical literature such as heating at a suitable temperature (preferably at about 120° C.), in the presence of suitable reagents such as a catalyst (e.g., CO, a base (e.g., $K_2CO_3$), and a ligand (e.g., racemic trans-N,N'-dimethylcyclohexane-1,2-diamine), in a suitable solvent (e.g., DMF) to provide the compound of formula Ib.

Alternatively, compounds of formula Ib may be synthesized as illustrated in Scheme V.

An indazole-4-carboxylic acid of formula IX may be transformed to its corresponding carboxylic ester of formula XII using esterification conditions well known in the art such as treatment with trimethylsilyl diazomethane in a suitable solvent system (e.g., methanol and toluene). Ester XII may be reacted with a suitable aryl halide of formula XI under cross coupling conditions described above to provide the indazole-4-carboxylic ester of formula XIII, which may be converted to the acid of formula XIV under standard hydrolysis conditions such as treatment with a suitable base (e.g., NaOH) in a suitable aqueous solvent system (e.g., water and methanol). As previously described, the acid of formula XIV may be converted to the compound of formula Ib by reaction with amine VI under amide coupling conditions known in the art.

Compounds of formula I prepared by the above methods may be further converted to additional compounds of formula I by methods known in the art and exemplified in the Synthetic Examples section below.

The methods described below (i.e., Schemes VI-IX) and in the Synthetic Examples section may be used to prepare intermediates VI, which may be used in the preparation of compounds of formula I. In the schemes below, cyclic G, $Ar_2$ and $R_b$ shall have the meanings defined in the detailed description of compounds of formula I.

Intermediates of formula VIa (i.e., intermediate of formula VI wherein $Ar_2$ is a 1,3,4-thiadiazole) may be prepared according to Scheme VI.

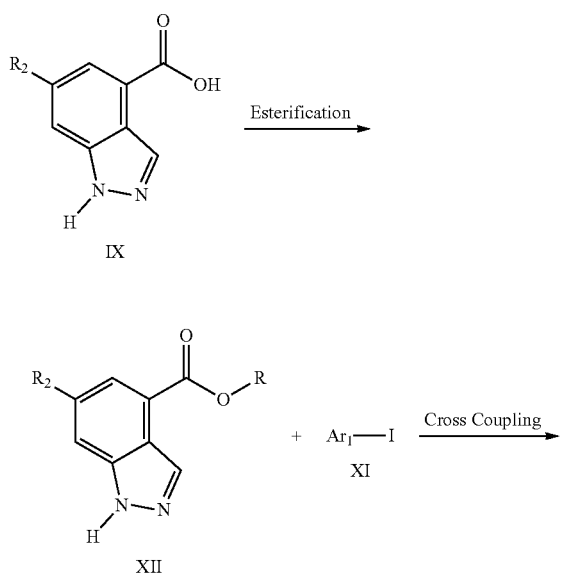

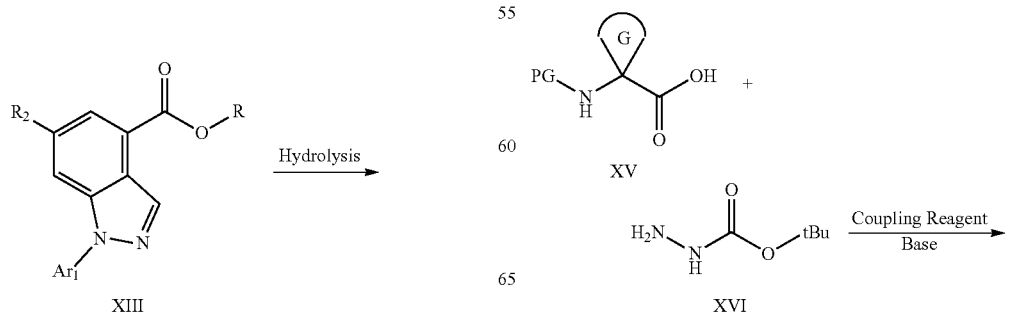

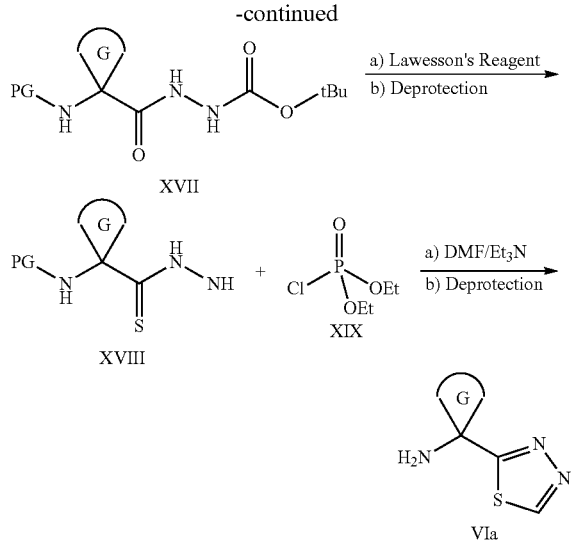

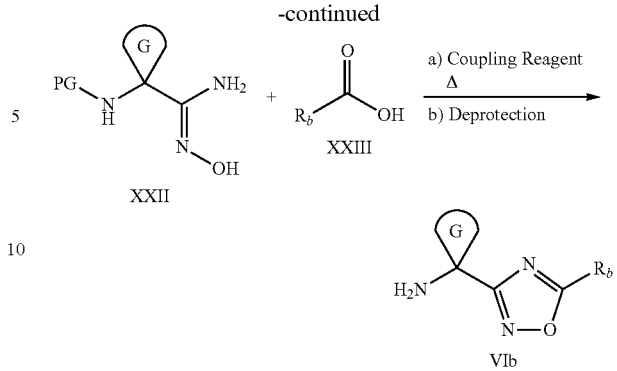

As illustrated in Scheme VI, an amino acid of the formula XV wherein PG is a suitable protecting group (e.g., Cbz) may be coupled with Boc-protected hydrazine XVI using amide bond coupling conditions well-known in the art such as those described above to provide a Boc-protected hydrazide XVII. A compound of formula XVII may be reacted with Lawesson's Reagent in the presence of a suitable solvent such as toluene and at a suitable temperature (e.g., at about 90° C.) to provide the corresponding Boc-protected thiohydrazide, which may be deprotected using a suitable acid such as 4N HCl in dioxane to provide the appropriate salt form (e.g., a hydrochloride salt) of thiohydrazide XVIII. A compound of formula XVIII may be reacted with DMF in the presence of a suitable reagent such as diethyl chlorophosphate XIX and a suitable base (e.g., Et$_3$N) to provide the corresponding 1,3,4-thiadiazole, which may be N-deprotected with a suitable reagent (e.g., 48% HBr in acetic acid) to afford an intermediate of formula VIa.

Additionally, intermediates of formula VIb (i.e., intermediate of formula VI wherein Ar$_2$ is a 1,2,4-oxadiazole) may be prepared according to Scheme VII.

Scheme VII

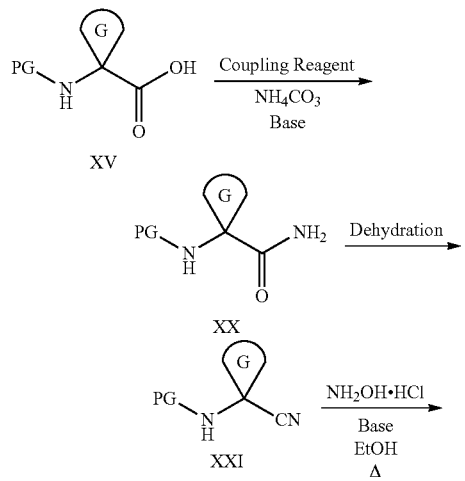

As shown in Scheme VII, a suitably protected amino acid of the formula XV (i.e., PG is a suitable protecting group such as Cbz) may be converted to the corresponding amide XX using standard amide bond coupling conditions such as those described above, and in the presence of a suitable ammonium salt such as ammonium carbonate, a suitable base (e.g., Et$_3$N) and a suitable solvent (e.g., DMF). An amide of formula XX may be reacted with suitable dehydrating reagent such as cyanuric chloride, in the presence of a suitable solvent (e.g., DMF) and at a suitable temperature (e.g., at about 0° C. to 30° C.) to provide a nitrile of formula XXI. A compound XXI may be reacted with hydroxylamine hydrochloride, in the presence of a suitable base such as potassium carbonate, in a suitable solvent (e.g., ethanol) and at a suitable temperature (e.g., at about 79° C.) to provide a compound of formula XXII. An amidoxime XXII may be reacted with a suitable carboxylic acid of formula XXIII using an amide bond coupling reagent well-known in the art (e.g., CDI), in a suitable solvent (e.g., DMF), and under suitable conditions (e.g., heating at about 100° C.) to afford the corresponding 1,2,4-oxadiazole derivative that may be N-deprotected as described above to furnish an intermediate of formula VIb.

Intermediates of formula VIc (i.e., intermediate of formula VI wherein Ar$_2$ is a different regioisomer of 1,2,4-oxadiazole) may be prepared according to Scheme VIII.

Scheme VIII

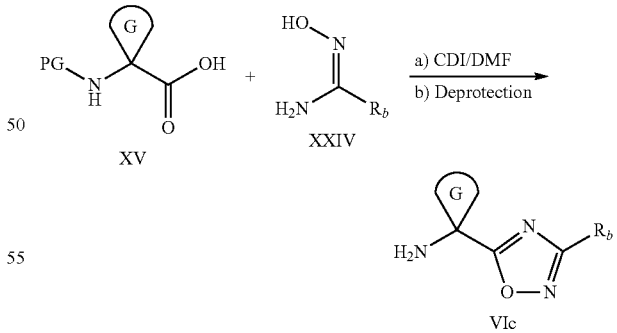

An amidoxime of formula XXIV may be prepared by the addition of hydroxylamine to the corresponding nitrile under suitable conditions as described above. As depicted in Scheme VIII, an amidoxime XXIV may be reacted with an amino acid of the formula XV wherein PG is a suitable protecting group (e.g., Boc) utilizing a suitable amide coupling reagent such as CDI, in a suitable solvent such as DMF, and under suitable conditions (e.g., heating at about 100° C.)

to provide the corresponding 1,2,4-oxadiazole, which may be N-deprotected under a suitable condition (e.g., reaction with a suitable acid such as 4N HCl in dioxane) to afford an intermediate of formula VIc.

Intermediates of formula VId (i.e., intermediate of formula VI wherein Ar$_2$ is a pyrimidine) may be prepared according to Scheme IX.

pose of supporting embodiments of this invention, and are not to be construed as limiting the scope of the invention in any way. Suitable protection of amino acids may be carried out by standard conditions well-known in the art (for a comprehensive list see, Greene, T. W.; Wuts, P. G. M. *Protective Groups in Organic Synthesis*, 3$^{rd}$ Ed., Wiley, New York, 1999, which is hereby incorporated by reference in its entirety).

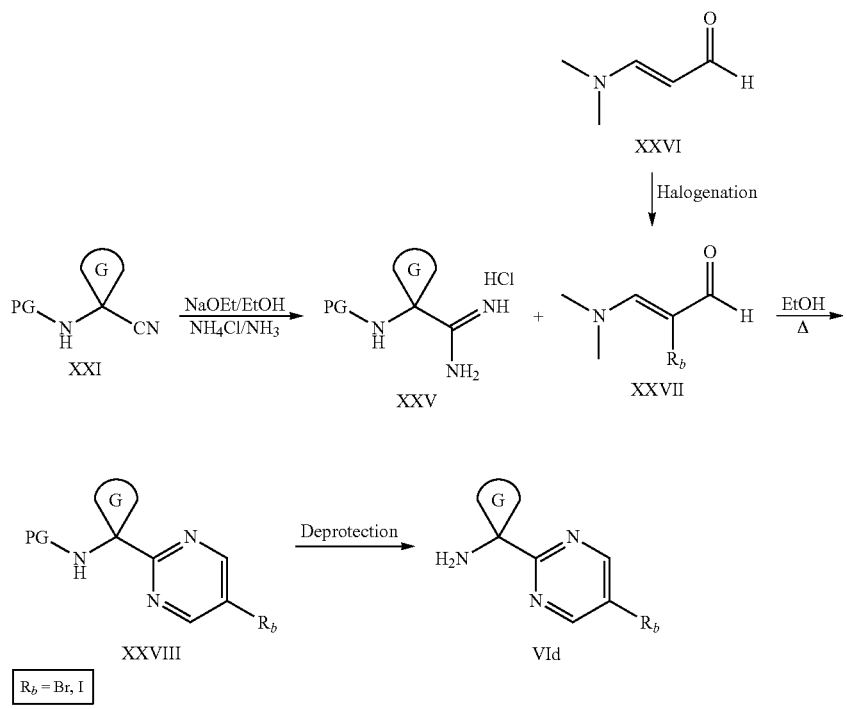

As illustrated in Scheme IX, a suitably protected amino carbonitrile of formula XXI wherein PG is a suitable protecting group such as Boc may be converted to the corresponding amidine hydrochloride XXV via reaction with suitable reagents such as sodium ethoxide in ethanol followed by treatment with ammonium chloride and ammonia. In a separate synthetic transformation, 3-dimethylaminopropenal XXVI may be halogenated with a suitable reagent (e.g., Br$_2$ and NIS) in a suitable solvent such as CHCl$_3$ to afford a 2-halogen-substituted 3-dimethylaminopropenal of formula XXVII (i.e., R$_b$ is Br or I). Subsequently, an amidine hydrochloride XXV may be reacted with a compound of formula XXVII in a suitable solvent (e.g., EtOH) and at a suitable temperature (e.g., at about 80° C.) to provide a pyrimidine of formula XXVIII. A compound XXVIII may be N-deprotected using conditions well-known in the art and as described above to afford an intermediate of formula VId.

Suitably protected amino acid of the formula XV, which may be used in the synthesis of intermediates of formula VI are either commercially available, may be prepared according to the reference described below (hereby incorporated by reference in its entirety), or may be prepared by one skilled in the art using methods described in the chemical literature.

3-tert-butoxycarbonylamino-oxetane-3-carboxylic acid may be synthesized according to the procedure described in patent application WO 2009/070485 A1.

The following are examples of unnatural amino acids that are commercially available. These Examples are for the pur-

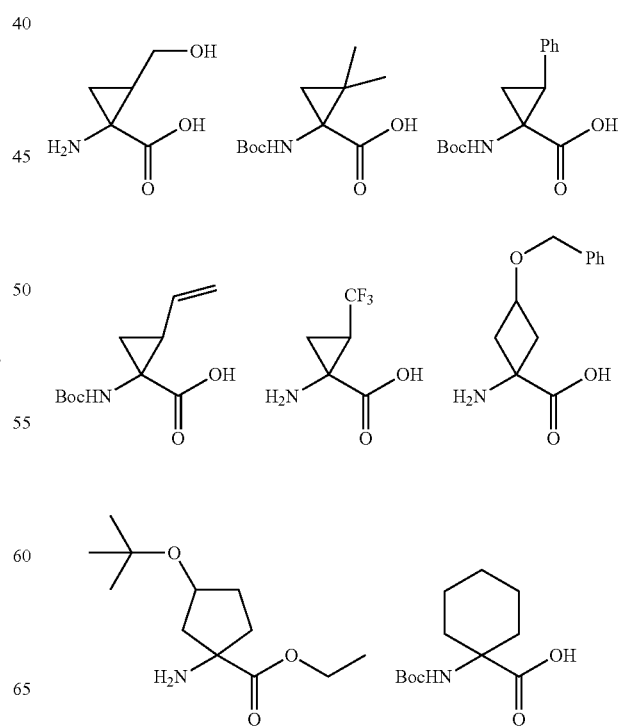

-continued

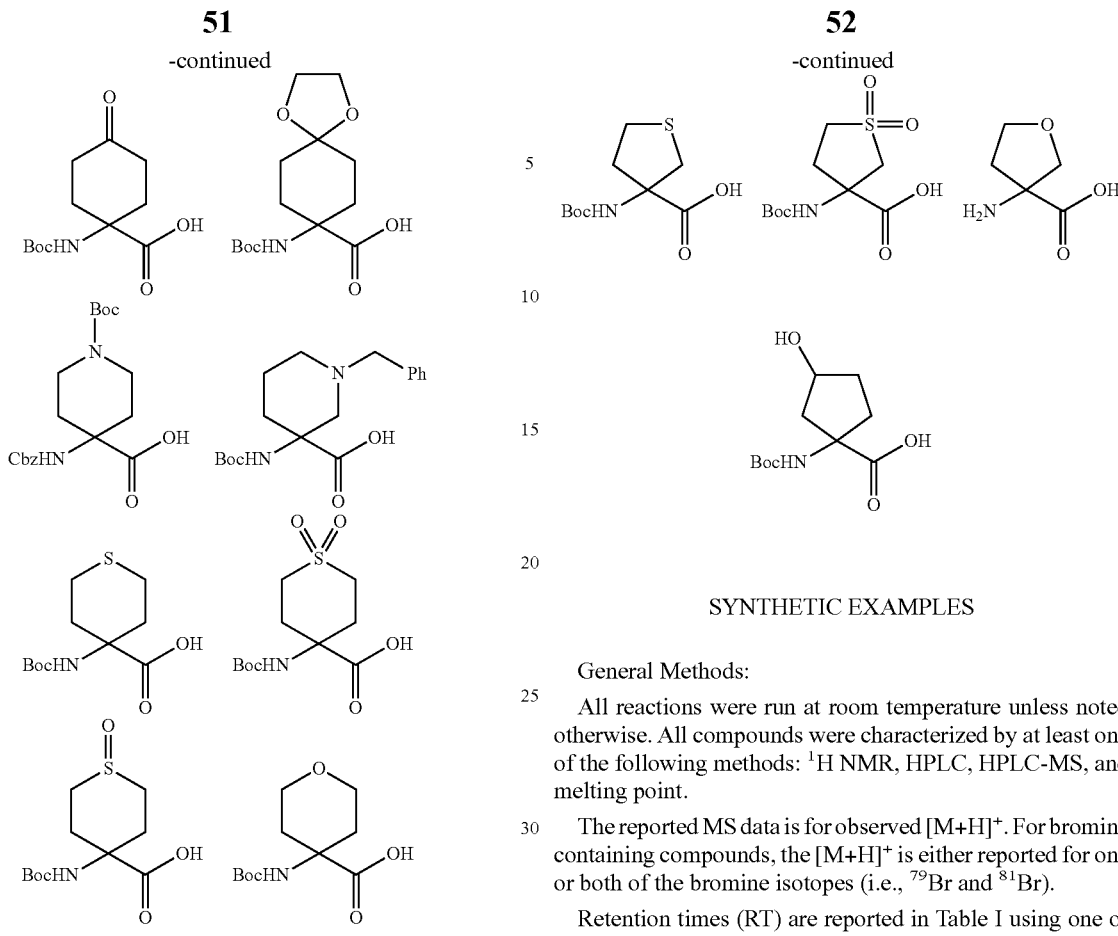

SYNTHETIC EXAMPLES

General Methods:

All reactions were run at room temperature unless noted otherwise. All compounds were characterized by at least one of the following methods: $^1$H NMR, HPLC, HPLC-MS, and melting point.

The reported MS data is for observed $[M+H]^+$. For bromine containing compounds, the $[M+H]^+$ is either reported for one or both of the bromine isotopes (i.e., $^{79}$Br and $^{81}$Br).

Retention times (RT) are reported in Table I using one of the following methods:

| HPLC Method | Time (min) | Mobile Phase H$_2$O (0.1% FA) | CH$_3$CN (0.1% FA) | Flow (mL/min) | Column |
|---|---|---|---|---|---|
| A1 | 0 | 95 | 5 | 2.5 | Agilent Zorbax C18 SB |
|  | 1.7 | 5 | 95 | 2.5 | 3.5 um 4.6 × 30 mm cartridge |
|  | 2 | 5 | 95 | 2.5 |  |
|  | 2.1 | 95 | 5 | 2.5 |  |
|  | 2.3 | 95 | 5 | 2.5 |  |
| B1 | 0 | 70 | 30 | 2.5 | Agilent Zorbax C18 SB |
|  | 1.7 | 5 | 95 | 2.5 | 3.5 um 4.6 × 30 mm cartridge |
|  | 2 | 5 | 95 | 2.5 |  |
|  | 2.1 | 70 | 30 | 2.5 |  |
|  | 2.3 | 70 | 30 | 2.5 |  |
| C1 | 0 | 99 | 1 | 2.5 | Agilent Zorbax C18 SB |
|  | 1.7 | 50 | 50 | 2.5 | 3.5 um 4.6 × 30 mm cartridge |
|  | 2 | 5 | 95 | 2.5 |  |
|  | 2.1 | 5 | 95 | 2.5 |  |
|  | 2.3 | 99 | 1 | 2.5 |  |
| D1 | 0 | 95 | 5 | 1.5 | Agilent Zorbax Eclipse |
|  | 7 | 5 | 95 | 1.5 | XDB-C8 5 um 4.6 × 150 mm |
|  | 9 | 5 | 95 | 1.5 |  |
|  | 9.3 | 95 | 5 | 1.5 |  |
|  | 10 | 95 | 5 | 1.5 |  |
| C2 | 0 | 99 | 1 | 2.5 | Agilent Zorbax C18 SB |
|  | 1.6 | 80 | 20 | 2.5 | 3.5 um 4.6 × 30 mm cartridge |
|  | 1.7 | 5 | 95 | 2.5 |  |
|  | 2 | 5 | 95 | 2.5 |  |
|  | 2.1 | 99 | 1 | 2.5 |  |
|  | 2.3 | 99 | 1 | 2.5 |  |
| D2 | 0 | 99 | 1 | 1.5 |  |
|  | 2 | 80 | 20 | 1.5 | Agilent Zorbax Eclipse |
|  | 7 | 5 | 95 | 1.5 | XDB-C8 5 um 4.6 × 150 mm |
|  | 9 | 5 | 95 | 1.5 | column |
|  | 9.3 | 99 | 1 | 1.5 |  |
|  | 10 | 99 | 1 | 1.5 |  |

-continued

| HPLC Method | Time (min) | Mobile Phase | | Flow (mL/min) | Column |
|---|---|---|---|---|---|
| | | H₂O (0.1% FA) | CH₃CN (0.1% FA) | | |
| A3 | 0 | 88 | 12 | 1.5 | Agilent SB-C18 1.8 um 3 × 50 mm column |
| | 0.25 | 70 | 30 | 1.5 | |
| | 0.3 | 60 | 40 | 1.5 | |
| | 1.19 | 5 | 95 | 1.5 | |
| | 1.75 | 0 | 100 | 1.5 | |
| B3 | 0 | 60 | 40 | 1.5 | Agilent Eclipse C8 1.8 um 3 × 50 mm column |
| | 1.19 | 15 | 85 | 1.5 | |
| | 1.75 | 0 | 100 | 1.5 | |
| C3 | 0 | 95 | 5 | 1.5 | Agilent SB-AQ 1.8 um 3 × 50mm column |
| | 0.25 | 50 | 50 | 1.5 | |
| | 0.3 | 70 | 30 | 1.5 | |
| | 1.3 | 10 | 90 | 1.5 | |
| | 1.7 | 0 | 100 | 1.5 | |
| D3 | 0 | 95 | 5 | 1.5 | Agilent SB-C18 1.8 um 3 × 50 mm column |
| | 3.8 | 10 | 90 | 1.5 | |
| | 4.5 | 0 | 100 | 1.5 | |

| HPLC Method | Time (min) | Mobile Phase | | Flow (mL/min) | Column |
|---|---|---|---|---|---|
| | | 95% H₂O + 5% CH₃CN (0.05% Formic Acid) | CH₃CN (0.05% Formic Acid) | | |
| E | 0 | 90 | 10 | 0.8 | BEH 2.1 × 50 mm C18, 1.7 um particle diameter |
| | 1.19 | 5 | 95 | 0.8 | |
| | 1.7 | 5 | 95 | 0.8 | |

Synthesis of Intermediates

Syntheses of the following heteroaryl-cyclopropylamine intermediates or their corresponding salt forms are described in patent application WO 2009/070485 A1:

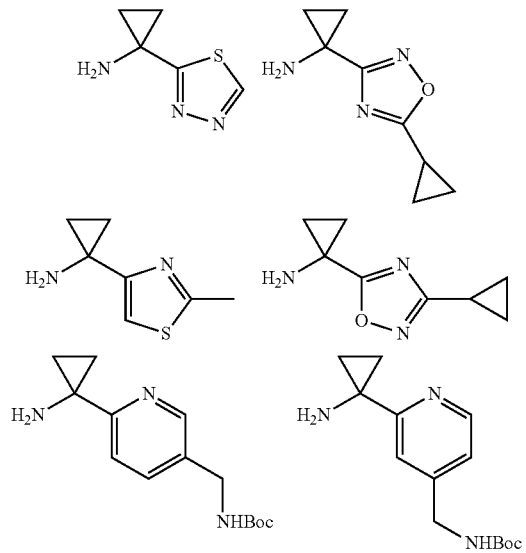

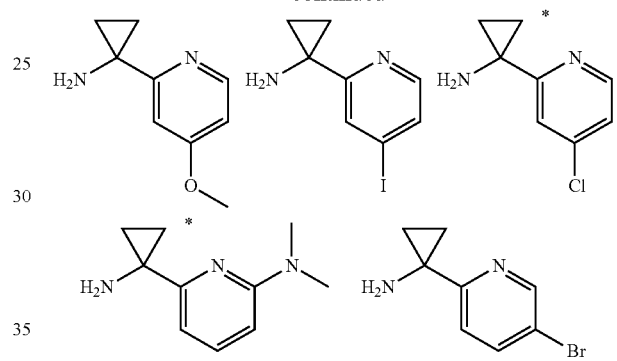

*Intermediate may be prepared using appropriate reagents and according to the procedure described in the reference for a related analog.

Example 1

Synthesis of 1-(4-fluorophenyl)-1H-pyrazolo[3,4-c]pyridine-4-carboxylic acid (1)

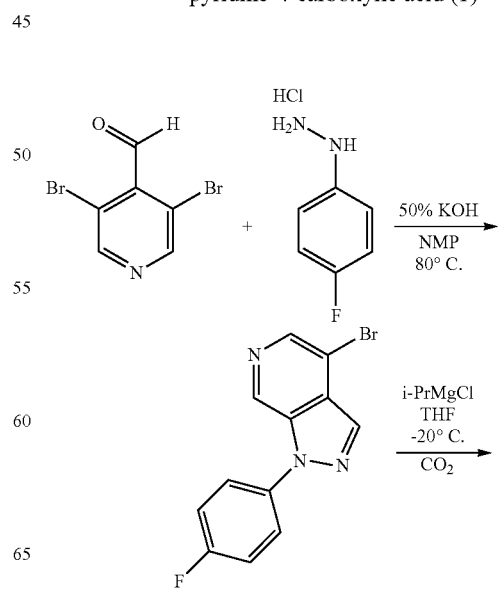

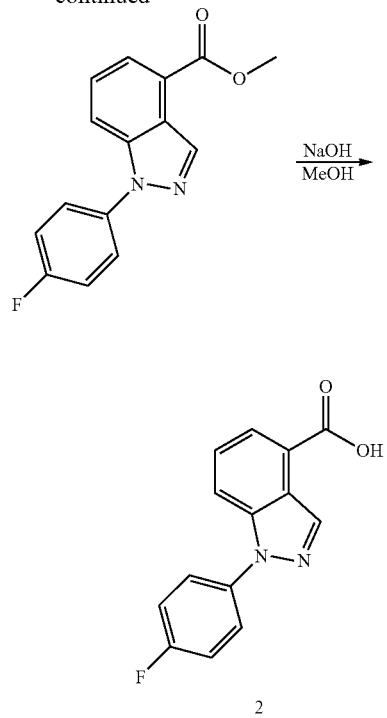

To a 1 L flask is charged 3,5-dibromopyridine-4-carboxaldehyde (50.0 g, 189 mmol, 1.0 eq) and 4-fluorophenylhydrazine hydrochloride (31.0 g, 191 mmol, 1.01 eq). NMP (250 mL) is charged, and the resulting slurry is stirred at ambient temperature for 2 hours. A solution of aqueous KOH is prepared from 85% KOH pellets (27.4 g, 415 mmol, 2.2 eq) and water (27.4 mL), and this KOH solution is charged to the reaction mixture. The batch is heated to 80° C. and is held at this temperature for 30-60 minutes. Water (250 mL) is then charged at 80° C., and the resulting slurry is cooled to ambient temperature over 4-16 hours. The slurry is filtered, the solid is washed with water, and oven dried under vacuum to afford 4-bromo-1-(4-fluorophenyl)-1H-pyrazolo[3,4-c]pyridine as a solid.

To a 1 L flask is charged 4-bromo-1-(4-fluorophenyl)-1H-pyrazolo[3,4-c]pyridine (50.0 g, 171 mmol, 1 eq) and THF (300 mL). The slurry is cooled to −20° C. i-PrMgCl solution (128.2 mL, 256.4 mmol, 2.0 M in THF, 1.5 eq) is charged at a rate to keep the temperature below −10° C. The reaction is held at −10° C. for 3 hours. $CO_2$ gas is bubbled into the reaction mixture until the temperature increase peak, and the temperature begins to drop. The temperature is adjusted to 22° C., and i-PrOAc (325 mL) is added. A solution of aqueous HCl is prepared from concentrated HCl (55 mL) and water (195 mL). About 10 mL of this HCl solution is charged to the reaction mixture to achieve pH 6-7. The mixture is then heated to 55° C., and the remaining ~240 mL of the HCl solution is charged. The reaction is cooled to ambient temperature over 1 hour, held at this temperature for 1 hour, and filtered. The solid is washed with water and i-PrOAc, oven dried under vacuum to afford the title compound as a solid.

Example 2

Synthesis of 1-(4-fluoro-phenyl)-1H-indazole-4-carboxylic acid (2)

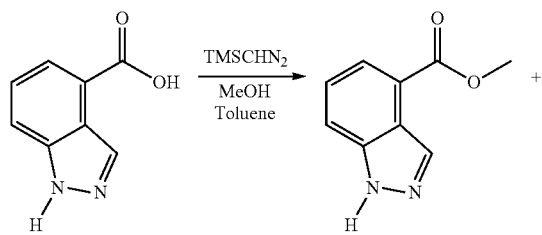

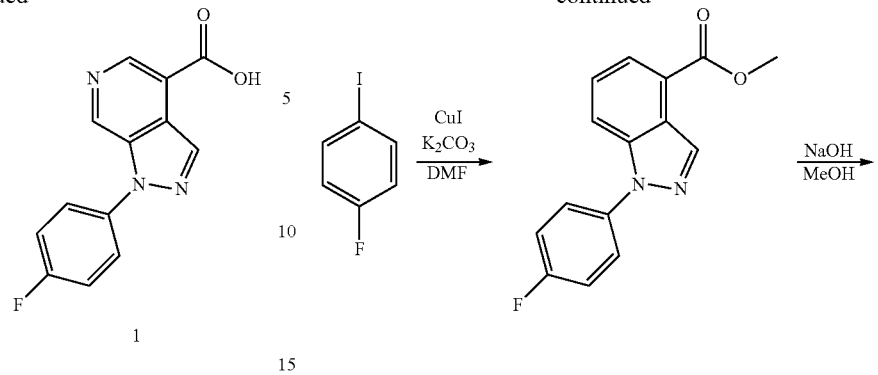

Indazole-4-carboxylic acid (2.00 g, 12.3 mmol) is suspended in methanol (20 mL) and toluene (30 mL) at room temperature. A solution of 2M trimethylsilyl diazomethane (12 mL, 24 mmol) in toluene is added slowly and the mixture is stirred at room temperature until the solution turned yellow. The reaction is quenched with concentrated acetic acid (5 mL) and the solvent is removed in vacuo. The residue is purified by silica gel chromatography eluting with a gradient of 0-30% ethyl acetate in hexanes to afford 1H-indazole-4-carboxylic acid methyl ester.

A mixture of 1H-indazole-4-carboxylic acid methyl ester (5.0 g, 28 mmol), copper iodide (5.7 g, 3.0 mmol), potassium carbonate (4.15 g, 30.0 mmol) and 4-fluoroiodobenzene (3.47 g, 30.0 mmol) is charged in a sealed tube at room temperature. The tube is evacuated, back-filled with argon and dimethylformamide (20 mL) is added followed by rac-trans-N,N'-dimethylcyclohexane-1,2-diamine (0.93 g, 6.5 mmol). The solution is stirred at 120° C. for 3 hours, then cooled to room temperature and diluted with water (50 mL) and ethyl acetate (80 mL). The organic layer is separated, washed with brine (30 mL), and dried over sodium sulfate. The crude product is filtered, concentrated and purified by silica gel chromatography eluting with a gradient of 0-30% ethyl acetate in hexanes to afford 1-(4-fluoro-phenyl)-1H-indazole-4-carboxylic acid methyl ester.

To a stirred solution of 1-(4-fluoro-phenyl)-1H-indazole-4-carboxylic acid methyl ester (2.0 g, 7.4 mmol) in water (20 mL) and methanol (20 mL) is added a solution of 2N sodium hydroxide (10 mL). The solution is warmed at reflux for 1 hour. The solution is cooled to room temperature and acidified to pH 3-4 with 1N aqueous HCl. The mixture is filtered, and the resulting solid is washed with MeOH (30 mL) and dried to afford 1-(4-fluoro-phenyl)-1H-indazole-4-carboxylic acid.

Example 3

Synthesis of 1-(6-bromo-pyridin-3-yl)-cyclopropylamine bistrifluoroacetic acid salt (3)

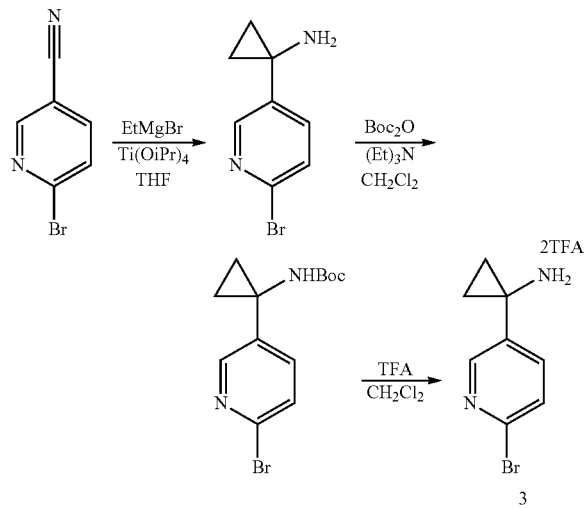

An oven dried 2 L round-bottom flask equipped with a mechanical stirrer is charged with anhydrous THF (750 mL) followed by Ti(Oi-Pr)$_4$ (72.8 mL, 246 mmol) under Ar atmosphere. The solution is purged under Ar and heated to 50° C. 6-Bromo-nicotinonitrile (30.0 g, 164 mmol) is added to the mixture followed by dropwise addition (over 40 minutes) of 1M solution of ethylmagnesium bromide in THF (410 mL, 410 mmol). The reaction is allowed to stir at 50° C. After 3 hours, the reaction mixture is cooled to room temperature and a 3M aqueous solution of HCl (approx 350 mL) is added. The mixture is transfered to a separatory funnel and is washed with ethyl ether (3×500 mL). The aqueous layer is allowed to stand overnight. The aqueous layer is then basified to pH 10 with 2M aqueous solution of NaOH. The solution is diluted with EtOAc (500 mL) and the resulting solution is vigorously stirred for 5 minutes. The solution is allowed to stand while the layers slowly separated. The organic layer is decanted and the same extraction process is repeated twice. The organic layers are combined, washed with brine (50 mL), dried over MgSO$_4$ and concentrated in vacuo to yield an oil. The crude oil is purified by silica gel chromatography using a gradient of 0-10% MeOH in CH$_2$Cl$_2$ to afford 1-(6-bromo-pyridin-3-yl)-cyclopropylamine as an oil, which slowly crystallizes (ES+ m/z 213.3, 215.3).

1-(6-bromo-pyridin-3-yl)-cyclopropylamine (1.16 g, 4.60 mmol) is dissolved in CH$_2$Cl$_2$ (20 mL). Et$_3$N (0.78 mL, 5.6 mmol) and Boc$_2$O (1.11 g, 5.10 mmol) are added sequentially and the reaction is stirred at room temperature. After 20 hours, the reaction is diluted with CH$_2$Cl$_2$ (20 mL) and water (20 mL) and the layers are separated. The aqueous layer is extracted with CH$_2$Cl$_2$ (100 mL). The combined CH$_2$Cl$_2$ layers are washed with brine, dried over MgSO$_4$, filtered and concentrated to afford [1-(6-bromo-pyridin-3-yl)-cyclopropyl]-carbamic acid tert-butyl ester as a solid.

[1-(6-bromo-pyridin-3-yl)-cyclopropyl]-carbamic acid tert-butyl ester (0.800 g, 2.55 mmol) is dissolved in CH$_2$Cl$_2$ (10 mL). TFA (5 mL) is added dropwise. After 4 hours, the reaction is concentrated in vacuo to afford the title compound as an oil (ES+ m/z 213.1, 215.1).

Example 4

Synthesis of 1-(5-bromo-pyrimidin-2-yl)-cyclopropylamine dihydrochloride (4)

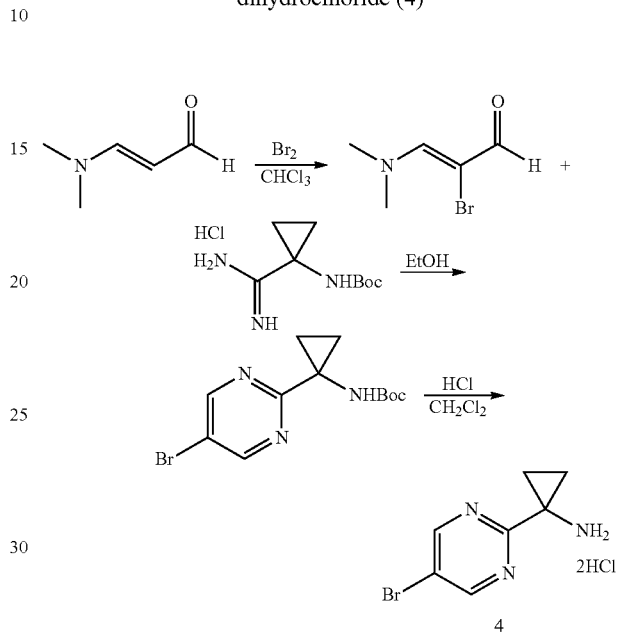

3-Dimethylamino-propenal (50 mL, 500 mmol) is dissolved in CHCl$_3$ (400 mL) at room temperature. Bromine (25.7 mL, 0.500 mol) is added neat via syringe over 5 minutes. After 30 minutes, the reaction is poured into a mixture of 200 mL saturated aqueous Na$_2$S$_2$O$_3$ and 200 mL saturated aqueous NaHCO$_3$, and the mixture is extracted with CH$_2$Cl$_2$ (3×100 mL). The combined organic layers are dried over MgSO$_4$ and concentrated to give a solid. The solid is dissolved in EtOAc (200 mL), insoluble materials are filtered off, the filtrate is concentrated in vacuo and the resulting solid is washed with a solution of 50% EtOAc in hexanes to afford 3-dimethylamino-2-bromo-propenal as a solid (ES+ m/z 178.28).

(1-Carbamimidoyl-cyclopropyl)-carbamic acid tert-butyl ester hydrochloride (1.0 g, 4.2 mmol) (prepared according to the procedure described in patent application WO 2009/070485 A1) and 3-dimethylamino-2-bromo-propenal (1.1 g, 6.4 mmol) are added to EtOH (2 mL) in a pressure tube. The reaction vessel is capped and the mixture is heated at 80° C. for 24 hours. The mixture is cool to room temperature and methanol (20 mL) is added. The resulting solids are filtered and the filtrate is concentrated in vacuo. The residue is dissolved with CH$_2$Cl$_2$ (50 mL) and the solids are filtered. The filtrate is concentrated and the residue is purified by silica gel chromatography using a gradient of 0-50% EtOAc in hexanes to afford [1-(5-bromo-pyrimidin-2-yl)-cyclopropyl]-carbamic acid tert-butyl ester as a solid.

[1-(5-Bromo-pyrimidin-2-yl)-cyclopropyl]-carbamic acid tert-butyl ester (1.18 g, 3.76 mmol) is dissolved in CH$_2$Cl$_2$ (5 mL) at room temperature. A 4M solution of HCl in dioxane (9.4 mL, 38 mmol) is added. After 2 hours, solvents are

Example 5

Synthesis of [1-(5-iodo-furan-2-yl)-cyclopropyl]-carbamic acid tert-butyl ester (5)

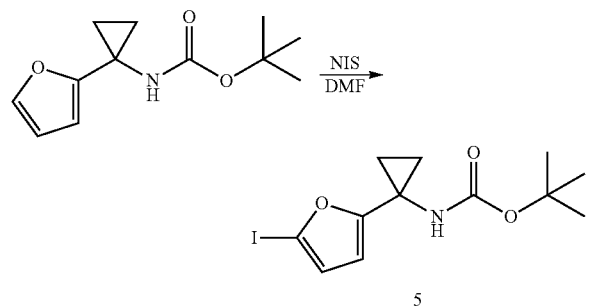

To a solution of (1-furan-2-yl-cyclopropyl)-carbamic acid tert-butyl ester (4.30 g, 19.3 mmol) (prepared according to the procedure described in patent application WO 2009/070485 A1) in anhydrous DMF (77 mL) at room temperature is added solid N-iodosuccinimide (4.77 g, 21.2 mmol) in one portion. After 2.5 hours, the reaction is diluted with a saturated aqueous solution of $Na_2S_2O_3$ (75 mL), water (75 mL), and ethyl ether (100 mL). Phases are separated and the aqueous layer is extracted with ethyl ether (2×100 mL). The combined organic layers are dried over $Na_2SO_4$ and concentrated. The resultant solid is triturated with hexanes to afford the title compound as a powder (ES+ m/z 350.5).

Example 6

Synthesis of 3-(1-amino-cyclopropyl)-benzoic acid methyl ester (6)

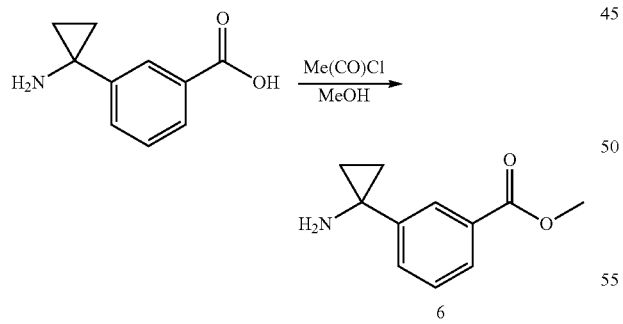

Acetyl chloride (0.600 mL, 8.46 mmol) is added to methanol (15 mL) at 0° C. and the solution is warmed to room temperature. After stirring for 20 minutes, 3-aminocyclopropyl benzoic acid (0.500 g, 2.82 mmol) is added and the reaction mixture is heated at reflux. After 16 hours, the mixture is concentrated at 65° C. under a stream of nitrogen. The residue is neutralized with saturated aqueous sodium bicarbonate (50 mL) and extracted with ethyl acetate (3×50 mL). The combined organic layers are washed with brine (100 mL), dried over $MgSO_4$, filtered and concentrated to afford crude title product, which is used without purification.

Example 7

Synthesis of 1-(2-bromo-pyridin-4-yl)-cyclopropylamine trifluoroacetic acid salt (7)

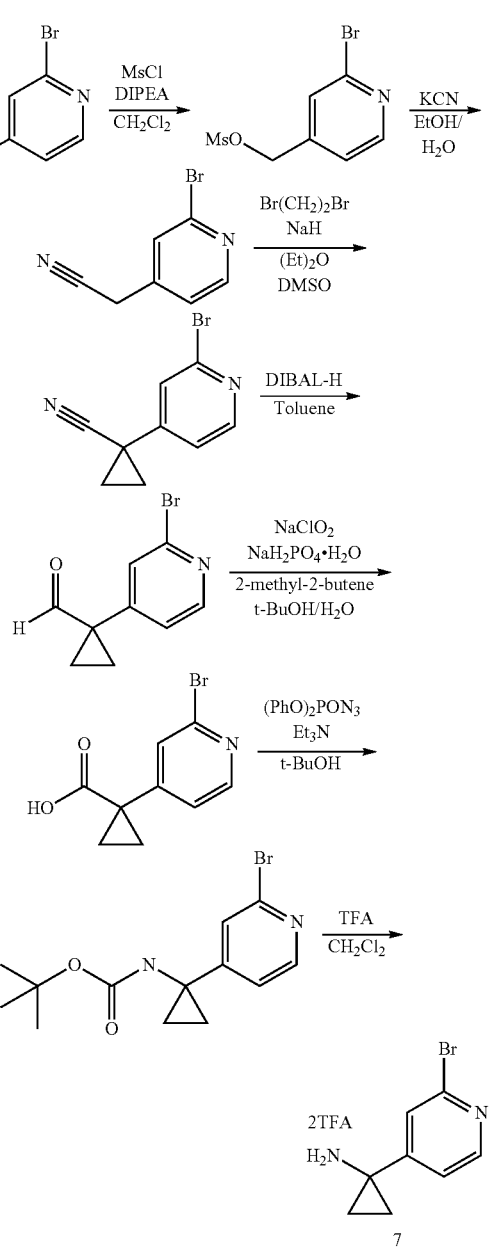

To a stirred 0° C. solution of (2-bromo-pyridin-4-yl)-methanol (3.00 g, 16.0 mmol) and N,N-diisopropylethylamine (8.3 mL, 48 mmol) in dichloromethane (30 mL) is added methanesulfonyl chloride (1.30 mL, 16.8 mmol). The resulting mixture is warmed to room temperature. After 1 hour, the mixture is diluted with dichloromethane (20 mL) and washed with saturated aqueous ammonium chloride (3×10 mL), saturated aqueous sodium bicarbonate (10 mL), brine (10 mL), dried over MgSO₄, filtered and concentrated to afford crude methanesulfonic acid 2-bromo-pyridin-4-ylmethyl ester, which is used without purification.

Methanesulfonic acid 2-bromo-pyridin-4-ylmethyl ester (4.24 g, 15.9 mmol) is added to a stirred solution of potassium cyanide (1.02 g, 15.1 mmol) in a mixture of ethanol (30 mL) and water (6 mL) at room temperature. After 72 hours, ethyl acetate (80 mL) and saturated aqueous sodium bicarbonate (40 mL) are added and phases are separated. The organic layer is washed with water (3×40 mL), dried over MgSO₄, filtered and concentrated. The resulting residue is purified by silica gel chromatography eluting with a gradient of 0-60% ethyl acetate in heptane to afford (2-bromo-pyridin-4-yl)-acetonitrile (ES+ m/z 197.41; 199.40).

A solution of (2-bromo-pyridin-4-yl)-acetonitrile (1.20 g, 6.09 mmol) and the 1,2-dibromoethane (0.663 mL, 7.61 mmol) in a mixture of dry Et₂O (5 mL) and dry DMSO (1 mL) is added to a suspension of NaH (60% dispersion in mineral oil, 585 mg, 14.6 mmol) in dry DMSO (10 mL) while controlling the resulting exotherm by cooling in a water bath, and the resulting mixture is stirred at room temperature. After 18 hours, water (10 mL) and ethyl acetate (10 mL) are added, phases are separated and the aqueous layer is extracted with ethyl acetate (3×10 mL). The combined organic layers are washed with brine (30 mL) and dried over MgSO₄, filtered and concentrated. The residue is purified on SiO₂ eluting with a gradient of 0-60% ethyl acetate in heptane to afford 1-(2-bromo-pyridin-4-yl)-cyclopropanecarbonitrile as a solid (ES+ m/z 223.36; 225.39).

To a solution of 1-(2-bromo-pyridin-4-yl)-cyclopropanecarbonitrile (1.16 g, 5.20 mmol) in toluene (30 mL) is added DIBAL-H (10.4 mL, 1M in toluene) at −78° C. The mixture is stirred 1 hour at −78° C. and warmed to room temperature. After 1 hour, ethyl acetate (30 mL) is added, followed by 1M aqueous solution of H₂SO₄ (30 mL). Phases are separated and the aqueous layer is extracted with ethyl acetate (3×50 mL). The combined organic layers are dried over MgSO₄, filtered and concentrated to afford crude 1-(2-bromo-pyridin-4-yl)-cyclopropanecarbaldehyde (ES+ m/z 226.48; 228.47), which is used without purification.

A solution of sodium chlorite (368 mg, 3.26 mmol) and sodium dihydrogen phosphate monohydrate (449 mg, 3.26 mmol) in 5 mL of water is added dropwise to a solution of crude 1-(2-bromo-pyridin-4-yl)-cyclopropanecarbaldehyde (566 mg, 2.50 mmol) and 2-methyl-2-butene (1.73 mL, 16.3 mmol) in tert-butanol (12 mL), and the resulting reaction mixture is stirred at room temperature. After 18 hours, the mixture is concentrated in vacuo, acidified to pH 2 with 1M aqueous solution of HCl, diluted with brine (25 mL) and extracted with ethyl acetate (3×50 mL). The combined organic layers are dried over Na₂SO₄, filtered and concentrated to afford crude 1-(2-bromo-pyridin-4-yl)-cyclopropanecarboxylic acid, which is used without purification.

To a solution of crude 1-(2-bromo-pyridin-4-yl)-cyclopropanecarboxylic acid (0.350 g, 1.45 mmol) in tert-butanol (7 mL) in a pressure vessel is added diphenylphosphoryl azide (0.312 mL, 1.45 mmol) and triethylamine (0.202 mL, 1.45 mmol). The tube is sealed and the reaction mixture is stirred at 90° C. After 4 hours, the pressure vessel is cooled in an ice-bath, vented and opened. The reaction mixture is concentrated in vacuo. The resulting residue is dissolved in ethyl acetate (70 mL), washed with saturated aqueous ammonium chloride (70 mL) and saturated aqueous sodium bicarbonate (70 mL), dried over MgSO₄, filtered and concentrated. The residue is purified by silica gel chromatography eluting with a gradient of 0-50% ethyl acetate in heptane to afford [1-(2-bromo-pyridin-4-yl)-cyclopropyl]-carbamic acid tert-butyl ester.

To a stirred solution of [1-(2-bromo-pyridin-4-yl)-cyclopropyl]-carbamic acid tert-butyl ester (0.160 g, 0.511 mmol) in dichloromethane (3 mL) is added trifluoroacetic acid (1.0 mL, 13 mmol) at room temperature. After 18 hours, the reaction mixture is concentrated in vacuo to yield crude title compound (ES+ m/z 213.49, 215.40) as an oil, which is used without purification.

Example 8

Synthesis of
1-(2-bromo-pyridin-4-yl)-cyclobutylamine
trifluoroacetic acid salt (8)

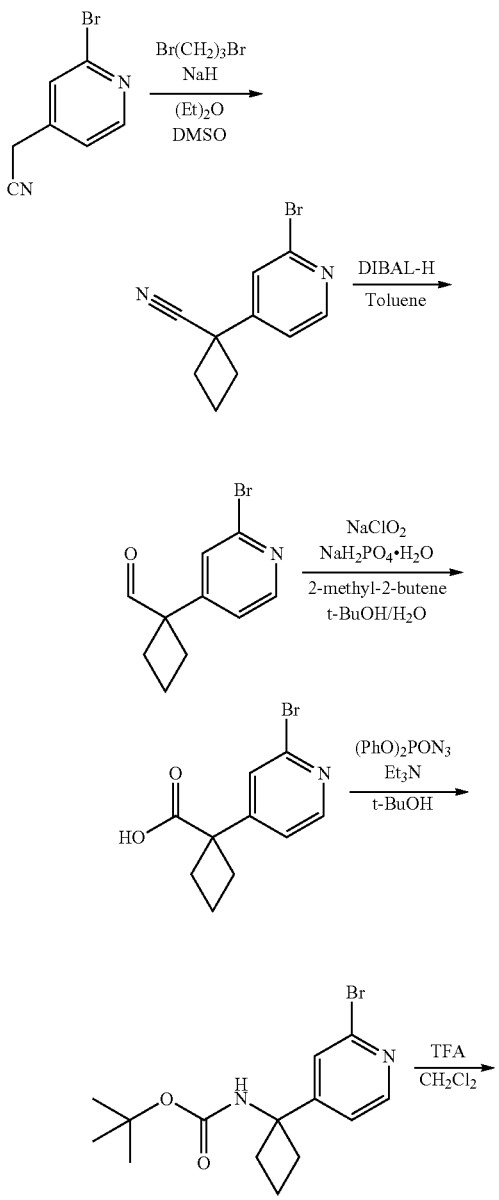

-continued

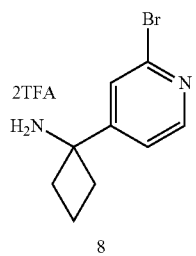
8

1-(2-Bromo-pyridin-4-yl)-cyclobutanecarbonitrile is prepared from (2-bromo-pyridin-4-yl)-acetonitrile (1.50 g, 7.61 mmol) according to the cycloalkylation procedure described in Example 7 using 1,3-dibromopropane instead of 1,2-dibromoethane. 1-(2-Bromo-pyridin-4-yl)-cyclobutanecarbaldehyde is prepared from 1-(2-bromo-pyridin-4-yl)-cyclobutanecarbonitrile (1.26 g, 5.20 mmol) according to the DIBAL-H procedure described in Example 7.

1-(2-Bromo-pyridin-4-yl)-cyclobutanecarboxylic acid (ES+ m/z 256.40, 258.38) is prepared from 1-(2-bromo-pyridin-4-yl)-cyclobutanecarbaldehyde (532 mg, 2.22 mmol) according to the oxidation procedure described in Example 7.

[1-(2-Bromo-pyridin-4-yl)-cyclobutyl]-carbamic acid tert-butyl ester (ES+ m/z 327.54, 329.46) is prepared from 1-(2-bromo-pyridin-4-yl)-cyclobutanecarboxylic acid (0.100 g, 0.390 mmol) according to the Curtius Rearrangement procedure described in Example 7 using a reaction temperature of 100° C.

The title compound (ES+ m/z 227.30, 229.27) is prepared from [1-(2-bromo-pyridin-4-yl)-cyclobutyl]-carbamic acid tert-butyl ester (82.0 mg, 0.262 mmol) according to the Boc-deprotection procedure described in Example 7.

Example 9

Synthesis of 1-(5-methanesulfonyl-furan-2-yl)-cyclopropylamine hydrochloride salt (9)

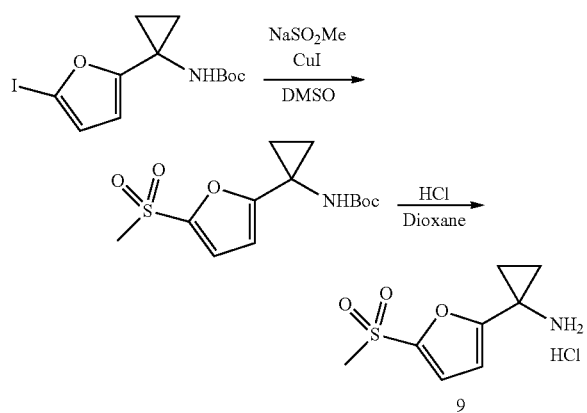

[1-(5-Methanesulfonyl-furan-2-yl)-cyclopropyl]-carbamic acid tert-butyl ester is prepared from [1-(5-iodo-furan-2-yl)-cyclopropyl]-carbamic acid tert-butyl ester (0.500 g, 1.43 mmol) according to the copper (I) iodide-mediated coupling procedure described in Example 19; however, sodium methanesulfinate is used as coupling partner instead of sodium 3-methoxy-3-oxopropane-1-sulfinate.

[1-(5-Methanesulfonyl-furan-2-yl)-cyclopropyl]-carbamic acid tert-butyl ester (0.430 g, 1.42 mmol) is dissolved in a 4M solution of HCl in dioxane (5.0 mL, 20 mmol) at room temperature. After stirring for 16 hours, the mixture is evaporated under a stream of nitrogen. The resulting oily solid is suspended in ethyl acetate (5 mL), ethyl ether (25 mL) is added, and the mixture is filtered to afford crude title product as a solid, which is used without purification.

Synthesis of Compounds of Formula I

Example 10

Synthesis of 1-(4-fluoro-phenyl)-1H-pyrazolo[3,4-c]pyridine-4-carboxylic acid [1-(5-methanesulfonyl-furan-2-yl)-cyclopropyl]-amide (10)

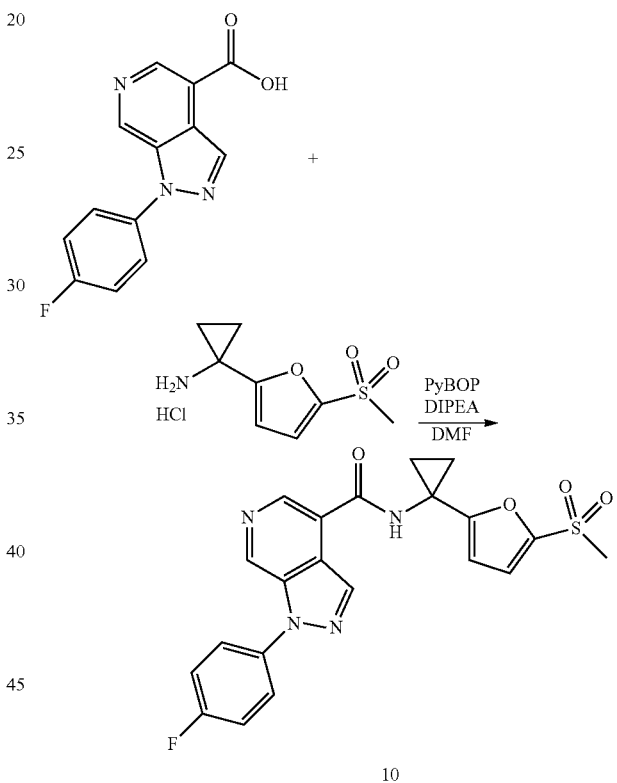

10

To a stirred mixture of 1-(4-fluoro-phenyl)-1H-pyrazolo[3,4-c]pyridine-4-carboxylic acid (0.310 g, 1.21 mmol), N,N-diisopropylethylamine (0.630 mL, 3.62 mmol) and 1-(5-methanesulfonyl-furan-2-yl)-cyclopropylamine-hydrochloride salt (364 mg, 1.53 mmol) in DMF (30 mL) is added (benzotriazol-1-yloxy)tripyrrolidinophosphonium hexafluorophosphate (PyBOP) (0.650 g, 1.25 mmol). After 18 hours, the mixture is diluted with saturated aqueous ammonium chloride (100 mL) and extracted with ethyl acetate (4×30 mL). The combined organic layers are washed with brine (50 mL), dried over sodium sulfate, filtered and concentrated. The residue is purified by silica gel chromatography eluting with a gradient of 0-100% ethyl acetate in hexanes to afford the title compound as a solid.

The following compound is prepared using the coupling method described in Example 10; however, N,N-diisopropylethylamine is replaced with triethylamine:

1-(4-Fluoro-phenyl)-1H-pyrazolo[3,4-c]pyridine-4-carboxylic acid [1-(5-bromo-pyrimidin-2-yl)-cyclopropyl]-amide.

Example 11

Synthesis of 1-(4-fluoro-phenyl)-1H-pyrazolo[3,4-c]pyridine-4-carboxylic acid [1-(2-bromo-pyridin-4-yl)-cyclopropyl]-amide (11)

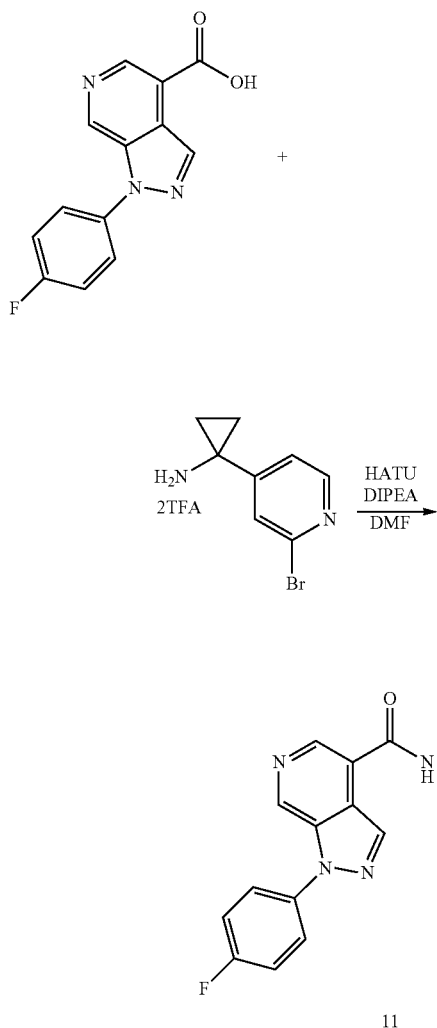

To a mixture of 1-(4-fluoro-phenyl)-1H-pyrazolo[3,4-c]pyridine-4-carboxylic acid (0.120 g, 0.467 mmol) in DMF (2 mL) is added HATU (186 mg, 0.490 mmol). After 30 minutes, N,N-diisopropylethylamine (325 μL, 1.87 mmol) and 1-(2-bromo-pyridin-4-yl)-cyclopropylamine-trifluoroacetic acid salt (223 mg, 0.507 mmol) are added, and the reaction mixture became homogeneous. After 18 hours, the mixture is concentrated in vacuo, reconstituted in ethyl acetate (50 mL) and washed with 1N sodium hydroxide (3×50 mL). The organic layer is washed with saturated aqueous ammonium chloride (2×50 mL), saturated aqueous sodium bicarbonate (50 mL), brine (50 mL), dried over MgSO₄, filtered and concentrated in vacuo. The residue is twice purified by silica gel chromatography eluting with a gradient of 0-10% methanol in methylene chloride to afford the title compound as a solid.

The following compounds are prepared using the coupling method described in Example 11;
1-(4-Fluoro-phenyl)-1H-pyrazolo[3,4-c]pyridine-4-carboxylic acid [1-(6-bromo-pyridin-3-yl)-cyclopropyl]-amide; and
1-(4-Fluoro-phenyl)-1H-pyrazolo[3,4-c]pyridine-4-carboxylic acid (1-pyridin-4-yl-cyclopropyl)-amide.

Example 12

Synthesis of 1-(4-fluoro-phenyl)-1H-pyrazolo[3,4-c]pyridine-4-carboxylic acid (1-1,3,4-thiadiazol-2-yl-cyclopropyl)-amide (12)

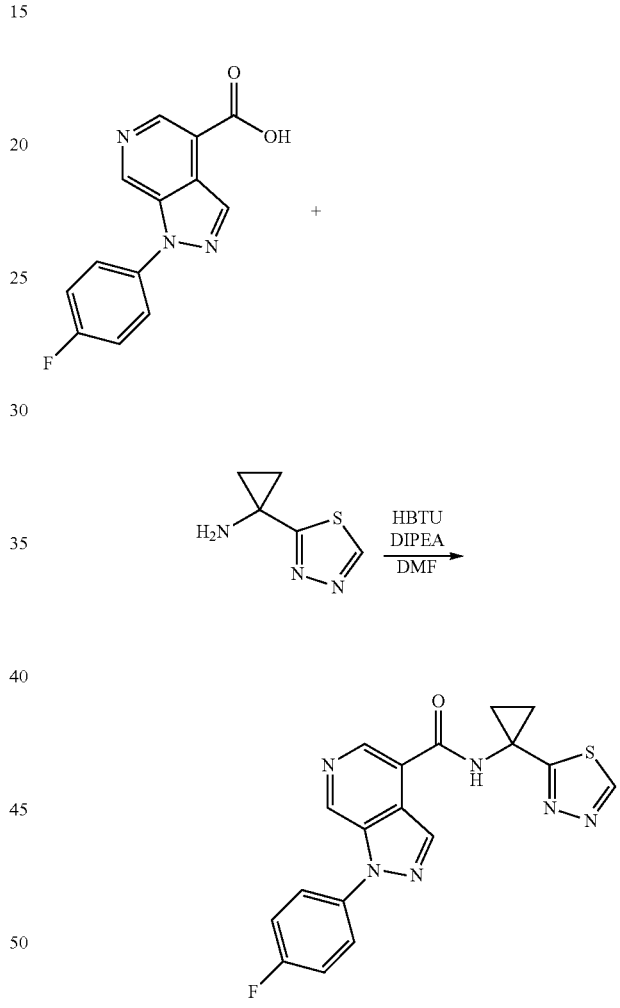

To a suspension of 1-(4-fluoro-phenyl)-1H-pyrazolo[3,4-c]pyridine-4-carboxylic acid (90.0 mg, 0.350 mmol) in DMF (2 mL) is added N,N-diisopropylethylamine (243 μL, 1.40 mmol) and HBTU (159 mg, 0.420 mmol). After 20 minutes, a solution of 1-1,3,4-thiadiazol-2-yl-cyclopropylamine (51.0 mg, 0.361 mmol) in DMF (1 mL) is added and the mixture is stirred at room temperature overnight. The reaction mixture is poured into saturated aqueous sodium bicarbonate (50 mL), ethyl acetate (30 mL) is added and phases are separated. The aqueous layer is treated with brine and extracted with ethyl acetate (3×20 mL). The combined organic layers are concentrated in vacuo. The crude material is purified by silica gel chromatography eluting with a gradient of 0-10% methanol in methylene chloride to afford the title compound as a solid.

Example 13

Synthesis of 1-(4-fluoro-phenyl)-1H-pyrazolo[3,4-c]pyridine-4-carboxylic acid [1-(3-bromo-phenyl)-cyclopropyl]-amide (13)

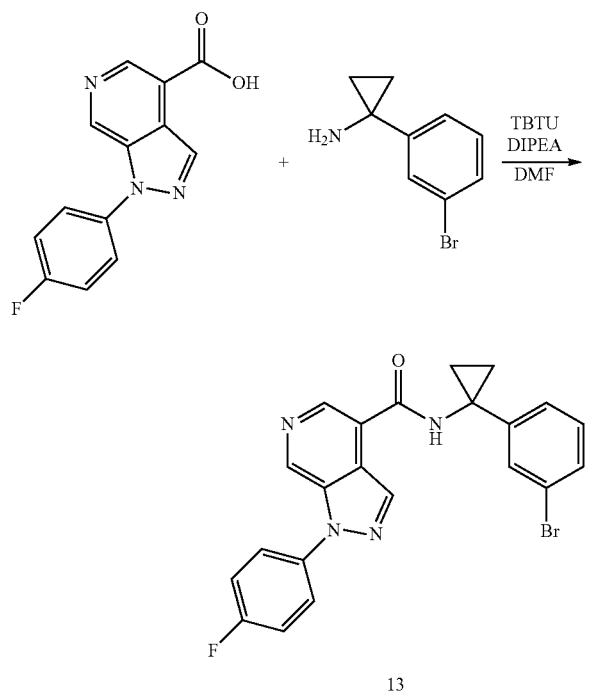

To a solution of 1-(4-fluoro-phenyl)-1H-pyrazolo[3,4-c]pyridine-4-carboxylic acid (0.500 g, 1.94 mmol), 1-(3-bromophenyl)cyclopropanamine (453 mg, 2.14 mmol) and N,N-diisopropylethylamine (1.73 mL, 9.72 mmol) in DMF (18 mL) is added TBTU (0.780 g, 2.43 mmol). After 2 hours, the mixture is concentrated in vacuo, dissolved in ethyl acetate (200 mL), and washed with 2N sodium hydroxide (3×100 mL), saturated aqueous ammonium chloride (2×100 mL), saturated aqueous sodium bicarbonate (100 mL), brine (100 mL). The organic layer is dried over MgSO$_4$, filtered through a pad of silica gel eluting with ethyl acetate (3×100 mL), and concentrated in vacuo. The residue is purified by silica gel chromatography eluting with a gradient of 50-70% ethyl acetate in heptane to give a solid that is triturated with methylene chloride to afford the title compound as a solid.

The following compounds are prepared using the coupling method described in Example 13:

3-(1-{[1-(4-Fluoro-phenyl)-1H-pyrazolo[3,4-c]pyridine-4-carbonyl]-amino}-cyclopropyl)-benzoic acid methyl ester;

1-(4-Fluoro-phenyl)-1H-pyrazolo[3,4-c]pyridine-4-carboxylic acid [1-(2-bromo-pyridin-4-yl)-cyclobutyl]-amide; and 1-(4-Fluoro-phenyl)-1H-indazole-4-carboxylic acid [1-(2-methanesulfonyl-pyridin-4-yl)-cyclopropyl]-amide.

Example 14

Synthesis of 3-(1-{[1-(4-fluoro-phenyl)-1H-pyrazolo[3,4-c]pyridine-4-carbonyl]-amino}-cyclopropyl)-benzoic acid (14)

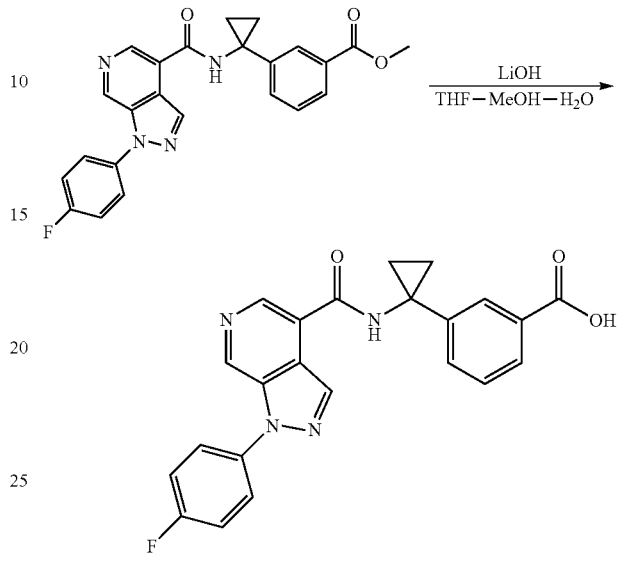

To a solution of 3-(1-{[1-(4-fluoro-phenyl)-1H-pyrazolo[3,4-c]pyridine-4-carbonyl]-amino}-cyclopropyl)-benzoic acid methyl ester (0.650 g, 1.51 mmol) in a mixture of THF/methanol/water (22.5 mL, 3:1:1) is added LiOH.H$_2$O (253 mg, 6.04 mmol). After 3 hours, the reaction mixture is neutralized with glacial acetic acid and concentrated in vacuo. The residue is dissolved in a solution of 20% methanol in methylene chloride (100 mL). Water (100 mL) is added and the mixture is acidified to pH 4 with 2M aqueous hydrochloric acid. Phases are separated, and the aqueous layer is extracted with 20% methanol in methylene chloride (9×100 mL). The combined organic layers are dried over MgSO$_4$, filtered and concentrated to approximately 50 mL. The resulting crystallized solids are filtered, washed with cold methanol (3×2 mL) and air dried to afford the title compound as a solid.

Example 15

Synthesis of [3-(1-{[1-(4-fluoro-phenyl)-1H-pyrazolo[3,4-c]pyridine-4-carbonyl]-amino}-cyclopropyl)-benzoylamino]-acetic acid methyl ester (15)

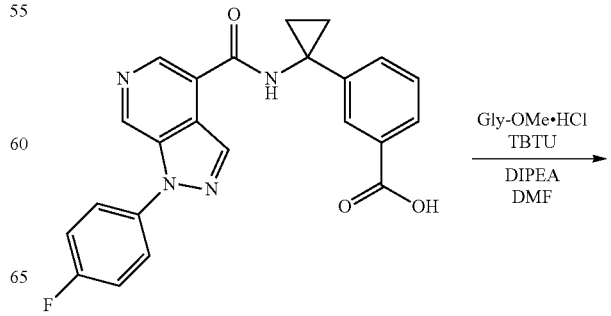

-continued

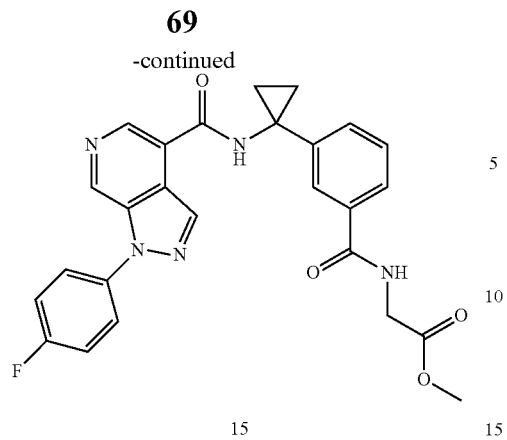

15

To a solution of 3-(1-{[1-(4-fluoro-phenyl)-1H-pyrazolo[3,4-c]pyridine-4-carbonyl]-amino}-cyclopropyl)-benzoic acid (0.200 g, 0.480 mmol), Gly-OMe.HCl (68.1 mg, 0.543 mmol) and N,N-diisopropylethylamine (426 μL, 2.40 mmol) in DMF (4.5 mL) is added TBTU (192 mg, 0.600 mmol). After 4 hours, the mixture is concentrated in vacuo. The residue is dissolved in ethyl acetate (100 mL) and washed with 2N sodium hydroxide (3×50 mL), saturated aqueous ammonium chloride (2×50 mL), saturated aqueous sodium bicarbonate (50 mL), brine (50 mL). The organic layer is dried over MgSO₄, filtered and concentrated. The residue is purified by silica gel chromatography eluting with a gradient of 0-8% methanol in methylene chloride to give a foam, which is triturated with ether (3 mL), filtered, washed with cold ether (3×3 mL) and air dried to afford the title compound.

The following compounds are prepared using the coupling method described in Example 15:

1-[3-(1-{[1-(4-Fluoro-phenyl)-1H-pyrazolo[3,4-c]pyridine-4-carbonyl]-amino}-cyclopropyl)-benzoylamino]-cyclopropanecarboxylic acid methyl ester;

1-(4-Fluoro-phenyl)-1H-pyrazolo[3,4-c]pyridine-4-carboxylic acid {1-[3-(cyanomethyl-carbamoyl)-phenyl]-cyclopropyl}-amide; and (S)-2-[3-(1-{[1-(4-Fluoro-phenyl)-1H-pyrazolo[3,4-c]pyridine-4-carbonyl]-amino}-cyclopropyl)-benzoylamino]-propionic acid methyl ester.

Example 16

Synthesis of 1-(4-fluoro-phenyl)-1H-pyrazolo[3,4-c]pyridine-4-carboxylic acid [1-(3-carbamoyl-phenyl)-cyclopropyl]-amide (16)

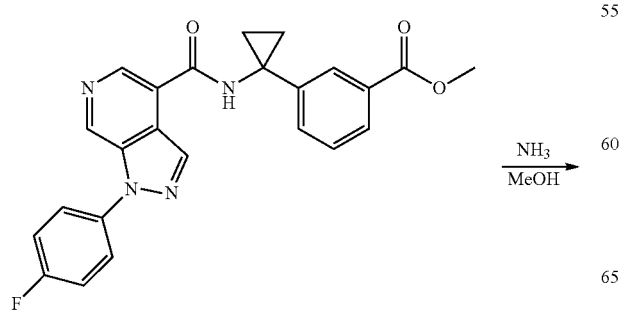

-continued

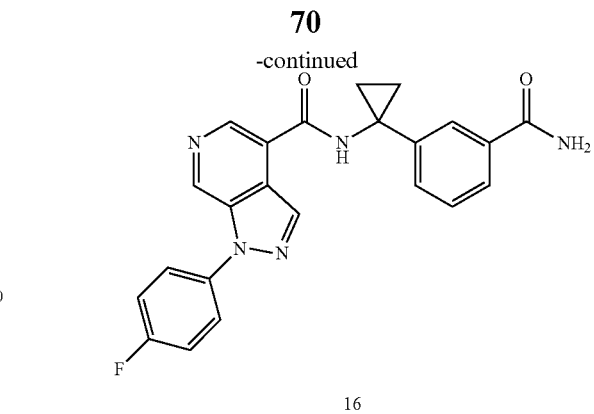

A solution of 3-(1-{[1-(4-fluoro-phenyl)-1H-pyrazolo[3,4-c]pyridine-4-carbonyl]-amino}-cyclopropyl)-benzoic acid methyl ester (70.0 mg, 0.163 mmol) in a 7M solution of ammonia in methanol (1.00 mL, 7.00 mmol) is stirred at 120° C. in a sealed pressure tube. After 78 hours, the reaction vessel is cooled to room temperature, vented and opened. The reaction mixture is concentrated in vacuo, and the resulting residue is purified by silica gel chromatography eluting with a gradient of 0-10% methanol in methylene chloride to afford the title compound a solid.

The following compound is prepared using the method described in Example 16:

1-(4-Fluoro-phenyl)-1H-pyrazolo[3,4-c]pyridine-4-carboxylic acid {1-[3-(carbamoylmethyl-carbamoyl)-phenyl]-cyclopropyl}-amide.

Example 17

Synthesis of 1-(4-fluoro-phenyl)-1H-pyrazolo[3,4-c]pyridine-4-carboxylic acid [1-(3-methylcarbamoyl-phenyl)-cyclopropyl]-amide (17)

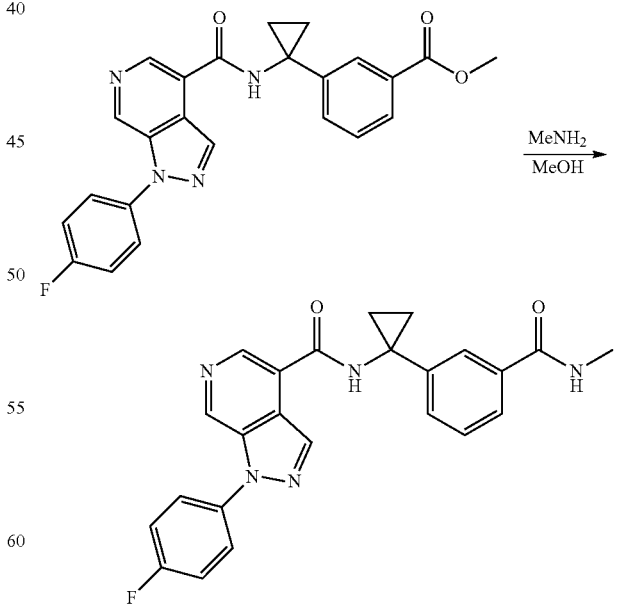

A mixture of 3-(1-{[1-(4-fluoro-phenyl)-1H-pyrazolo[3,4-c]pyridine-4-carbonyl]-amino}-cyclopropyl)-benzoic acid methyl ester (70.0 mg, 0.163 mmol) in a 2M solution of methylamine in methanol (3.0 mL, 6.0 mmol) is stirred at 90° C. in a sealed pressure tube. After 18 hours, the reaction vessel is cooled to room temperature, vented and opened. The reaction mixture is concentrated in vacuo. The residue is purified by silica gel chromatography eluting with a gradient of 0-8% methanol in methylene chloride to afford the title compound as a solid.

The following compound is prepared using the method described in Example 17:
1-(4-Fluoro-phenyl)-1H-pyrazolo[3,4-c]pyridine-4-carboxylic acid {1-[3-(methylcarbamoylmethyl-carbamoyl)-phenyl]-cyclopropyl}-amide.

Example 18

Synthesis of 1-(4-fluoro-phenyl)-1H-pyrazolo[3,4-c]pyridine-4-carboxylic acid [1-(6-methanesulfonyl-pyridin-3-yl)-cyclopropyl]-amide (18)

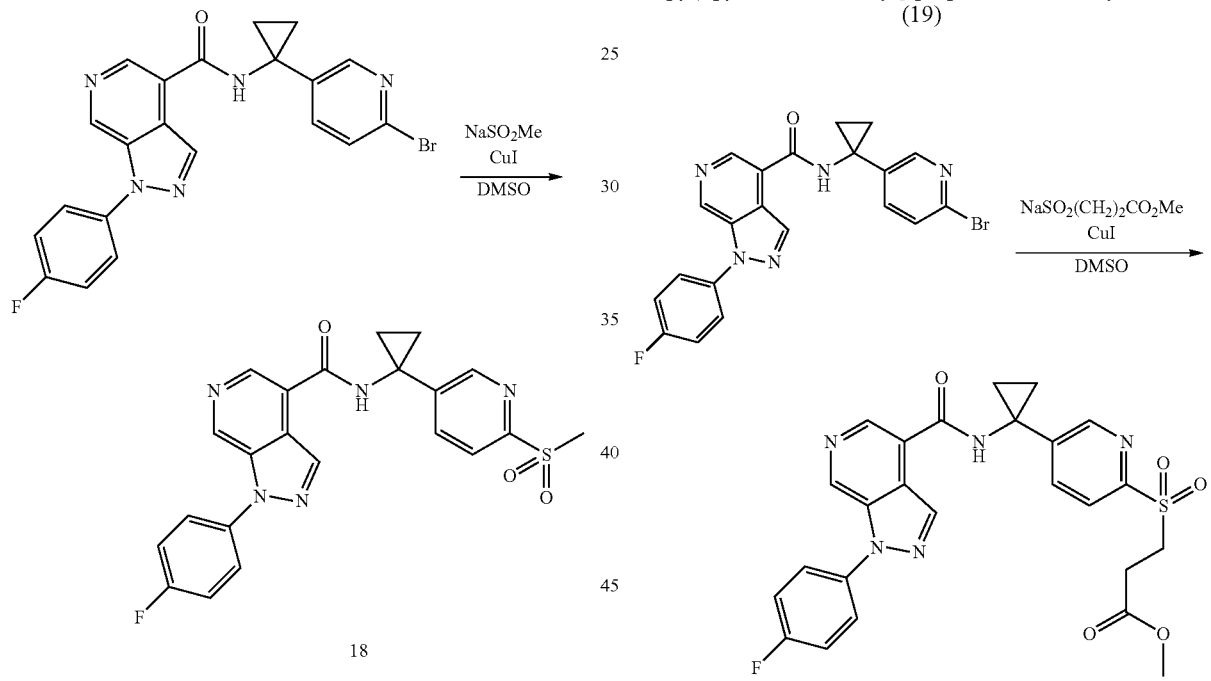

A solution of 1-(4-fluoro-phenyl)-1H-pyrazolo[3,4-c]pyridine-4-carboxylic acid [1-(6-bromo-pyridin-3-yl)-cyclopropyl]-amide (72.7 mg, 0.161 mmol), sodium methanesulfinate (32.8 mg, 0.321 mmol) and copper (I) iodine (61.2 mg, 0.321 mmol) in DMSO (1 mL) is evacuated and purged with argon three times and heated at 130° C. After 45 minutes, the reaction is cooled to room temperature and N,N'-dimethyl-ethylenediamine (69 µL, 0.64 mmol) is added. The mixture is stirred for 30 minutes, diluted with ethyl acetate (20 mL) and stirred for 15 minutes. A saturated aqueous solution of ammonium chloride (20 mL) is added; the resulting mixture is sonicated for 30 minutes, and diluted with ethyl acetate (100 mL). Phases are separated and the aqueous layer is extracted with ethyl acetate (3×20 mL). The combined organic layers are washed with saturated aqueous ammonium chloride (2×50 mL), saturated aqueous sodium bicarbonate (50 mL), brine (50 mL), dried over MgSO$_4$, filtered and concentrated. The resulting residue is purified by silica gel chromatography eluting with a gradient of 0-8% methanol in methylene chloride to afford the title compound as a solid.

The following compounds are prepared using the method described in Example 18:
1-(4-Fluoro-phenyl)-1H-pyrazolo[3,4-c]pyridine-4-carboxylic acid [1-(2-methanesulfonyl-pyridin-4-yl)-cyclopropyl]-amide;
1-(4-Fluoro-phenyl)-1H-pyrazolo[3,4-c]pyridine-4-carboxylic acid [1-(5-methanesulfonyl-pyrimidin-2-yl)-cyclopropyl]-amide;
1-(4-Fluoro-phenyl)-1H-pyrazolo[3,4-c]pyridine-4-carboxylic acid [1-(3-methanesulfonyl-phenyl)-cyclopropyl]-amide; and
1-(4-Fluoro-phenyl)-1H-pyrazolo[3,4-c]pyridine-4-carboxylic acid [1-(2-methanesulfonyl-pyridin-4-yl)-cyclobutyl]-amide.

Example 19

Synthesis of 3-[5-(1-{[1-(4-fluoro-phenyl)-1H-pyrazolo[3,4-c]pyridine-4-carbonyl]-amino}-cyclopropyl)-pyridine-2-sulfonyl]-propionic acid methyl ester (19)

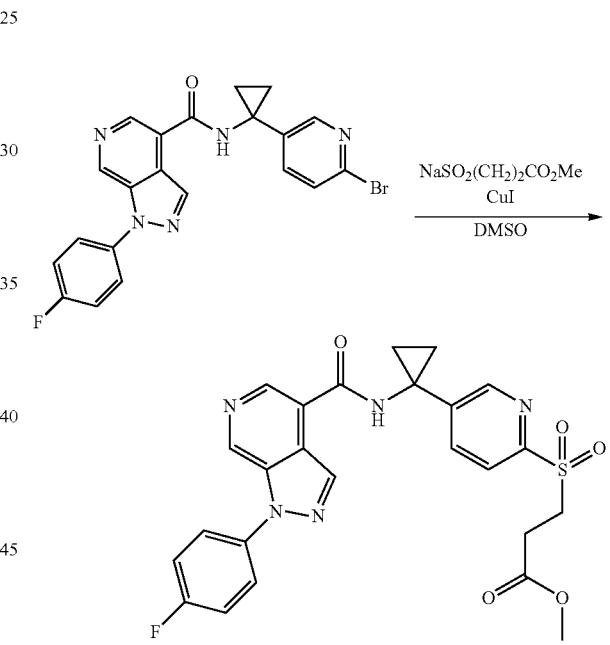

A solution of 1-(4-fluoro-phenyl)-1H-pyrazolo[3,4-c]pyridine-4-carboxylic acid [1-(6-bromo-pyridin-3-yl)-cyclopropyl]-amide (0.250 g, 0.553 mmol), sodium 3-methoxy-3-oxopropane-1-sulfinate (289 mg, 1.66 mmol) and copper (I) iodide (316 mg, 1.66 mmol) in DMSO (2 mL) is placed in a microwave tube and evacuated and purged with argon three times. The reaction mixture is heated in a microwave at 110° C. for 2 hours, diluted with ethyl acetate (200 mL), washed with saturated aqueous ammonium chloride (4×100 mL), saturated aqueous sodium bicarbonate (100 mL), brine (100 mL), dried over MgSO$_4$, filtered and concentrated. The resulting residue is purified by silica gel chromatography eluting with a gradient of 50-100% ethyl acetate in heptane to afford the title compound as a solid.

The following compound is prepared using the method described in Example 19:

3-[3-(1-{[1-(4-Fluoro-phenyl)-1H-pyrazolo[3,4-c]pyridine-4-carbonyl]-amino}-cyclopropyl)-benzenesulfonyl]-propionic acid methyl ester.

Example 20

Synthesis of 1-(4-fluoro-phenyl)-1H-pyrazolo[3,4-c]pyridine-4-carboxylic acid [1-(6-sulfamoyl-pyridin-3-yl)-cyclopropyl]-amide (20)

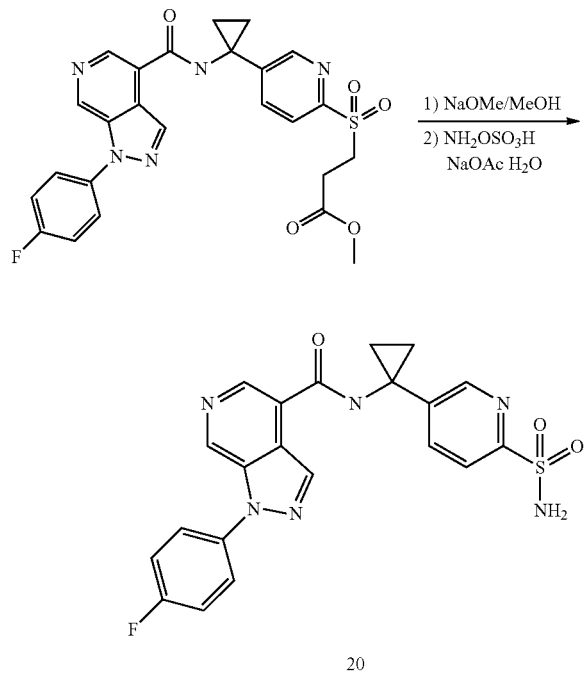

To a stirred solution of 3-[5-(1-{[1-(4-fluoro-phenyl)-1H-pyrazolo[3,4-c]pyridine-4-carbonyl]-amino}-cyclopropyl)-pyridine-2-sulfonyl]-propionic acid methyl ester (153 mg, 0.292 mmol) in DMSO (4 mL) is added a freshly prepared 15% solution of sodium methoxide (0.110 mL, 0.306 mmol) in methanol. After 15 minutes, the mixture is placed in a water bath, and a solution of N-hydroxylamine-O-sulfonic acid (661 mg, 5.84 mmol) and sodium acetate (384 mg, 4.68 mmol) in water (16 mL) is added. The water bath is removed and the reaction mixture is stirred at room temperature. After 60 hours, the mixture is diluted with ethyl acetate (20 mL) and water (20 mL). Phases are separated and the aqueous layer is extracted with ethyl acetate (3×20 mL). The pH of the combined organic layers are adjusted to 7 with 10% aqueous sodium bicarbonate. The organic layer is washed with water (3×20 mL), dried over MgSO₄, filtered and concentrated. The residue is purified by silica gel chromatography eluting with 100% ethyl acetate. The resultant solid is triturated with ether (3 times), filtered and dried under vacuum to afford the title compound as a solid.

The following compound is prepared using the method described in Example 20:

1-(4-Fluoro-phenyl)-1H-pyrazolo[3,4-c]pyridine-4-carboxylic acid [1-(3-sulfamoyl-phenyl)-cyclopropyl]-amide.

Example 21

Synthesis of 1-(4-fluoro-phenyl)-1H-pyrazolo[3,4-c]pyridine-4-carboxylic acid [1-(6-methylamino-pyridin-3-yl)-cyclopropyl]-amide (21)

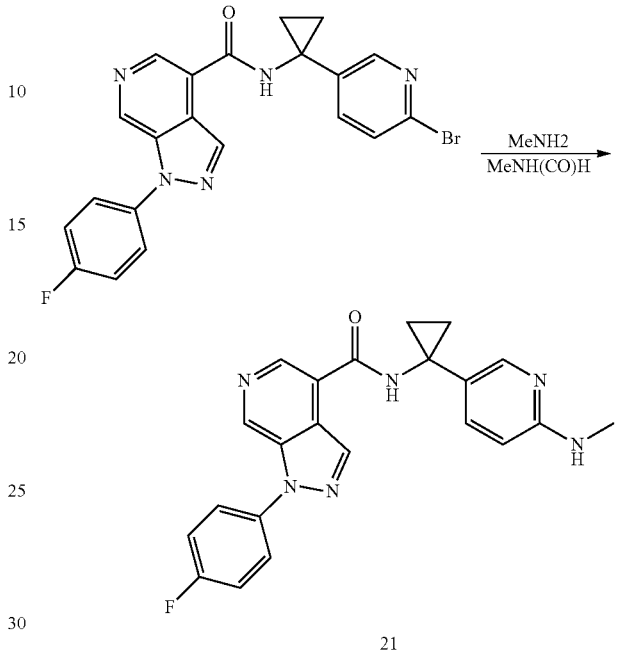

A pressure tube charged with 1-(4-fluoro-phenyl)-1H-pyrazolo[3,4-c]pyridine-4-carboxylic acid [1-(6-bromo-pyridin-3-yl)-cyclopropyl]-amide (0.200 g, 0.442 mmol), 33% methylamine in ethanol (0.250 mL, 1.99 mmol) in N-methylformamide (1 mL) is heated at 160° C. After 36 hours, the reaction is cooled to room temperature and diluted with ethyl acetate (20 mL) and water (20 mL). Phases are separated and the aqueous layer is extracted with ethyl acetate (3×20 mL). The combined organic layers are washed with saturated aqueous ammonium chloride (3×100 mL), saturated aqueous sodium bicarbonate (100 mL), brine (100 mL), dried over MgSO₄, filtered and concentrated. The residue is purified by silica gel chromatography eluting with 0-15% methanol in dichloromethane to afford the title compound as a solid.

Example 22

Synthesis of 1-(4-fluoro-phenyl)-1H-pyrazolo[3,4-c]pyridine-4-carboxylic acid [1-(6-morpholin-4-yl-pyridin-3-yl)-cyclopropyl]-amide (22)

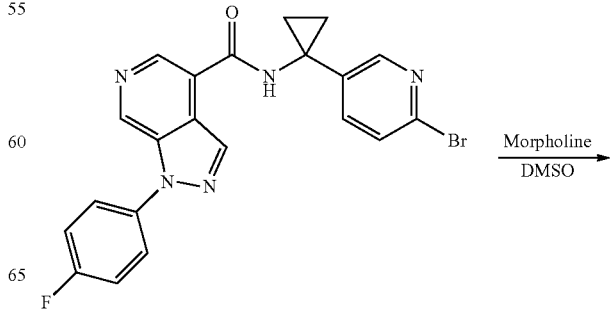

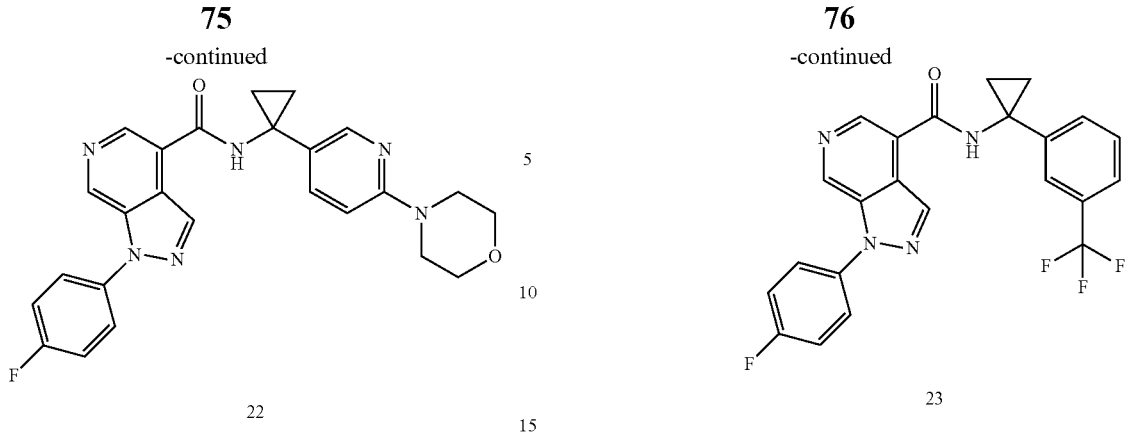

22

23

A solution of 1-(4-fluoro-phenyl)-1H-pyrazolo[3,4-c]pyridine-4-carboxylic acid [1-(6-bromo-pyridin-3-yl)-cyclopropyl]-amide (35 mg, 0.077 mmol) and morpholine (68 μL, 0.77 mmol) in DMSO (1 mL) is heated in a pressure tube at 160° C. After 40 hours, the mixture is cooled to room temperature, diluted with EtOAc (50 mL) and washed with saturated aqueous ammonium chloride (2×50 mL), saturated aqueous sodium bicarbonate (50 mL), brine (50 mL), dried over MgSO$_4$, filtered and concentrated. The resulting solid is purified by silica gel chromatography eluting with a gradient of 0-5% methanol in dichloromethane to give a solid, which is triturated with ether (5 mL), filtered and dried to afford the title compound.

Example 23

Synthesis of 1-(4-fluoro-phenyl)-1H-pyrazolo[3,4-c]pyridine-4-carboxylic acid [1-(3-trifluoromethyl-phenyl)-cyclopropyl]-amide (23)

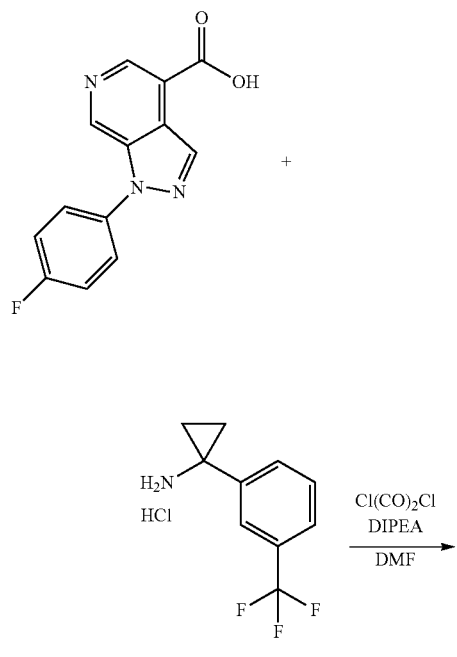

To a suspension of 1-(4-fluoro-phenyl)-1H-pyrazolo[3,4-c]pyridine-4-carboxylic acid (40.0 mg, 0.156 mmol) in methylene chloride (1 mL) is added oxalyl chloride (14 μL, 0.16 mmol) dropwise. After 10 minutes, a drop of N,N-dimethylformamide is added and the suspension is stirred at room temperature. After 60 minutes, an additional portion of oxalyl chloride (14 μL, 0.16 mmol) and a drop of N,N-dimethylformamide are added. After stirring for 30 minutes, the solvent is removed in vacuo; the residue is suspended in methylene chloride (1 mL) and concentrated in vacuo. The residue is dried under vacuum for 30 minutes, suspended in methylene chloride (1 mL) and added to a solution of 1-(3-trifluoromethyl-phenyl)-cyclopropylamine hydrochloride (74.1 mg, 0.312 mmol) and N,N-diisopropylethylamine (0.080 mL, 0.46 mmol) in methylene chloride (500 μL). After shaking at room temperature for 15 hours, the reaction is quenched with methanol (500 μL) and concentrated. The residue is purified by reverse phase HPLC using a Water BEH column (2.1×50 mm C18 1.7 μM) and a gradient of 10-95% acetonitrile in water containing 0.05% formic acid to afford the title compound.

The following compounds are prepared using the method described in Example 23:

1-(4-Fluoro-phenyl)-1H-pyrazolo[3,4-c]pyridine-4-carboxylic acid [1-(3-methoxy-phenyl)-cyclopropyl]-amide;
1-(4-Fluoro-phenyl)-1H-pyrazolo[3,4-c]pyridine-4-carboxylic acid [1-(6-dimethylamino-pyridin-2-yl)-cyclopropyl]-amide;
1-(4-Fluoro-phenyl)-1H-pyrazolo[3,4-c]pyridine-4-carboxylic acid (1-pyridin-3-yl-cyclopropyl)-amide;
1-(4-Fluoro-phenyl)-1H-pyrazolo[3,4-c]pyridine-4-carboxylic acid [1-(4-methoxy-phenyl)-cyclopropyl]-amide;
1-(4-Fluoro-phenyl)-1H-pyrazolo[3,4-c]pyridine-4-carboxylic acid [1-(4-fluoro-phenyl)-cyclopropyl]-amide;
1-(4-Fluoro-phenyl)-1H-pyrazolo[3,4-c]pyridine-4-carboxylic acid (1-m-tolyl-cyclopropyl)-amide;
1-(4-Fluoro-phenyl)-1H-pyrazolo[3,4-c]pyridine-4-carboxylic acid [1-(3-chloro-phenyl)-cyclopropyl]-amide;
4-(1-{[1-(4-Fluoro-phenyl)-1H-pyrazolo[3,4-c]pyridine-4-carbonyl]-amino}-cyclopropyl)-benzoic acid;
1-(4-Fluoro-phenyl)-1H-pyrazolo[3,4-c]pyridine-4-carboxylic acid [1-(3-fluoro-phenyl)-cyclopropyl]-amide;
1-(4-Fluoro-phenyl)-1H-pyrazolo[3,4-c]pyridine-4-carboxylic acid [1-(4-chloro-phenyl)-cyclopropyl]-amide;
1-(4-Fluoro-phenyl)-1H-pyrazolo[3,4-c]pyridine-4-carboxylic acid (1-p-tolyl-cyclopropyl)-amide;
1-(4-Fluoro-phenyl)-1H-pyrazolo[3,4-c]pyridine-4-carboxylic acid (1-phenyl-cyclopropyl)-amide;
1-(4-Fluoro-phenyl)-1H-pyrazolo[3,4-c]pyridine-4-carboxylic acid (1-o-tolyl-cyclopropyl)-amide;

1-(4-Fluoro-phenyl)-1H-pyrazolo[3,4-c]pyridine-4-carboxylic acid [1-(3-cyclopropyl-1,2,4-oxadiazol-5-yl)-cyclopropyl]-amide;
1-(4-Fluoro-phenyl)-1H-pyrazolo[3,4-c]pyridine-4-carboxylic acid [1-(5-cyclopropyl-1,2,4-oxadiazol-3-yl)-cyclopropyl]-amide;
1-(4-Fluoro-phenyl)-1H-pyrazolo[3,4-c]pyridine-4-carboxylic acid [1-(2-methyl-thiazol-4-yl)-cyclopropyl]-amide;
[2-(1-{[1-(4-Fluoro-phenyl)-1H-pyrazolo[3,4-c]pyridine-4-carbonyl]-amino}-cyclopropyl)-pyridin-4-ylmethyl]-carbamic acid tert-butyl ester;
1-(4-Fluoro-phenyl)-1H-pyrazolo[3,4-c]pyridine-4-carboxylic acid [1-(4-methoxy-pyridin-2-yl)-cyclopropyl]-amide;
1-(4-Fluoro-phenyl)-1H-pyrazolo[3,4-c]pyridine-4-carboxylic acid [1-(4-chloro-pyridin-2-yl)-cyclopropyl]-amide;
1-(4-Fluoro-phenyl)-1H-pyrazolo[3,4-c]pyridine-4-carboxylic acid [1-(5-bromo-pyridin-2-yl)-cyclopropyl]-amide;
1-(4-Fluoro-phenyl)-1H-pyrazolo[3,4-c]pyridine-4-carboxylic acid [1-(4-iodo-pyridin-2-yl)-cyclopropyl]-amide;
1-(4-Fluoro-phenyl)-1H-pyrazolo[3,4-e]pyridine-4-carboxylic acid [1-(4-bromo-phenyl)-cyclopropyl]-amide;
[6-(1-{[1-(4-Fluoro-phenyl)-1H-pyrazolo[3,4-c]pyridine-4-carbonyl]-amino}-cyclopropyl)-pyridin-3-ylmethyl]-carbamic acid tert-butyl ester;
1-(4-Fluoro-phenyl)-1H-pyrazolo[3,4-c]pyridine-4-carboxylic acid [1-(4-methoxy-phenyl)-cyclobutyl]-amide; and
1-(4-Fluoro-phenyl)-1H-pyrazolo[3,4-c]pyridine-4-carboxylic acid [1-(4-fluoro-phenyl)-cyclobutyl]-amide.

The following compounds are prepared using the coupling method described in Example 23, followed by Boc-deprotection according to the method described in Example 7:
1-(4-Fluoro-phenyl)-1H-pyrazolo[3,4-c]pyridine-4-carboxylic acid [1-(4-aminomethyl-pyridin-2-yl)-cyclopropyl]-amide; and
1-(4-Fluoro-phenyl)-1H-pyrazolo[3,4-c]pyridine-4-carboxylic acid [1-(5-aminomethyl-pyridin-2-yl)-cyclopropyl]-amide.

Example 24

Synthesis of 1-(4-fluoro-phenyl)-1H-pyrazolo[3,4-c]pyridine-4-carboxylic acid {1-[6-(acetyl-methyl-amino)-pyridin-3-yl]-cyclopropyl}-amide (24)

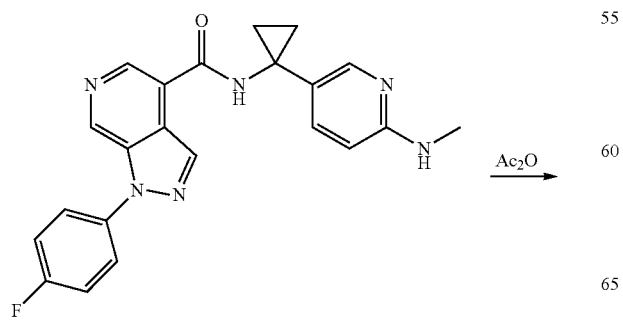

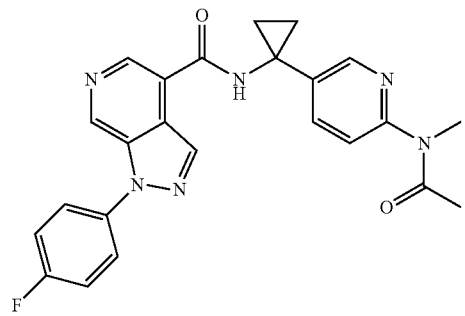

24

A solution of 1-(4-fluoro-phenyl)-1H-pyrazolo[3,4-c]pyridine-4-carboxylic acid [1-(6-methylamino-pyridin-3-yl)-cyclopropyl]-amide (40 mg, 0.099 mmol) in acetic anhydride (1 mL) is heated at 60° C. for 16 hours. The solution is cooled to room temperature, diluted with 3 mL of a 1N solution of aqueous NaOH, stirred for 20 minutes and extracted with ethyl acetate (5 mL). The organic layer is dried over magnesium sulfate, filtered and concentrated. The residue is purified by silica gel chromatography eluting with a gradient of 0-10% methanol in dichloromethane to afford the title compound.

Example 25

Synthesis of 6-bromo-1-(4-fluoro-phenyl)-1H-indazole-4-carboxylic acid [1-(2-methanesulfonyl-pyridin-4-yl)-cyclopropyl]-amide (25a), and 1-(4-fluoro-phenyl)-6-iodo-1H-indazole-4-carboxylic acid [1-(2-methanesulfonyl-pyridin-4-yl)-cyclopropyl]-amide (25b)

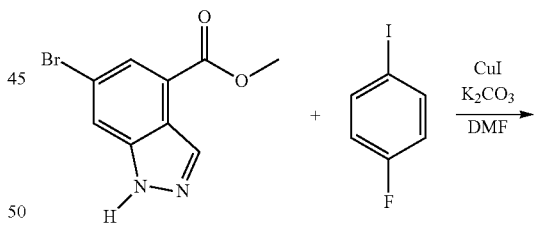

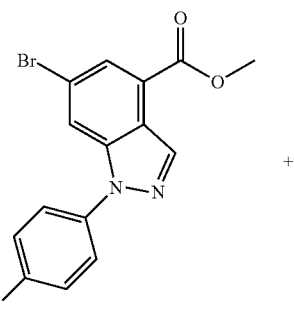

+

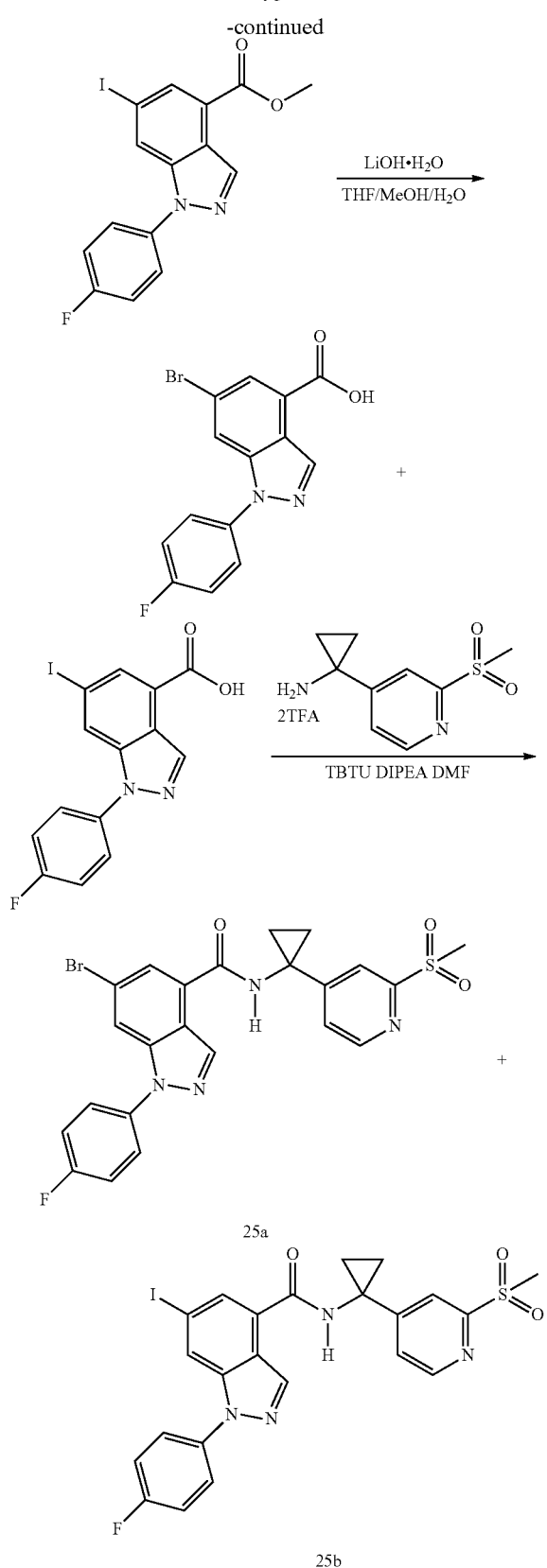

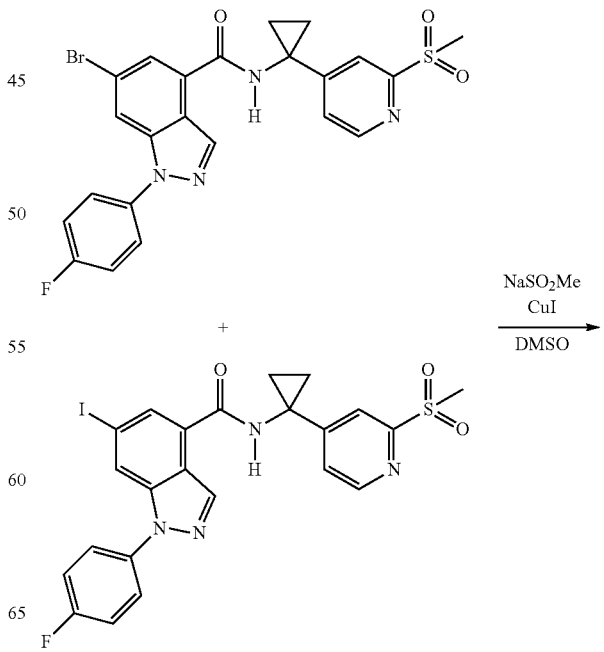

(10.0 g, 39.2 mmol) according to the copper-mediated cross coupling procedure described in Example 2.

To a solution of the mixture of 6-bromo-1-(4-fluoro-phenyl)-1H-indazole-4-carboxylic acid methyl ester and 1-(4-fluoro-phenyl)-6-iodo-1H-indazole-4-carboxylic acid methyl ester (500 mg) in THF (12 mL), methanol (4 mL), and water (4 mL) is added LiOH.H$_2$O (240 mg, 5.73 mmol). After stirring at room temperature for 4 hours, the reaction mixture is neutralized with 1M HCl, concentrated, and diluted with a 20% solution of methanol in dichloromethane (100 mL). Water (100 mL) is added and the pH of the mixture is adjusted to 4 with 1M HCl. Phases are separated and the aqueous layer is extracted with a 20% solution of methanol in dichloromethane (9×100 mL). The combined organic layers are dried over magnesium sulfate, filtered and concentrated to give a mixture of 6-bromo-1-(4-fluoro-phenyl)-1H-indazole-4-carboxylic acid and 1-(4-fluoro-phenyl)-6-iodo-1H-indazole-4-carboxylic acid as a solid.

The title compounds are prepared according to the coupling procedure described in Example 13 using a mixture of 6-bromo-1-(4-fluoro-phenyl)-1H-indazole-4-carboxylic acid and 1-(4-fluoro-phenyl)-6-iodo-1H-indazole-4-carboxylic acid (420 mg), and 1-(2-methanesulfonyl-pyridin-4-yl)-cyclopropylamine trifluoroacetic acid salt (851 mg, 1.93 mmol), and are purified by reverse phase HPLC using a C18 column and a gradient of acetonitrile in water containing 0.1% trifluoroacetic acid. The intermediate 1-(2-methanesulfonyl-pyridin-4-yl)-cyclopropylamine trifluoroacetic acid salt is prepared from [1-(2-bromo-pyridin-4-yl)-cyclopropyl]-carbamic acid tert-butyl ester according to a copper-mediated coupling procedure described in WO 2009/134666 (Example 7), followed by the Boc deprotection procedure described above (Example 3).

Example 26

Synthesis of 1-(4-fluoro-phenyl)-6-methanesulfonyl-1H-indazole-4-carboxylic acid [1-(2-methanesulfonyl-pyridin-4-yl)-cyclopropyl]-amide (26)

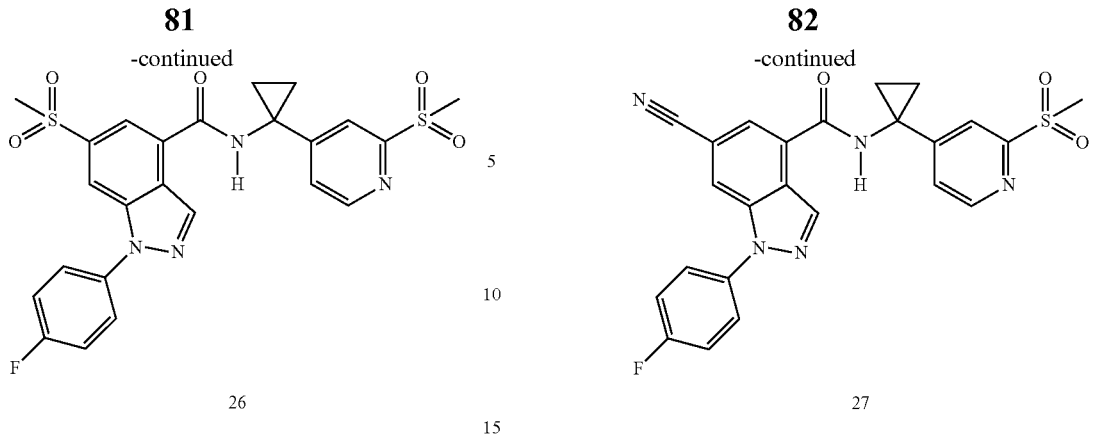

The title compound is synthesized according to the coupling procedure described in Example 18 from a mixture of 6-bromo-1-(4-fluoro-phenyl)-1H-indazole-4-carboxylic acid [1-(2-methanesulfonyl-pyridin-4-yl)-cyclopropyl]-amide, and 1-(4-fluoro-phenyl)-6-iodo-1H-indazole-4-carboxylic acid [1-(2-methanesulfonyl-pyridin-4-yl)-cyclopropyl]-amide (100 mg).

Example 27

Synthesis of 6-cyano-1-(4-fluoro-phenyl)-1H-indazole-4-carboxylic acid [1-(2-methanesulfonyl-pyridin-4-yl)-cyclopropyl]-amide (27)

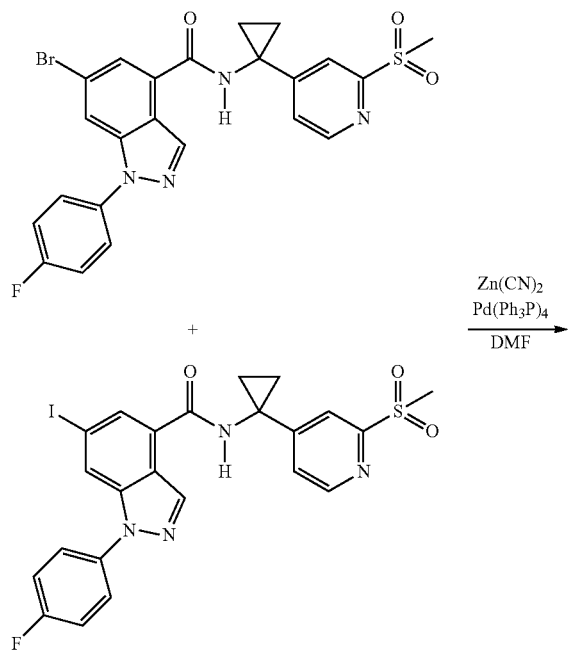

To a stirred solution of 6-bromo-1-(4-fluoro-phenyl)-1H-indazole-4-carboxylic acid [1-(2-methanesulfonyl-pyridin-4-yl)-cyclopropyl]-amide, and 1-(4-fluoro-phenyl)-6-iodo-1H-indazole-4-carboxylic acid [1-(2-methanesulfonyl-pyridin-4-yl)-cyclopropyl]-amide (150 mg) in DMF (1.0 mL, degassed and anhydrous) is added tetrakis(triphenylphosphine)palladium (33 mg, 0.028 mmol) and zinc cyanide (40 mg, 0.34 mmol). The solution is evacuated and purged with Argon (3 times) and warmed to 120° C. After 3 hours, the reaction is cooled to room temperature, diluted with saturated aqueous ammonium chloride (50 mL), and extracted with ethyl acetate (3×50 mL). The combined organic layers are washed with brine (50 mL), dried over magnesium sulfate, filtered and concentrated. The residue is purified on $SiO_2$ using a gradient of 50-100% ethyl acetate in heptane to give a solid, which is triturated with ethyl ether to afford the title product.

ASSESSMENT OF BIOLOGICAL PROPERTIES

Compounds are assessed for the ability to block the interaction of CCR1 and MIP-1α in a functional cellular assay measuring calcium flux in CCR1 transfected cells.

Non-adherent cells purchased from Chemicon Corporation (HTS005C), stably expressing recombinant CCR1 and G-alpha-16 are grown in RPMI 1640 medium (Mediatech 10-080-CM) supplemented with 10% FBS, 0.4 mg/mL Geneticin and penicillin/streptomycin. On the day of the assay, the cells are loaded with Calcium 4 dye (Molecular Devices R7448) with Probenecid (Invitrogen P346400) at 8E5 cells/mL for 1 hour at room temperature. After 1 hour, they are seeded in a 384-well tissue culture-treated plate at a density of 20,000 cells/well. Appropriately diluted test compound is added to the well to achieve a top concentration of 3,000 nM (diluted 4-fold with 10 doses total). The final concentration of DMSO is 1%. The buffer is HBSS (Invitrogen 14025) with 20 mM HEPES at pH 7.4. The cells incubate 30 minutes at 37 C and then 30 minutes at room temperature. The plates are transferred to the HAMAMATSU FDSS6000 where MIP-1alpha in 1% BSA is added at the EC80 final concentration. All plates must be read within 4 hours of the start of dye-loading. Wells +/− MIP-1alpha containing diluted DMSO instead of compound serve as the controls. Data are analyzed using Activity Base software.

In general, the preferred potency range ($IC_{50}$) of compounds in the above assay is between 0.1 nM to 3 μM, and the most preferred potency range is 0.1 nM to 50 nM.

Representative compounds of the invention have been tested in the above assay and have shown activity as CCR1 antagonists, this represents another embodiment of the invention.

TABLE II

| Name | CCR1 IC$_{50}$ (nM) |
|---|---|
| 1-(4-Fluoro-phenyl)-1H-pyrazolo[3,4-c]pyridine-4-carboxylic acid (1-1,3,4-thiadiazol-2-yl-cyclopropyl)-amide | 265 |
| 1-(4-Fluoro-phenyl)-1H-pyrazolo[3,4-c]pyridine-4-carboxylic acid [1-(6-bromo-pyridin-3-yl)-cyclopropyl]-amide | 19 |
| 1-(4-Fluoro-phenyl)-1H-pyrazolo[3,4-c]pyridine-4-carboxylic acid [1-(6-methanesulfonyl-pyridin-3-yl)-cyclopropyl]-amide | 7 |
| 1-(4-Fluoro-phenyl)-1H-pyrazolo[3,4-c]pyridine-4-carboxylic acid (1-pyridin-4-yl-cyclopropyl)-amide | 18 |
| 1-(4-Fluoro-phenyl)-1H-pyrazolo[3,4-c]pyridine-4-carboxylic acid [1-(2-bromo-pyridin-4-yl)-cyclopropyl]-amide | 0.5 |
| 1-(4-Fluoro-phenyl)-1H-pyrazolo[3,4-c]pyridine-4-carboxylic acid [1-(2-methanesulfonyl-pyridin-4-yl)-cyclopropyl]-amide | 2 |
| 1-(4-Fluoro-phenyl)-1H-pyrazolo[3,4-c]pyridine-4-carboxylic acid [1-(5-bromo-pyrimidin-2-yl)-cyclopropyl]-amide | 45 |
| 1-(4-Fluoro-phenyl)-1H-pyrazolo[3,4-c]pyridine-4-carboxylic acid [1-(5-methanesulfonyl-pyrimidin-2-yl)-cyclopropyl]-amide | 14 |
| 1-(4-Fluoro-phenyl)-1H-pyrazolo[3,4-c]pyridine-4-carboxylic acid [1-(5-methanesulfonyl-furan-2-yl)-cyclopropyl]-amide | 4 |
| 3-(1-{[1-(4-Fluoro-phenyl)-1H-pyrazolo[3,4-c]pyridine-4-carbonyl]-amino}-cyclopropyl)-benzoic acid methyl ester | 11 |
| 3-(1-{[1-(4-Fluoro-phenyl)-1H-pyrazolo[3,4-c]pyridine-4-carbonyl]-amino}-cyclopropyl)-benzoic acid | 27 |
| 1-(4-Fluoro-phenyl)-1H-pyrazolo[3,4-c]pyridine-4-carboxylic acid [1-(3-methylcarbamoyl-phenyl)-cyclopropyl]-amide | 2 |
| 1-[3-(1-{[1-(4-Fluoro-phenyl)-1H-pyrazolo[3,4-c]pyridine-4-carbonyl]-amino}-cyclopropyl)-benzoylamino]-cyclopropanecarboxylic acid methyl ester | 98 |
| 1-(4-Fluoro-phenyl)-1H-pyrazolo[3,4-c]pyridine-4-carboxylic acid {1-[3-(cyanomethyl-carbamoyl)-phenyl]-cyclopropyl}-amide | 35 |
| [3-(1-{[1-(4-Fluoro-phenyl)-1H-pyrazolo[3,4-c]pyridine-4-carbonyl]-amino}-cyclopropyl)-benzoylamino]-acetic acid methyl ester | 5 |
| (S)-2-[3-(1-{[1-(4-Fluoro-phenyl)-1H-pyrazolo[3,4-c]pyridine-4-carbonyl]-amino}-cyclopropyl)-benzoylamino]-propionic acid methyl ester | 80 |
| 1-(4-Fluoro-phenyl)-1H-pyrazolo[3,4-c]pyridine-4-carboxylic acid [1-(3-trifluoromethyl-phenyl)-cyclopropyl]-amide | 0.4 |
| 1-(4-Fluoro-phenyl)-1H-pyrazolo[3,4-c]pyridine-4-carboxylic acid [1-(3-methoxy-phenyl)-cyclopropyl]-amide | 5 |
| 1-(4-Fluoro-phenyl)-1H-pyrazolo[3,4-c]pyridine-4-carboxylic acid [1-(6-dimethylamino-pyridin-2-yl)-cyclopropyl]-amide | 3 |
| 1-(4-Fluoro-phenyl)-1H-pyrazolo[3,4-c]pyridine-4-carboxylic acid (1-pyridin-3-yl-cyclopropyl)-amide | 88 |
| 1-(4-Fluoro-phenyl)-1H-pyrazolo[3,4-c]pyridine-4-carboxylic acid [1-(4-methoxy-phenyl)-cyclopropyl]-amide | 17 |
| 1-(4-Fluoro-phenyl)-1H-pyrazolo[3,4-c]pyridine-4-carboxylic acid [1-(4-fluoro-phenyl)-cyclopropyl]-amide | 75 |
| 1-(4-Fluoro-phenyl)-1H-pyrazolo[3,4-c]pyridine-4-carboxylic acid (1-m-tolyl-cyclopropyl)-amide | 26 |
| 1-(4-Fluoro-phenyl)-1H-pyrazolo[3,4-c]pyridine-4-carboxylic acid [1-(3-chloro-phenyl)-cyclopropyl]-amide | 3 |
| 4-(1-{[1-(4-Fluoro-phenyl)-1H-pyrazolo[3,4-c]pyridine-4-carbonyl]-amino}-cyclopropyl)-benzoic acid | 69 |
| 1-(4-Fluoro-phenyl)-1H-pyrazolo[3,4-c]pyridine-4-carboxylic acid [1-(3-fluoro-phenyl)-cyclopropyl]-amide | 13 |
| 1-(4-Fluoro-phenyl)-1H-pyrazolo[3,4-c]pyridine-4-carboxylic acid [1-(4-chloro-phenyl)-cyclopropyl]-amide | 10 |
| 1-(4-Fluoro-phenyl)-1H-pyrazolo[3,4-c]pyridine-4-carboxylic acid (1-p-tolyl-cyclopropyl)-amide | 14 |
| 1-(4-Fluoro-phenyl)-1H-pyrazolo[3,4-c]pyridine-4-carboxylic acid (1-phenyl-cyclopropyl)-amide | 109 |
| 1-(4-Fluoro-phenyl)-1H-pyrazolo[3,4-c]pyridine-4-carboxylic acid (1-o-tolyl-cyclopropyl)-amide | 61 |
| 1-(4-Fluoro-phenyl)-1H-pyrazolo[3,4-c]pyridine-4-carboxylic acid [1-(3-cyclopropyl-1,2,4-oxadiazol-5-yl)-cyclopropyl]-amide | 11 |
| 1-(4-Fluoro-phenyl)-1H-pyrazolo[3,4-c]pyridine-4-carboxylic acid [1-(5-cyclopropyl-1,2,4-oxadiazol-3-yl)-cyclopropyl]-amide | 61 |
| 1-(4-Fluoro-phenyl)-1H-pyrazolo[3,4-c]pyridine-4-carboxylic acid [1-(2-methyl-thiazol-4-yl)-cyclopropyl]-amide | 99 |
| [2-(1-{[1-(4-Fluoro-phenyl)-1H-pyrazolo[3,4-c]pyridine-4-carbonyl]-amino}-cyclopropyl)-pyridin-4-ylmethyl]-carbamic acid tert-butyl ester | 285 |
| 1-(4-Fluoro-phenyl)-1H-pyrazolo[3,4-c]pyridine-4-carboxylic acid [1-(4-aminomethyl-pyridin-2-yl)-cyclopropyl]-amide | 290 |
| 1-(4-Fluoro-phenyl)-1H-pyrazolo[3,4-c]pyridine-4-carboxylic acid [1-(4-methoxy-pyridin-2-yl)-cyclopropyl]-amide | 31 |
| 1-(4-Fluoro-phenyl)-1H-pyrazolo[3,4-c]pyridine-4-carboxylic acid [1-(4-chloro-pyridin-2-yl)-cyclopropyl]-amide | 17 |
| 1-(4-Fluoro-phenyl)-1H-pyrazolo[3,4-c]pyridine-4-carboxylic acid [1-(5- | 9 |

TABLE II-continued

| Name | CCR1 IC$_{50}$ (nM) |
|---|---|
| bromo-pyridin-2-yl)-cyclopropyl]-amide | |
| 1-(4-Fluoro-phenyl)-1H-pyrazolo[3,4-c]pyridine-4-carboxylic acid [1-(4-iodo-pyridin-2-yl)-cyclopropyl]-amide | 2 |
| 1-(4-Fluoro-phenyl)-1H-pyrazolo[3,4-c]pyridine-4-carboxylic acid [1-(4-bromo-phenyl)-cyclopropyl]-amide | 4 |
| [6-(1-{[1-(4-Fluoro-phenyl)-1H-pyrazolo[3,4-c]pyridine-4-carbonyl]-amino}-cyclopropyl)-pyridin-3-ylmethyl]-carbamic acid tert-butyl ester | 81 |
| 1-(4-Fluoro-phenyl)-1H-pyrazolo[3,4-c]pyridine-4-carboxylic acid [1-(5-aminomethyl-pyridin-2-yl)-cyclopropyl]-amide | 705 |
| 1-(4-Fluoro-phenyl)-1H-pyrazolo[3,4-c]pyridine-4-carboxylic acid {1-[3-(carbamoylmethyl-carbamoyl)-phenyl]-cyclopropyl}-amide | 74 |
| 1-(4-Fluoro-phenyl)-1H-pyrazolo[3,4-c]pyridine-4-carboxylic acid {1-[3-(methylcarbamoylmethyl-carbamoyl)-phenyl]-cyclopropyl}-amide | 78 |
| 1-(4-Fluoro-phenyl)-1H-pyrazolo[3,4-c]pyridine-4-carboxylic acid [1-(3-bromo-phenyl)-cyclopropyl]-amide | 1 |
| 3-[3-(1-{[1-(4-Fluoro-phenyl)-1H-pyrazolo[3,4-c]pyridine-4-carbonyl]-amino}-cyclopropyl)-benzenesulfonyl]-propionic acid methyl ester | 17 |
| 1-(4-Fluoro-phenyl)-1H-pyrazolo[3,4-c]pyridine-4-carboxylic acid [1-(3-methanesulfonyl-phenyl)-cyclopropyl]-amide | 1 |
| 1-(4-Fluoro-phenyl)-1H-pyrazolo[3,4-c]pyridine-4-carboxylic acid [1-(3-carbamoyl-phenyl)-cyclopropyl]-amide | 40 |
| 3-[5-(1-{[1-(4-Fluoro-phenyl)-1H-pyrazolo[3,4-c]pyridine-4-carbonyl]-amino}-cyclopropyl)-pyridine-2-sulfonyl]-propionic acid methyl ester | 10 |
| 1-(4-Fluoro-phenyl)-1H-pyrazolo[3,4-c]pyridine-4-carboxylic acid [1-(6-methylamino-pyridin-3-yl)-cyclopropyl]-amide | 28 |
| 1-(4-Fluoro-phenyl)-1H-pyrazolo[3,4-c]pyridine-4-carboxylic acid [1-(6-sulfamoyl-pyridin-3-yl)-cyclopropyl]-amide | 5 |
| 1-(4-Fluoro-phenyl)-1H-pyrazolo[3,4-c]pyridine-4-carboxylic acid [1-(3-sulfamoyl-phenyl)-cyclopropyl]-amide | 3 |
| 1-(4-Fluoro-phenyl)-1H-pyrazolo[3,4-c]pyridine-4-carboxylic acid [1-(2-bromo-pyridin-4-yl)-cyclobutyl]-amide | 3 |
| 1-(4-Fluoro-phenyl)-1H-pyrazolo[3,4-c]pyridine-4-carboxylic acid [1-(2-methanesulfonyl-pyridin-4-yl)-cyclobutyl]-amide | 2 |
| 1-(4-Fluoro-phenyl)-1H-pyrazolo[3,4-c]pyridine-4-carboxylic acid [1-(4-methoxy-phenyl)-cyclobutyl]-amide | 51 |
| 1-(4-Fluoro-phenyl)-1H-pyrazolo[3,4-c]pyridine-4-carboxylic acid [1-(4-fluoro-phenyl)-cyclobutyl]-amide | 62 |
| 1-(4-Fluoro-phenyl)-1H-pyrazolo[3,4-c]pyridine-4-carboxylic acid [1-(6-morpholin-4-yl-pyridin-3-yl)-cyclopropyl]-amide | 6 |
| 1-(4-Fluoro-phenyl)-1H-indazole-4-carboxylic acid [1-(2-methanesulfonyl-pyridin-4-yl)-cyclopropyl]-amide | 4 |
| 1-(4-Fluoro-phenyl)-1H-pyrazolo[3,4-c]pyridine-4-carboxylic acid {1-[6-(acetyl-methyl-amino)-pyridin-3-yl]-cyclopropyl}-amide | 20 |
| 6-Bromo-1-(4-fluoro-phenyl)-1H-indazole-4-carboxylic acid [1-(2-methanesulfonyl-pyridin-4-yl)-cyclopropyl]-amide | 2 |
| 1-(4-Fluoro-phenyl)-6-iodo-1H-indazole-4-carboxylic acid [1-(2-methanesulfonyl-pyridin-4-yl)-cyclopropyl]-amide | 13 |
| 1-(4-Fluoro-phenyl)-6-methanesulfonyl-1H-indazole-4-carboxylic acid [1-(2-methanesulfonyl-pyridin-4-yl)-cyclopropyl]-amide | 7 |
| 6-Cyano-1-(4-fluoro-phenyl)-1H-indazole-4-carboxylic acid [1-(2-methanesulfonyl-pyridin-4-yl)-cyclopropyl]-amide | 0.1 |

METHOD OF USE

The compounds of the invention are effective antagonists of the interactions between CCR1 and its chemokine ligands and thus inhibit CCR1-mediated activity. Therefore, in one embodiment of the invention, there is provided methods of treating autoimmune disorders using compounds of the invention. In another embodiment, there is provided methods of treating inflammatory disorders using compounds of the invention.

Without wishing to be bound by theory, by antagonizing the interactions between CCR1 and its chemokine ligands, the compounds block chemotaxis of pro-inflammatory cells including monocytes, macrophages dendritic cells, eosinophils, and T cells (TH1) cells and other CCR1 positive cells to inflamed tissues and thereby ameliorate the chronic inflammation associated with autoimmune diseases. Thus, the inhibition of CCR1 activity is an attractive means for preventing and treating a variety of autoimmune disorders, including inflammatory diseases, autoimmune diseases, organ (Horuk et al. (2001) JBC 276 p. 4199) and bone marrow transplant rejection and other disorders associated with an influx of pro-inflammatory cells. For example, the compounds of the invention may be used to prevent or treat acute or chronic inflammation, allergies, contact dermatitis, psoriasis, rheumatoid arthritis, multiple sclerosis, type 1 diabetes, inflammatory bowel disease, Guillain-Barre syndrome, Crohn's disease, ulcerative colitis, graft versus host disease (and other forms of organ or bone marrow transplant rejection), Alzheimer's disease (Halks-Miller et al. (2003) *Ann Neurol* 54 p. 638), Asthma (Jouber et al. (2008) *J. Immun* 180 p. 1268), chronic kidney disease (Topham et al. (1999) *J. Clin. Invest.* 104 p. 1549), sepsis (He et al. (2007) *Am J. Physio* 292 p. G1173), autoimmune myocarditis (Futamats et al. (2006) *J Mol Cell Cardiology* 40 p. 853), multiple myeloma (*Blood* (2001) 97 pp 3349-3353), COPD (*Expert Opin. Investig. Drugs* (2005) 14 pp 785-796) and systemic lupus erythematosus. In particular, the compounds may be used to prevent or treat rheumatoid arthritis and multiple sclerosis. Other disorders associated with the trafficking of pro-inflammatory cells will be evident to those of ordinary skill in the art and can also be treated with the compounds and compositions of this invention.

For treatment of the above-described diseases and conditions, a therapeutically effective dose will generally be in the range from about 0.01 mg/kg to about 100 mg/kg of body weight per dosage of a compound of the invention; preferably, from about 0.1 mg/kg to about 20 mg/kg of body weight per dosage. For example, for administration to a 70 kg person, the dosage range would be from about 0.7 mg to about 7000 mg per dosage of a compound of the invention, preferably from about 7.0 mg to about 1400 mg per dosage. Some degree of routine dose optimization may be required to determine an optimal dosing level and pattern. The active ingredient may be administered from 1 to 6 times a day.

General Administration and Pharmaceutical Compositions

When used as pharmaceuticals, the compounds of the invention are typically administered in the form of a pharmaceutical composition. Such compositions can be prepared using procedures well known in the pharmaceutical art and comprise at least one compound of the invention. The compounds of the invention may also be administered alone or in combination with adjuvants that enhance stability of the compounds of the invention, facilitate administration of pharmaceutical compositions containing them in certain embodiments, provide increased dissolution or dispersion, increased antagonist activity, provide adjunct therapy, and the like. The compounds according to the invention may be used on their own or in conjunction with other active substances according to the invention, optionally also in conjunction with other pharmacologically active substances. In general, the compounds of this invention are administered in a therapeutically or pharmaceutically effective amount, but may be administered in lower amounts for diagnostic or other purposes.

Administration of the compounds of the invention, in pure form or in an appropriate pharmaceutical composition, can be carried out using any of the accepted modes of administration of pharmaceutical compositions. Thus, administration can be, for example, orally, buccally (e.g., sublingually), nasally, parenterally, topically, transdermally, vaginally, or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, preferably in unit dosage forms suitable for simple administration of precise dosages. The pharmaceutical compositions will generally include a conventional pharmaceutical carrier or excipient and a compound of the invention as the/an active agent, and, in addition, may include other medicinal agents, pharmaceutical agents, carriers, adjuvants, diluents, vehicles, or combinations thereof. Such pharmaceutically acceptable excipients, carriers, or additives as well as methods of making pharmaceutical compositions for various modes or administration are well-known to those of skill in the art. The state of the art is evidenced, e.g., by *Remington: The Science and Practice of Pharmacy,* 20th Edition, A. Gennaro (ed.), Lippincott Williams & Wilkins, 2000; *Handbook of Pharmaceutical Additives,* Michael & Irene Ash (eds.), Gower, 1995; *Handbook of Pharmaceutical Excipients,* A. H. Kibbe (ed.), American Pharmaceutical Ass'n, 2000; H. C. Ansel and N. G. Popovish, *Pharmaceutical Dosage Forms and Drug Delivery Systems,* 5th ed., Lea and Febiger, 1990; each of which is incorporated herein by reference in their entireties to better describe the state of the art.

As one of skill in the art would expect, the forms of the compounds of the invention utilized in a particular pharmaceutical formulation will be selected (e.g., salts) that possess suitable physical characteristics (e.g., water solubility) that is required for the formulation to be efficacious.

The invention claimed is:

1. A compound of the formula (I)

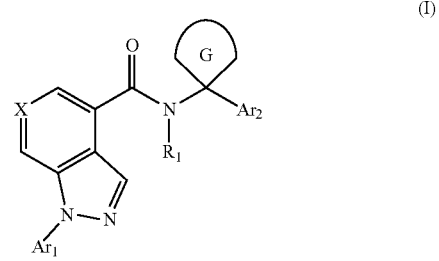

wherein
X is nitrogen or, C—$R_2$;
$Ar_1$ is carbocycle, heteroaryl or heterocyclyl each optionally substituted by one to three $R_a$;
$Ar_2$ is carbocycle, heteroaryl or heterocyclyl, each optionally substituted by one to three $R_b$;
Cyclic G is cyclopropyl or cyclobutyl each optionally substituted by one to two $R_g$;
$R_1$ is hydrogen, $C_{1-6}$ alkyl or $C_{1-6}$ alkoxy$C_{1-6}$ alkyl;
$R_2$ is hydrogen or $R_a$;
$R_a$ is $C_{1-6}$ alkyl, $C_{3-10}$ cycloalkyl, $C_{1-6}$ alkoxy, $C_{1-6}$ alkylthio, $C_{1-6}$ alkylsulfonyl, $C_{1-6}$ alkoxycarbonyl, amino, mono- or di-$C_{1-6}$ alkylamino, $C_{3-6}$ cycloalkylamino, $C_{1-6}$ alkylaminocarbonyl, $C_{1-6}$ acyl, $C_{1-6}$ acylamino, $C_{1-6}$ dialkylaminocarbonyl, hydroxyl, halogen, cyano, nitro, oxo, $R_3$—S(O)$_m$—NH—, $R_3$—NH—S(O)$_m$—, aryl or carboxyl;
$R_b$ is hydroxyl, carboxyl, halogen, —(CH$_2$)$_n$—CN, —(CH$_2$)$_n$—CO$_2$C$_{1-6}$alkyl, nitro, —SO$_3$H, $C_{1-6}$ alkyl, $C_{2-6}$ alkenyl, $C_{2-6}$ alkynyl, $C_{3-10}$ cycloalkyl, $C_{1-6}$ alkoxy, $C_{1-6}$alkylC(O)—, —(CH$_2$)$_n$—NR$_c$R$_d$, $R_3$—S(O)$_m$ (CH$_2$)$_{0-1}$—, $R_3$—S(O)$_m$—NR$_e$—, $R_3$—NR$_e$—S(O)$_m$ (CH$_2$)$_{0-1}$—, —NR$_f$—C(O)—R$_e$, —(CH$_2$)$_y$—C(O)—(CH$_2$)$_n$—NR$_c$R$_d$, heterocyclyl, aryl or heteroaryl, each $R_b$ where possible is optionally halogenated or substituted with 1 to 3 $C_{1-6}$ alkyl, hydroxyl, $C_{1-6}$ acyl, $C_{1-6}$ alkoxycarbonyl, $C_{1-6}$ alkyl-S(O)$_m$—, aryl or carboxyl;
each $R_c$, $R_d$ are independently hydrogen, $C_{1-6}$ alkyl, $C_{1-6}$ acyl, $C_{3-10}$ cycloalkyl, $C_{1-6}$ alkoxy, hydroxy$C_{1-6}$ alkyl, cyano-$C_{1-6}$ alkyl, $C_{1-6}$ alkyl$C_{1-6}$ alkoxy, $C_{1-6}$ alkylsulfonyl, $C_{1-6}$ alkoxycarbonyl$C_{0-3}$alkyl, $C_{1-6}$ alkoxycarbonyl$C_{3-10}$cycloalkyl, —(CH$_2$)$_n$—C(O)—NR$_e$R$_f$, or —(CH$_2$)$_n$—NR$_e$R$_f$;
each $R_e$, $R_f$ are independently hydrogen, $C_{1-6}$ alkyl, $C_{3-10}$ cycloalkyl, $C_{1-6}$ alkoxy, $C_{1-6}$ alkoxy$C_{1-6}$alkyl, mono- or diC$_{1-6}$alkylamino$C_{1-6}$alkyl, hydroxy$C_{1-6}$ alkyl or $C_{1-6}$ acyl;
$R_g$ is $C_{1-6}$ alkyl, wherein the $C_{1-6}$ alkyl is optionally partially or fully halogenated, $C_{2-6}$ alkenyl, carbocycle, $C_{1-6}$ alkoxy, carbocyclyl-$C_{1-6}$ alkoxy, carbocyclyl-$C_{1-6}$ alkyl, hydroxy$C_{1-6}$ alkyl, hydroxyl, —(CH$_2$)$_n$—CO$_2$C$_{1-6}$ alkyl or oxo;
$R_3$ is hydrogen, $C_{1-6}$ alkyl, $C_{3-6}$cycloalkyl, heterocyclyl (CH$_2$)$_{0-1}$, mono- or di-$C_{1-6}$ alkylamino, mono- or di-$_{1-6}$ alkylamino(CH$_2$)$_{2-3}$N(R$_e$)—, aryl or heteroaryl each optionally substituted with 1 to 3 $C_{1-6}$ alkyl, $C_{3-6}$cycloalkyl, $C_{1-6}$alkoxy, halogen, hydroxyl, oxo, carboxyl, —C(O)$NR_eR_f$, amino, mono-or di-$C_{1-6}$ alkylamino, $C_{1-6}$ alkoxycarbonyl or $C_{1-6}$ acylamino;
each n, y are independently 0-3;
each m is independently 0-2;
or a pharmaceutically acceptable salt thereof.

2. The compound according to claim 1, and wherein
X is nitrogen;
$Ar_1$ is carbocycle optionally substituted by one to three $R_a$;
$Ar_2$ is carbocycle or heteroaryl, each optionally substituted by one to three $R_b$;
$R_1$ is hydrogen;
$R_a$ is $C_{1-3}$alkyl, $C_{1-3}$ alkoxy, di-$C_{1-6}$ alkylamino, methylsulfonyl, halogen, or cyano;
$R_b$ is hydroxyl, carboxyl, halogen, —$(CH_2)_n$—CN, —$(CH_2)_n$—$CO_2C_{1-6}$alkyl, nitro, —$SO_3H$, $C_{1-6}$ alkyl, $C_{2-6}$ alkenyl, $C_{2-6}$ alkynyl, $C_{3-10}$cycloalkyl, $C_{1-6}$alkoxy, $C_{1-6}$alkylC(O)—, —$(CH_2)_n$—$NR_cR_d$, $R_3$—S(O)$_m$ $(CH_2)_{0-1}$—, $R_3$—S(O)$_m$—$NR_e$—, $R_3$—$NR_e$—S(O)$_m$ $(CH_2)_{0-1}$—, —$NR_f$—C(O)—$R_e$, —$(CH_2)_y$—C(O)— $(CH_2)_n$—$NR_cR_d$, heterocyclyl, aryl or heteroaryl, each $R_b$ where possible is optionally halogenated or substituted with 1 to 3 $C_{1-6}$ alkyl, $C_{1-6}$ acyl, $C_{1-6}$ alkoxycarbonyl, $C_{1-6}$ alkyl-S(O)$_m$—, aryl or carboxyl;
$R_3$ is hydrogen, $C_{1-6}$ alkyl, $C_{3-6}$cycloalkyl, heterocyclyl $(CH_2)_{0-1}$, mono- or di-$C_{1-6}$ alkylamino, mono-or di-$_{1-6}$ alkylamino$(CH_2)_{2-3}N(C_{1-6}$alkyl)-, aryl or heteroaryl each optionally substituted with 1 to 2 $C_{1-6}$ alkyl, $C_{3-6}$cycloalkyl, $C_{1-6}$alkoxy, halogen, hydroxyl, oxo, carboxyl, —C(O)$NR_eR_f$, amino, mono- or di-$C_{1-6}$ alkylamino, $C_{1-6}$ alkoxycarbonyl or $C_{1-6}$ acylamino
or a pharmaceutically acceptable salt thereof.

3. The compound according to claim 2, and wherein
$Ar_1$ is phenyl is substituted by one to two $R_a$;
$Ar_2$ is phenyl, thiadiazolyl, oxadiazolyl, pyrimidinyl, furanyl, thiazolyl or pyridyl, each optionally substituted by one to two $R_b$;
$R_a$ is halogen;
$R_b$ is hydroxyl, carboxyl, halogen, —$CF_3$, —CN, —$SO_3H$, $C_{1-3}$ alkyl, $C_{3-6}$ cycloalkyl $C_{1-3}$ alkoxy, —$(CH_2)_n$— $CO_2C_{1-3}$alkyl, —$(CH_2)_n$—$NR_cR_d$, $R_3$—S(O)$_m$ $(CH_2)_{0-1}$—, $R_3$—S(O)$_2$—$NR_e$—, $R_3$—$NR_e$—S(O)$_2$ $(CH_2)_{0-1}$—, —$NR_f$—C(o)—$R_e$, —$(CH_2)_y$—C(o)— $NR_cR_d$, or morpholinyl;
each $R_c$, $R_d$ are independently hydrogen, $C_{1-3}$ alkyl, $C_{1-3}$ acyl, cyano-$C_{1-3}$ alkyl, $C_{1-3}$ alkoxycarbonyl$C_{0-3}$alkyl, $C_{1-3}$ alkoxycarbonyl$C_{3-6}$cycloalkyl, or —$(CH_2)_n$—C (O)—$NR_eR_f$;
each $R_e$, $R_f$ are independently hydrogen or $C_{1-3}$ alkyl;
$R_3$ is hydrogen or $C_{1-6}$alkyl, each optionally substituted with one to two $C_{1-6}$alkoxy, or oxo
or a pharmaceutically acceptable salt thereof.

4. The compound according to claim 3, and wherein
Cyclic G is cyclopropyl;
$R_a$ is —F or —Cl;
$R_b$ is —$CH_3$, carboxyl, —F, —Cl, —Br, —I, —$CF_3$, cyclopropyl, —$OCH_3$, —$CO_2Me$, —$NR_cR_d$, —$CH_2$—$NR_c$ $R_d$, $R_3$—S(O)$_m$—, $R_3$—S(O)$_2$—$NR_e$—, $R_3$—$NR_e$—S (O)$_2$—, —$NR_f$—C(O)—$R_e$, —C(O)$NR_cR_d$ or morpholinyl;
each $R_c$, $R_d$ are independently hydrogen, —$CH_3$, —C(O) $CH_3$, —$CH_2CN$, $C_{1-4}$ alkoxycarbonyl, methoxycarbonyl-$C_{1-2}$alkyl-, methoxycarbonyl-$C_3$cycloalkyl-or —$(CH_2)$—C(O)—$NR_eR_f$;
each $R_e$, $R_f$ are independently hydrogen or —$CH_3$;
$R_3$ is hydrogen or $C_{1-4}$alkyl each optionally substituted with one to two —$OCH_3$ or oxo
or a pharmaceutically acceptable salt thereof.

5. The compound according to claim 4, and wherein
X is C—$R_2$;
$Ar_1$ is carbocycle optionally substituted by one to three $R_a$;
$Ar_2$ is carbocycle or heteroaryl, each optionally substituted by one to three $R_b$;
$R_1$ is hydrogen;
$R_2$ is hydrogen or $R_a$;
$R_a$ is $C_{1-3}$alkyl, $C_{1-3}$ alkoxy, di-$C_{1-6}$ alkylamino, methylsulfonyl, halogen, or cyano;
$R_b$ is hydroxyl, carboxyl, halogen, —$(CH_2)_n$—CN, —$(CH_2)_n$—$CO_2C_{1-6}$alkyl, nitro, —$SO_3H$, $C_{1-6}$ alkyl, $C_{2-6}$ alkenyl, $C_{2-6}$ alkynyl, $C_{3-10}$cyclo alkyl, $C_{1-6}$alkoxy, $C_{1-6}$alkylC(O)—, —$(CH_2)_n$—$NR_cR_d$, $R_3$—S(O)$_m$ $(CH_2)_{0-1}$—, $R_3$—S(O)$_m$$NR_e$—, $R_3$—$NR_e$—S(O)$_m$ $(CH_2)_{0-1}$—, —$NR_f$—C(O)—$R_e$, —$(CH_2)_y$—C(O)— $(CH_2)_n$—$NR_cR_d$, heterocyclyl, aryl or heteroaryl, each $R_b$ where possible is optionally halogenated or substituted with 1 to 3 $C_{1-6}$ alkyl, $C_{1-6}$ acyl, $C_{1-6}$ alkoxycarbonyl, $C_{1-6}$ alkyl-S(O)$_m$—, aryl or carboxyl;
each $R_c$, $R_d$ are independently hydrogen, $C_{1-6}$ alkyl, $C_{1-6}$ acyl, $C_{3-10}$ cycloalkyl, $C_{1-6}$ alkoxy, hydroxy$C_{1-6}$ alkyl, cyano$C_{1-6}$ alkyl, $C_{1-6}$ alkyl$C_{1-6}$ alkoxy, $C_{1-6}$ alkylsulfonyl, $C_{1-6}$alkoxycarbonyl$C_{0-3}$alkyl, $C_{1-6}$ alkoxycarbonyl$C_{3-10}$cycloalkyl, —$(CH_2)_n$—C(O)—$NR_eR_f$ or —$(CH_2)_n$—$NR_eR_f$;
each $R_e$, $R_f$ are independently hydrogen, $C_{1-6}$ alkyl, $C_{3-10}$ cycloalkyl, $C_{1-6}$ alkoxy, $C_{1-6}$ alkoxy$C_{1-6}$alkyl, mono- or di$C_{1-6}$alkylamino$C_{1-6}$alkyl, hydroxy$C_{1-6}$ alkyl or $C_{1-6}$ acyl;
$R_3$ is hydrogen, $C_{1-6}$ alkyl, $C_{3-6}$cycloalkyl, heterocyclyl $(CH_2)_{0-1}$, mono- or di-$C_{1-6}$ alkylamino, mono- or di-$_{1-6}$ alkylamino$(CH_2)_{2-3}N(C_{1-6}$alkyl)-, aryl or heteroaryl each optionally substituted with 1 to 2 $C_{1-6}$ alkyl, $C_{3-6}$cycloalkyl, $C_{1-6}$alkoxy, halogen, hydroxyl, oxo, carboxyl, —C(O)$NR_eR_f$, amino, mono- or di-$C_{1-6}$ alkylamino, $C_{1-6}$ alkoxycarbonyl or $C_{1-6}$ acylamino
or a pharmaceutically acceptable salt thereof.

6. The compound according to claim 5, and wherein
$Ar_1$ is phenyl is substituted by one to two $R_a$;
$Ar_2$ is phenyl, thiadiazolyl, oxadiazolyl, pyrimidinyl, furanyl, thiazolyl or pyridyl, each optionally substituted by one to two $R_b$;
$R_a$ is $C_{1-3}$alkyl, methylsulfonyl, halogen, or cyano;
$R_b$ is hydroxyl, carboxyl, halogen, —$CF_3$, —CN, —$SO_3H$, $C_{1-3}$ alkyl, $C_{3-6}$ cycloalkyl $C_{1-3}$ alkoxy, —$(CH_2)_n$— $CO_2C_{1-3}$alkyl, $(CH_2)_n$—$NR_cR_d$, $R_3$—S(O)$_m$ $(CH_2)_{0-1}$—, $R_3$—S(O)$_2$—$NR_e$—, $R_3$—$NR_e$—S(O)$_2$ $(CH_2)_{0-1}$—, —$NR_f$—C(O)—$R_e$, —$(CH_2)_y$—C(O)— $NR_cR_d$, or morpholinyl;
each $R_c$, $R_d$ are independently hydrogen, $C_{1-3}$ alkyl, $C_{1-3}$ acyl, cyano-$C_{1-3}$ alkyl, $C_{1-3}$ alkoxycarbonyl$C_{0-3}$alkyl, $C_{1-3}$ alkoxycarbonyl$C_{3-6}$cycloalkyl, or —$(CH_2)_n$—C (O)—$NR_eR_f$;
each $R_e$, $R_f$ are independently hydrogen or $C_{1-3}$ alkyl;
$R_3$ is hydrogen or $C_{1-6}$alkyl, each optionally substituted with one to two $C_{1-6}$alkoxy, or oxo
or a pharmaceutically acceptable salt thereof.

7. The compound according to claim 6, and wherein
$R_a$ is —F or —Cl, methyl, methylsulfonyl or cyano;
$R_b$ is —$CH_3$, carboxyl, —F, —Cl, —Br, —I, —$CF_3$, cyclopropyl, —$OCH_3$, —$CO_2Me$, —$NR_cR_d$, —$(CH_2)$—$NR_c$ $R_d$, $R_3$—S(O)$_m$—, $R_3$—S(O)$_2$—$NR_e$—, $R_3$—$NR_e$—S (O)$_2$—, —$NR_f$—C(O)—$R_e$, —C(O)$NR_cR_d$ or morpholinyl;

each $R_c$, $R_d$ are independently hydrogen, —$CH_3$, —C(O)$CH_3$, —$CH_2CN$, $C_{1-4}$ alkoxycarbonyl, methoxycarbonyl-$C_{1-2}$alkyl-, methoxycarbonyl-$C_3$cycloalkyl- or —($CH_2$)—C(O)—$NR_eR_f$;

each $R_e$, $R_f$ are independently hydrogen or —$CH_3$;

$R_3$ is hydrogen or $C_{1-4}$alkyl each optionally substituted with one to two —$OCH_3$ or oxo or a pharmaceutically acceptable salt thereof.

8. The compound according to claim 7, and wherein $R_c$, is hydrogen or $C_{1-6}$ alkyl, and $R_d$ is $C_{1-6}$ acyl, cyano-$C_{1-6}$alkyl-, $C_{1-6}$alkoxycarbonyl-$C_{0-3}$alkyl-, $C_{1-6}$ alkoxycarbonyl$C_{3-10}$cycloalkyl, or —($CH_2$)$_n$—C(O)—$NR_eR_f$;

each $R_e$, $R_f$ are independently hydrogen, $C_{1-6}$ alkyl or a pharmaceutically acceptable salt thereof.

9. The compound according to claim 8, and wherein $Ar_2$ is phenyl, pyrimidinyl, furanyl, thiazolyl or pyridyl, each optionally substituted by one or two $R_b$;

$R_b$ is —$SO_2Me$, —I, —Br, —Cl, —$CF_3$, —OMe, —NMe, —CONHMe, —$SO_2NH_2$ or a pharmaceutically acceptable salt thereof.

10. The compound according to claim 9, and wherein $Ar_2$ is

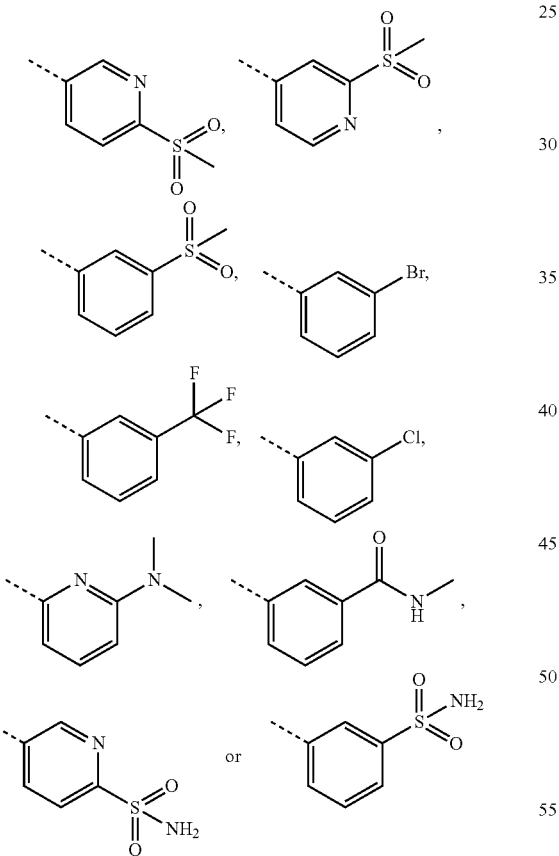

or a pharmaceutically acceptable salt thereof.

11. The compound according to claim 10, and wherein $R_g$ is i) $C_{1-2}$ alkyl, —$CF_3$, $C_2$ alkenyl, phenyl, $C_{1-4}$ alkoxy, carbocyclyl$CH_2$O—, carbocyclyl$CH_2$— —$CH_2OH$, hydroxyl, —$CO_2C_{1-4}$ alkyl or oxo;

or ii) is methyl, vinyl, —$CF_3$, phenyl, —$CH_2OH$, or hydroxyl or a pharmaceutically acceptable salt thereof.

12. A compound chosen from

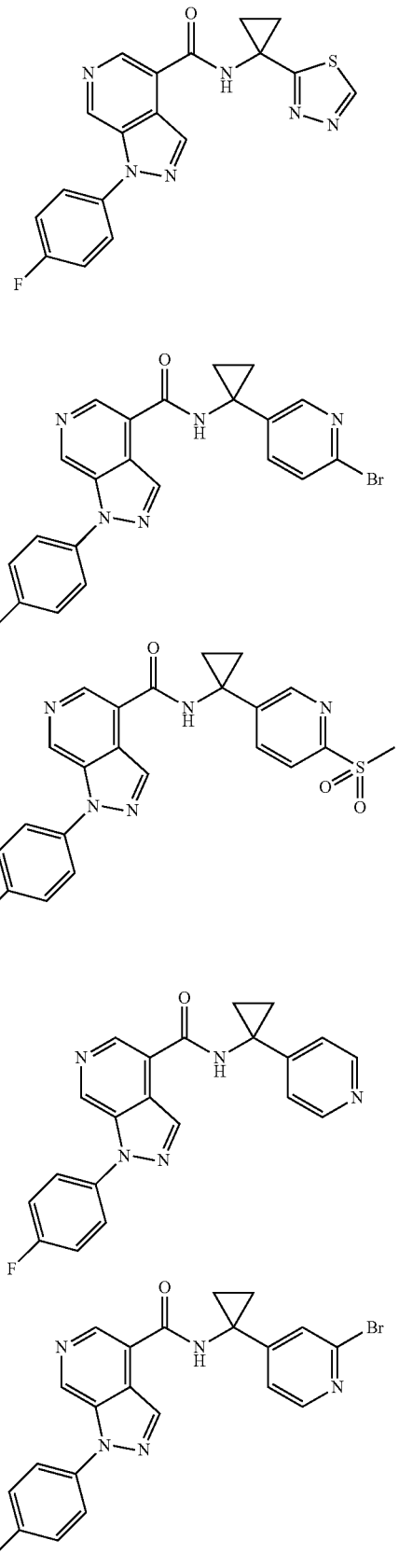

93
-continued
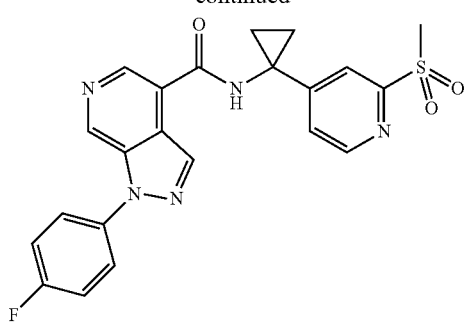
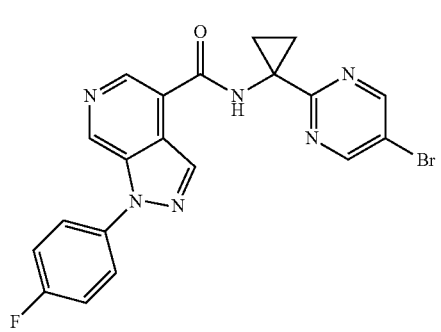
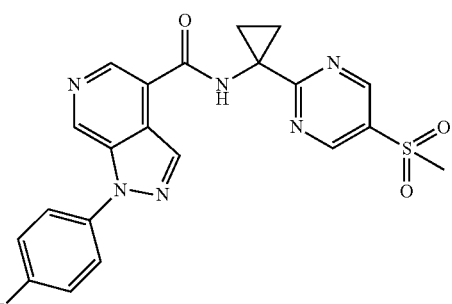
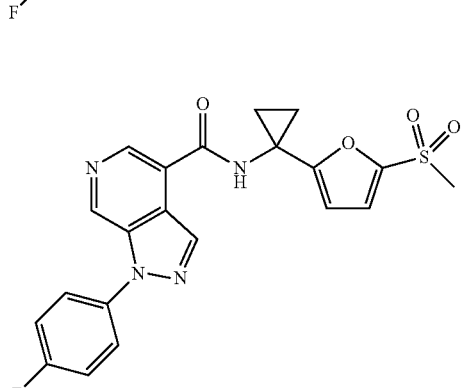
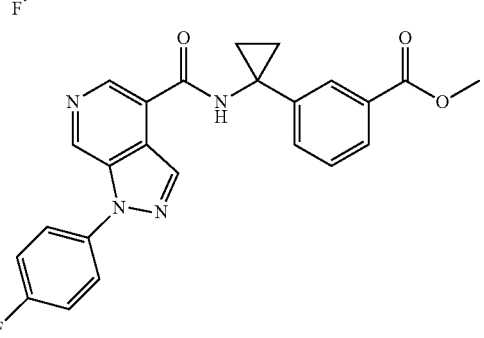
94
-continued
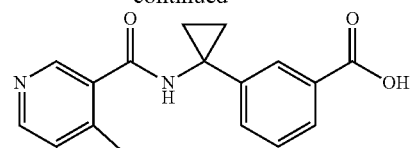
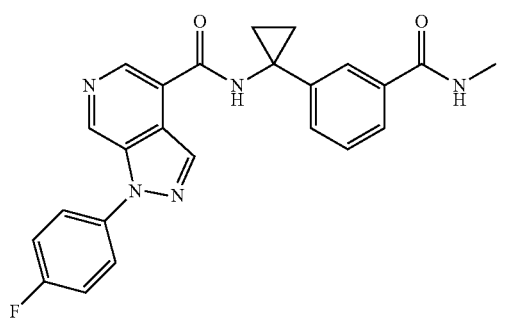
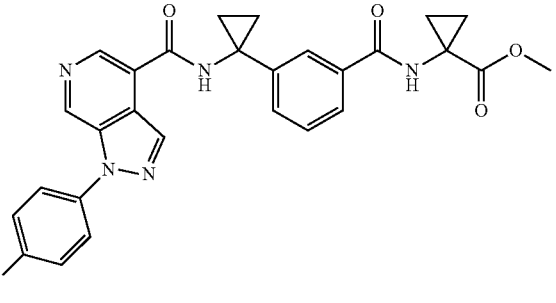
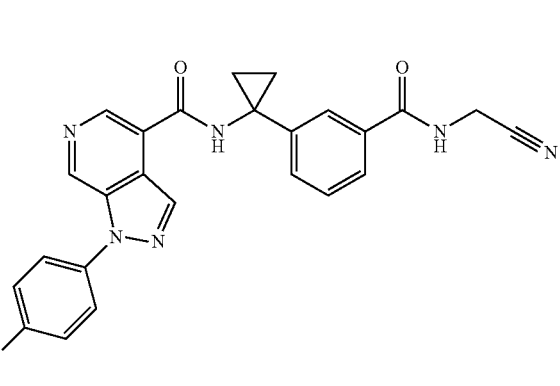
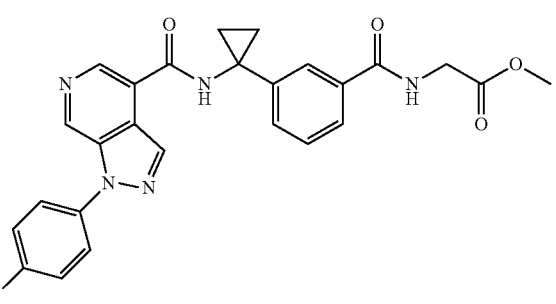

95
-continued
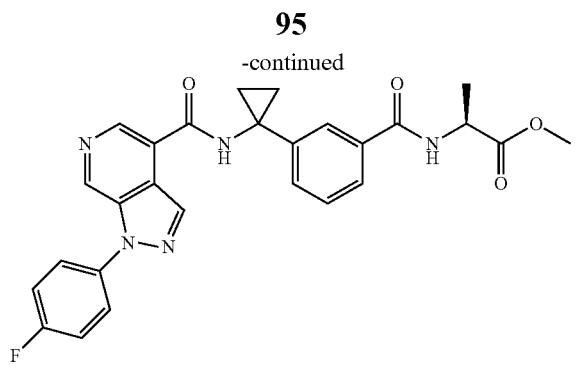
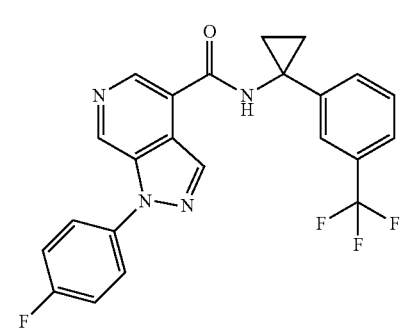
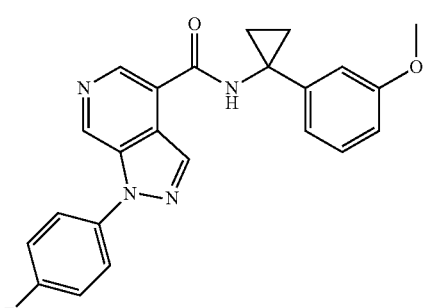
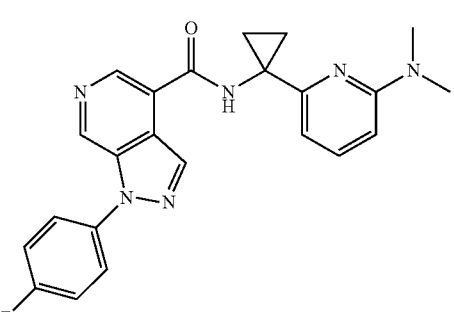
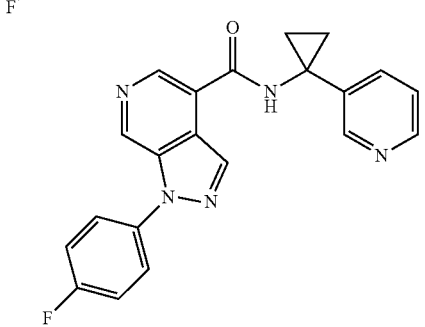
96
-continued
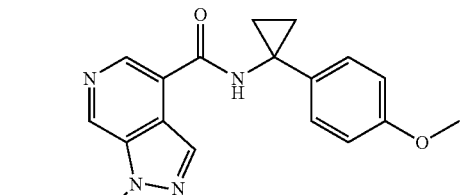
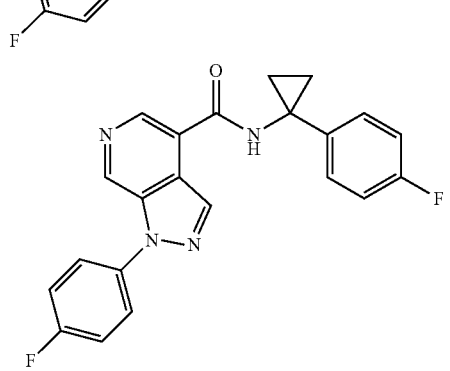
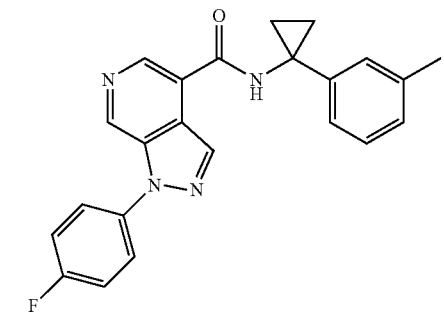
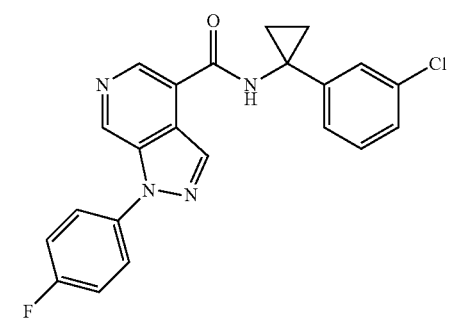
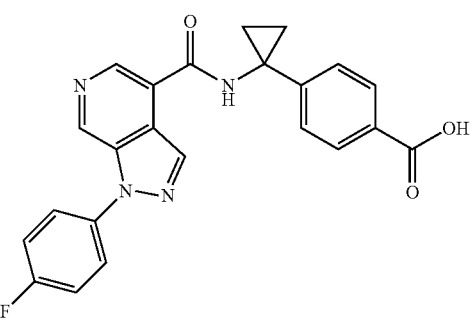

97
-continued
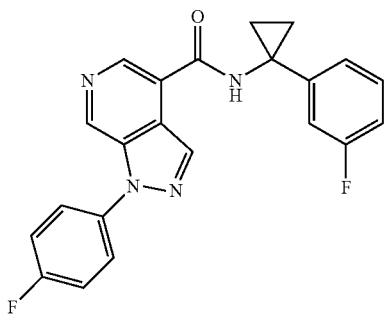
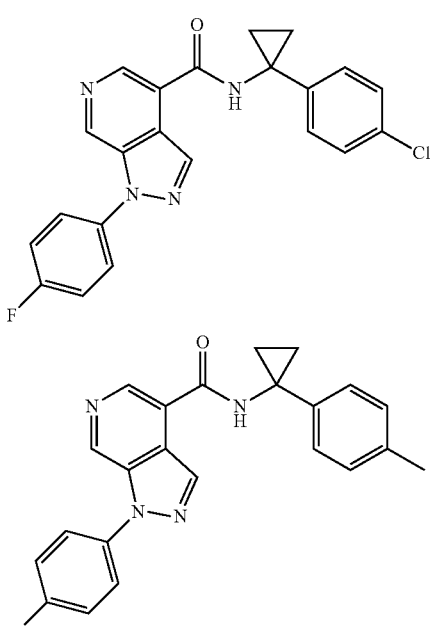
98
-continued
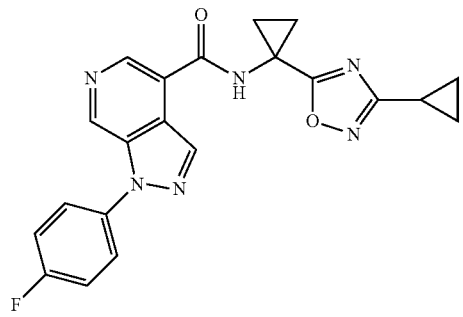
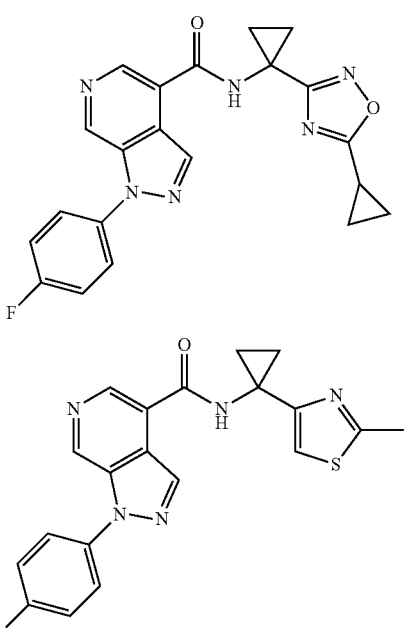
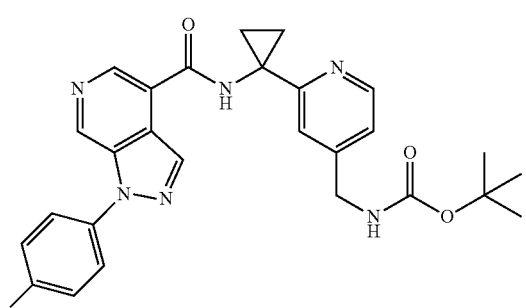
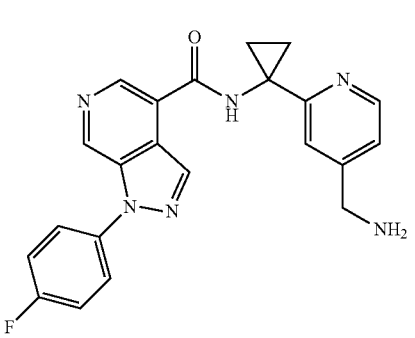

99
-continued
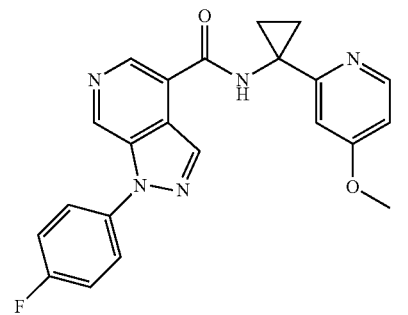
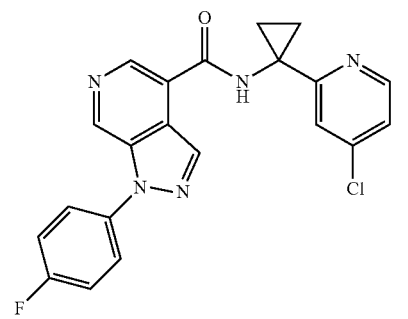
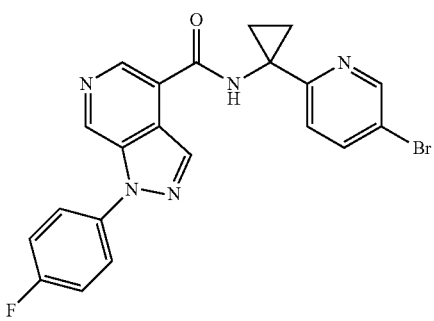
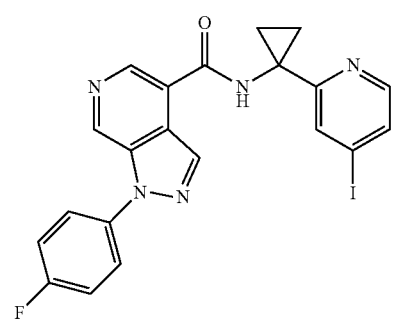
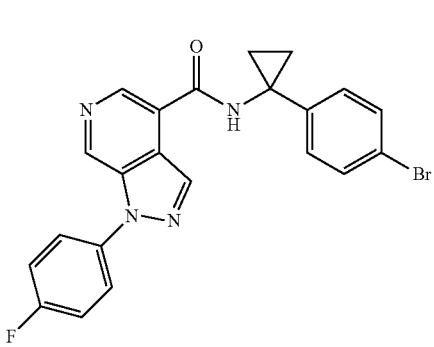
100
-continued
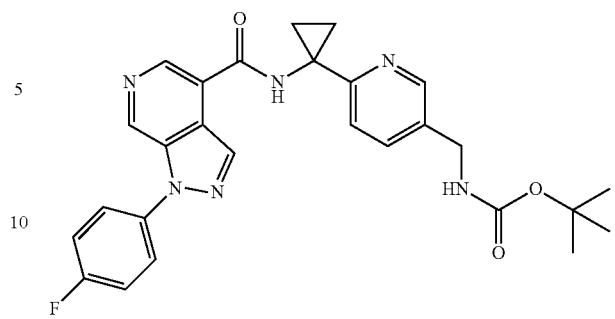
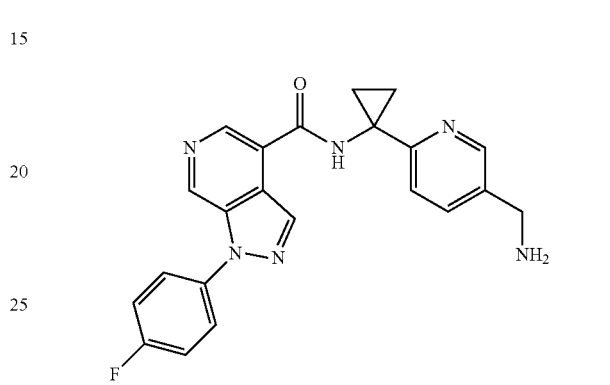
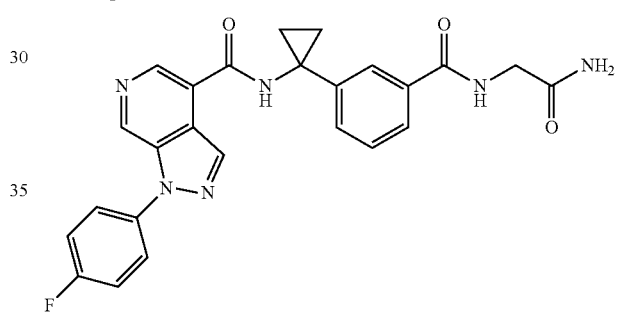
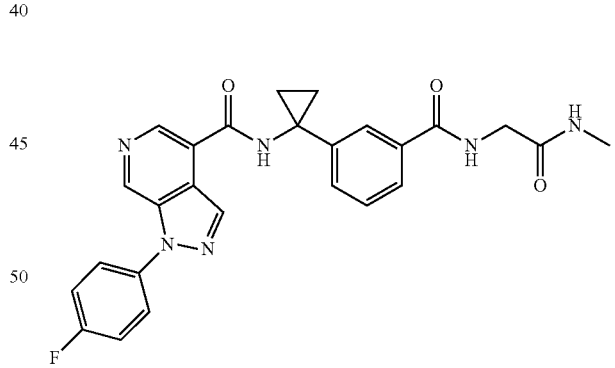
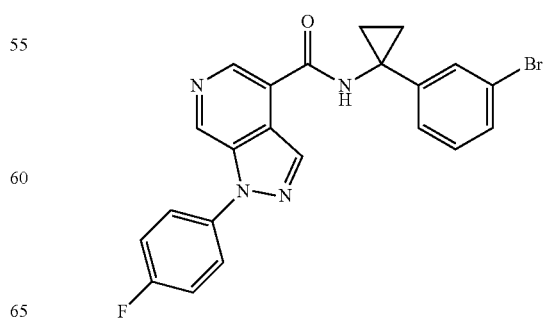

101
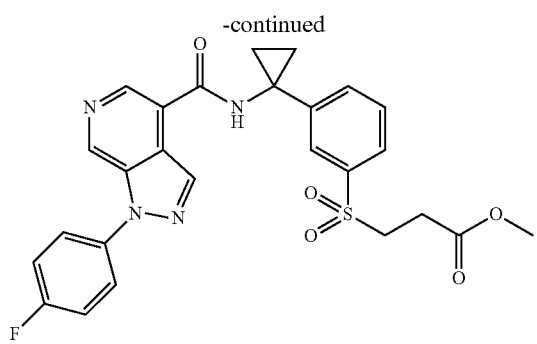
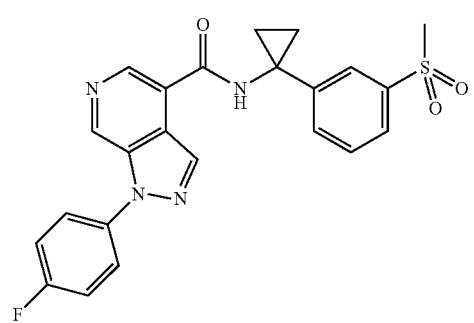
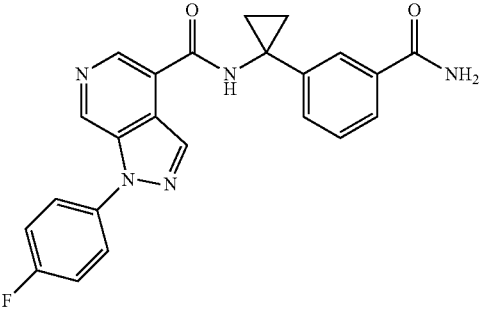
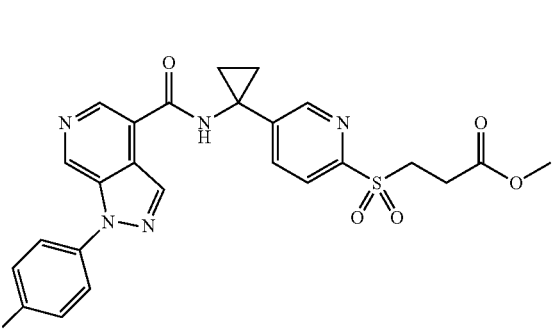
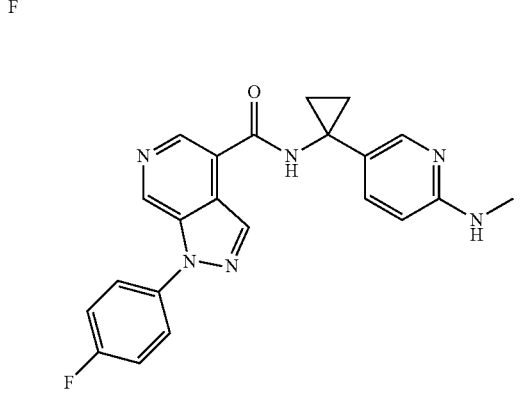
102
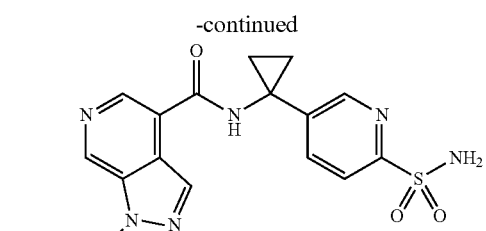
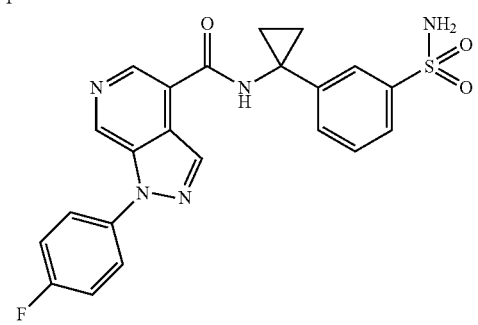
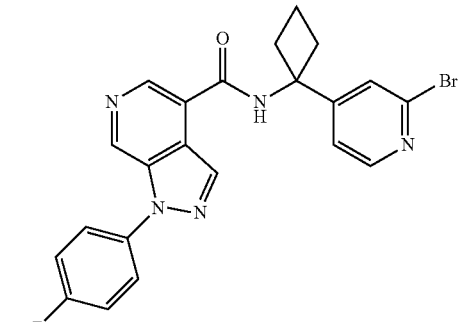
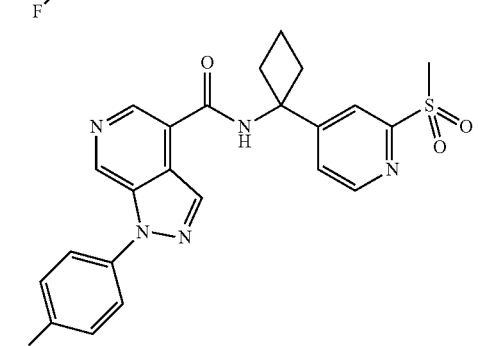
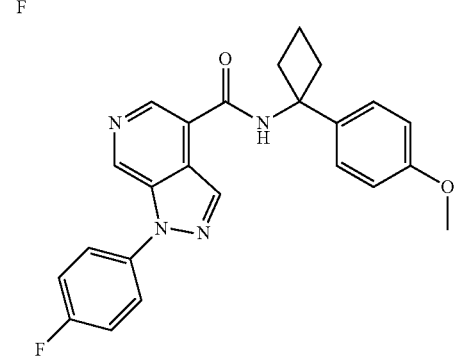

103
-continued

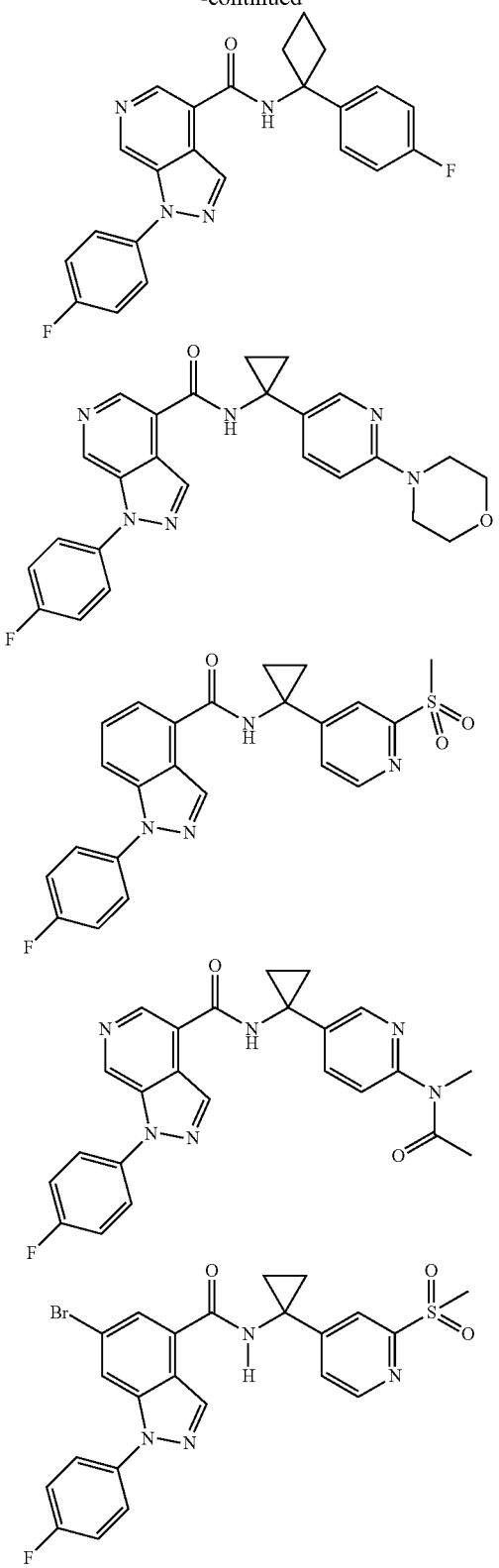

104
-continued

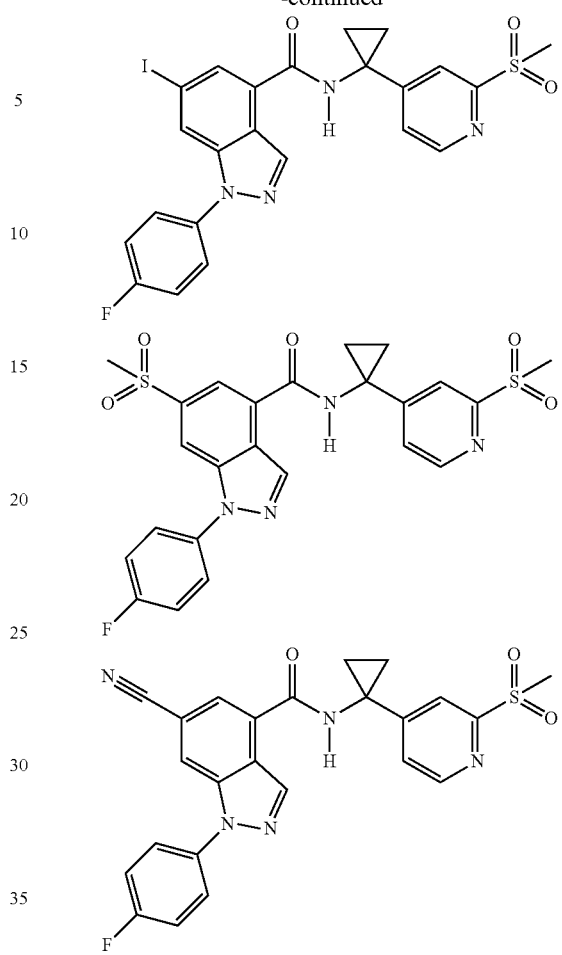

or a pharmaceutically acceptable salt thereof.

13. A pharmaceutical composition comprising a pharmaceutically effective amount of a compound according to claim 1 and one or more pharmaceutically carriers and/or adjuvants.

14. A method of treating chronic inflammation, allergies, contact dermatitis, psoriasis, rheumatoid arthritis, multiple sclerosis, type 1 diabetes, inflammatory bowel disease, Guillain-Barre syndrome, Crohn's disease, ulcerative colitis, graft versus host disease, Alzheimer's disease, asthma, chronic kidney disease, sepsis, autoimmune myocarditis and systemic lupus erythematosus, comprising administering to a patient in need thereof a pharmaceutically effective amount of a compound according to claim 1.

15. The method according to claim 14 wherein the treatment is for rheumatoid arthritis and multiple sclerosis.

16. The method according to claim 14 wherein the treatment is for rheumatoid arthritis.

17. The method according to claim 14 wherein the treatment is for multiple sclerosis.

* * * * *